(12) United States Patent
Kraig et al.

(10) Patent No.: US 12,324,827 B2
(45) Date of Patent: Jun. 10, 2025

(54) COMBINATION THERAPY FOR THE TREATMENT OF MIGRAINES

(71) Applicants: The University of Chicago, Chicago, IL (US); Seurat Therapeutics, Chicago, IL (US)

(72) Inventors: Richard Kraig, Chicago, IL (US); Lisa Won, Chicago, IL (US); Kae Pusic, Chicago, IL (US); Aya Pusic, Chicago, IL (US); Martin Sanders, Chicago, IL (US)

(73) Assignees: The University of Chicago, Chicago, IL (US); Seurat Therapeutics, Chicago, IL (US)

( * ) Notice: Subject to any disclaimer, the term of this patent is extended or adjusted under 35 U.S.C. 154(b) by 416 days.

(21) Appl. No.: 16/948,219

(22) Filed: Sep. 9, 2020

(65) Prior Publication Data

US 2021/0077591 A1    Mar. 18, 2021

Related U.S. Application Data

(60) Provisional application No. 62/946,122, filed on Dec. 10, 2019, provisional application No. 62/897,686, filed on Sep. 9, 2019.

(51) Int. Cl.
| | |
|---|---|
| *A61K 38/30* | (2006.01) |
| *A61K 9/00* | (2006.01) |
| *A61K 31/4545* | (2006.01) |
| *A61K 38/20* | (2006.01) |
| *A61K 38/21* | (2006.01) |
| *A61K 38/28* | (2006.01) |
| *A61K 39/395* | (2006.01) |
| *A61K 45/06* | (2006.01) |
| *A61P 25/04* | (2006.01) |
| *A61P 25/06* | (2006.01) |

(52) U.S. Cl.
CPC ............ *A61K 38/30* (2013.01); *A61K 9/0019* (2013.01); *A61K 9/0043* (2013.01); *A61K 31/4545* (2013.01); *A61K 38/2073* (2013.01); *A61K 38/217* (2013.01); *A61K 38/28* (2013.01); *A61K 39/3955* (2013.01); *A61K 45/06* (2013.01); *A61P 25/04* (2018.01); *A61P 25/06* (2018.01)

(58) Field of Classification Search
CPC ........ A61K 38/30; A61K 9/0019; A61P 25/06
See application file for complete search history.

(56) References Cited

U.S. PATENT DOCUMENTS

| | | | |
|---|---|---|---|
| 5,714,460 A | 2/1998 | Gluckman et al. | |
| 5,965,520 A | 10/1999 | Bennett | |
| 6,025,368 A | 2/2000 | Mascarenhas et al. | |
| 7,238,658 B2 | 7/2007 | Schaffer et al. | |
| 9,399,053 B2 * | 7/2016 | Kraig | ............... A61P 25/06 |
| 9,827,294 B2 * | 11/2017 | Kraig | ............... A61K 45/06 |
| 10,391,150 B2 | 8/2019 | Kraig et al. | |
| 2006/0029609 A1 | 2/2006 | Zankel et al. | |
| 2009/0093409 A1 | 4/2009 | Digicaylioglu et al. | |
| 2009/0099077 A1 | 4/2009 | Mriganka et al. | |
| 2009/0238886 A1 | 9/2009 | O'Mahony | |
| 2009/0264506 A1 | 10/2009 | Reinhard et al. | |
| 2010/0203168 A1 | 8/2010 | Zamoyski | |
| 2011/0014117 A1 | 1/2011 | Wang et al. | |
| 2019/0135927 A1 | 5/2019 | Levin | |

OTHER PUBLICATIONS

Penn et al., Bidirectional association between migraine and fibromyalgia: retrospective cohort analyses of two populations, 2019, BMJ Open, vol. 9, Issue 4, pp. 1-10 (Year: 2019).*
Han et al., CGRP monoclonal antibody for preventative treatment of chronic migraine: An update of meta-analysis, 2019, Brain and Behavior, vol. 9, Issue 2, pp. 1-6 (Year: 2019).*
Leal-Cerro et al., The Growth Hormone (GH)-Releasing Hormone—GH—Insulin-like Growth Factor-1 Axis in Patients with Fibromyalgia Syndrome, 1999, The Journal of Clinical Endocrinology & Metabolism, vol. 84, No. 9, pp. 3378-3381 (Year : 1999).*
Bohar et al., Evaluation of c-Fos immunoreactivity in the rat brainstem nuclei relevant in migraine pathogenesis after electrical stimulation of the trigeminal ganglion, 2013, Neurological Sciences, vol. 34, pp. 1597-1604 (Year: 2013).*
Tuncel (Oxidative Stress in Migraine with and Without Aura, 2008, Biological Trace Element Research, vol. 126, pp. 92-97 (Year: 2008).*
Cuatrecasas et al., Growth hormone treatment for sustained pain reduction and improvment in quality of life in severe fibromyalgia, 2012, Pain, vol. 153, pp. 1382-1389 (Year: 2012).*
De Tommaso, Prevalence, clinical features and potential therapies for fibromyalgia in primary headaches, 2014, Expert Review of Neurotherapeutics, vol. 12, Issue 3, pp. 287-296 (Year: 2014).*
"Demyelinating disease: What can you do about it?" *Mayo Clinic*, accessed from mayoclinicorg on Jul. 30, 2020.

(Continued)

*Primary Examiner* — Jeffrey Stucker
*Assistant Examiner* — Brittney E Donoghue
(74) *Attorney, Agent, or Firm* — Norton Rose Fulbright US LLP

(57) ABSTRACT

The current disclosure address a need in the art by providing methods and compositions for treating migraines and certain pain-related disorders with a combination therapy. Accordingly, aspects of the disclosure relate to a method for treating a migraine, post-traumatic headache, or chronic pain syndrome patient, the method comprising administering to the patient an effective amount of an insulin growth factor receptor (IGFR) activator and a calcitonin gene-related peptide (CGRP) inhibitor. Further aspects relate to a composition comprising insulin-like growth factor-1 (IGF-1) and a CGRP inhibitor. Also provided are methods for treating fibromyalgia or chronic fatigue syndrome in a patient, the method comprising administering to the patient an effective amount of an insulin growth factor receptor (IGFR) activator.

11 Claims, 17 Drawing Sheets

Specification includes a Sequence Listing.

(56) References Cited

OTHER PUBLICATIONS

Akpan et al., "Intranasal delivery of caspase-9 inhibitor reduces caspase-6-dependent axon/neuron loss and improves neurological function after stroke", J. Neurosci., 31(24):8894-8904, 2011.
Aurora, "Spectrum of illness: understanding biological patterns and relationships in chronic migraine", Neurology, 72(5 Suppl):S8-S13, 2009.
Beattie et al., "Control of synaptic strength by glial TNFalpha", Science, 295(5563):2282-2285, 2002.
Belanger et al., "Brain energy metabolism: focus on astrocyte-neuron metabolic cooperation", Cell Metab., 14(6):724-738, 2011.
Benedict et al., "Intranasal insulin improves memory in humans", Psychoneuroendocrinology, 29(10):1326-1334, 2004.
Berg, Random Walks in Bilogy, Princeton Univ. Press, NY, 1993.
Bitar et al., "Antinociceptive action of intrathecally administered IGF-I and the expression of its receptor in rat spinal cord." Brain Res. 1996; 737, 292-294.
Born et al., "Sniffing neuropeptides: a transnasal approach to the human brain", Nat. Neurosci., 5(6):514-516, 2002.
Brazier, "The problem of periodicity in the electro-encephalogram: studies in the cat", Electroencephalogr. Clin. Neurophysiol., 15:287-298, 1963.
Buzzi et al., "The antimigraine drug, sumatriptan (GR43175), selectively blocks neurogenic plasma extravasation from blood vessels in dura mater", Br. J. Pharmacol., 99:202-206, 1990.
Cabrera and Milton, "Human stick balancing: tuning Levy flights to improve balance control", Chaaos, 14(3):691-698, 2004.
Caggiano et al., "Long-term elevation of cyclooxygenase-2, but not lipoxygenase, in regions synaptically distant from spreading depression", J. Comp. Neurol, 376(3):447-462, 1996.
Carro et al., "Circulating insulin-like growth factor I mediates effects of exercise on the brain", J. Neurosci., 20(8):2926-2933, 2000.
Chen et al., "Pretreatment with interferon-gamma protects microglia from oxidative stress via up-regulation of Mn-SOD", Free Radic Biol. Med., 46(8):1204-1210, 2009.
Clark et al., "Impaired recognition memory in rats after damage to the hippocampus", J. Neurosci., 20(23):8853-8860, 2000.
Cohen et al., "Fremanezumab as Add-On Treatment for Patients Treated With Other Migraine Preventive Medicines." Headache 2017, 57, 1375-1384.
Correa et al., "The Nrf2-inducible antioxidant defense in astrocytes can be both up- and down-regulated by activated microglia:Involvement of p38 MAPK", Glia, 59(5):785-799, 2011.
Costa-Mattioli et al., "eIF2alpha phosphorylation bidirectionally regulates the switch from short- to long-term synaptic plasticity and memory", Cell, 129(1):195-206, 2007.
Costa-Mattioli et al., "Translational control of hippocampal synaptic plasticity and memory by the eIF2alpha kinase GCN2", Nature, 436(7054):1166-1173, 2005.
Costa-Mattioli et al., "Translational control of long-lasting synaptic plasticity and memory", Neuron., 61(1):10-26, 2009.
Cuatrecasas et al., "GH/IGF1 axis disturbances in the fibromyalgia syndrome: is there a rationale for GH treatment?" Pituitary 2014, 17, 277-283.
Darabaneanu et al., "Aerobic exercise as a therapy option for migraine: a pilot study", Int. J. Sports Med., 32(6):455-460, 2011.
De Rosa et al., "Intranasal administration of nerve growth factor (NGF) rescues recognition memory deficits in AD11 anti-NGF transgenic mice", Proc. Natl. Acad. Sci. USA., 102(10):3811-3816, 2005.
Duque et al., "Macrophage cytokines: involvement in immunity and infectious diseases" Frontiers in Immunology 2015, 5(491), 1-12.
Empl et al., "T-cell subsets and expression of integrins in peripheral blood of patients with migraine", Cephalalgia, 19(8):713-717, 1999.
Engelhardt and Ransohoff, "The ins and outs of T-lymphocyte trafficking to the CNS: anatomical sites and molecular mechanisms", Trends Immunol., 26(9):485-495, 2005.
Extended European Search Report Issued in Corresponding European Patent Application No. 19192519.7, dated Dec. 20, 2019.

Gkogkas et al., "Translational control mechanisms in long-lasting synaptic plasticity and memory", J. Biol. Chem., 285(42):31913-31917, 2010.
Gobbo and O'Mara, "Impact of enriched-environment housing on brain-derived neurotrophic factor and on cognitive performance after a transient global ischemia", Behav. Brain Res., 152(2):231-241, 2004.
Goddard et al., "Regulation of CNS synapses by neuronal MHC class I", Proc. Natl. Acad. Sci. USA., 104(16):6828-6833, 2007.
Grinberg and Kraig, "Oxidative stress from spreading depression preferentially rises in astrocytes and microglia, with the latter effect mitigated by IGF-1", Soc. Neurosci., 38:(In Press), 2012b.
Grinberg et al., "Insulin-like growth factor-1 lowers spreading depression susceptibility and reduces oxidative stress." J Neurochem. 2012; 122, 221-229.
Grinberg et al., "Intranasally Administered IGF-1 Inhibits Spreading Depression In Vivo" Brain Res. 2017; 1677, 47-57.
Guedes et al., "Malnutrition and brain function: experimental studies using the phenomenon of cortical spreading depression", Rev. Bras Biol., 56(Su 1 Pt. 2):293-301, 1996.
Gulati et al., "Possible role of free radicals in theophylline-induced seizures in mice", Pharmacology, Biochemistry and Behavior, 82:241-245, 2005.
Hallschmid et al., "Towards the therapeutic use of intranasal neuropeptide administration in metabolic and cognitive disordersa", Regul Pept., 149(1-3):79-83, 2008.
Haskew-Layton et al., "Controlled enzymatic production of astrocytic hydrogen peroxide protects neurons from oxidative stress via an Nrf2-independent pathway", Proc. Natl. Acad. Sci. USA, 107(40):17385-17390, 2010.
Hulse et al., "Monomeric IgG is neuroprotective via enhancing microglial recycling endocytosis and TNF-alpha", J. Neurosci., 28(47):12199-12211, 2008.
Hung et al., "The mechanism of heme oxygenase-1 action involved in the enhancement of neurotrophic factor expression", Neuropharmacology, 58(2):321-329, 2010.
Imitola et al., "Cytokines in multiple sclerosis: from bench to bedside", Pharmacol. Ther., 106(2):163-177, 2005.
International Search Report and Written Opinion issued in PCT/US2012/04683, mailed Jan. 23, 2013.
Jogie-Brahim et al., "Unraveling insulin-like growth factor binding protein-3 actions in human disease", Endocr. Rev., 30(5):417-437, 2009.
Johnston, et al., "Insulin-Like Growth Factor-1 is a Potent Neuronal Rescue Agent After Hypoxic-Ischemic Injury in Fetal Lambs," Journal of Clinical Investigation, 97(2): 300-308, 1996.
Juliana, "Anti-inflammatory compounds parthenolide and Bay 11-7082 are direct inhibitors of the inflammasome", J Biol Chem, 285: 9792-9802, 2010.
Juurlink et al., "Peroxide-scavenging deficit underlies oligodendrocyte susceptibility to oxidative stress", Glia, 22(4):371-378, 1998.
Kaneko et al., "Characteristics of bone marrow-derived microglia in the normal and injured retina", Invest. Ophthalmol Vis Sci., 49(9):4162-4168, 2008.
Kiefer, Dale. "The Link Between Chronic Migraine and Depression." Healthline, Feb. 2, 2017, https://www.healthline.com/health/migrane/link-between-chronic-migraine-and-depression. Accessed Jan. 23, 2019.
Kishida and Klann, "Sources and targets of reactive oxygen species in synaptic plasticity and memory", Antioxid. Redox. Signal, 9(2):233-244, 2007.
Koekkoek et al., "Intensive multifactorial treatment and cognitive functioning in screen-detected type 2 diabetes—The Addition—Netherlands study: A cluster-randomized trial", Journal of Neurological Sciences, 314:71-77, 2012.
Kopec et al., "Glutamate receptor exocytosis and spine enlargement during chemically induced long-term potentiation", J. Neurosci., 26(7):2000-2009, 2006.
Kraig et al., "Development of nasal insulin-like growth factor-1 as a treatment for migraine." American Headache Society 2019, 59, (Supplement 1) P221LB.

(56) References Cited

OTHER PUBLICATIONS

Kraig et al., "TNF-α and Microglial Hormetic Involvement in Neurological Health & Migraine", Dose Response, 8(4):389-413, 2010.
Kruger et al., "Repetitive spreading depression causes selective suppression of GABAergic function", Neuroreport, 7(15-17):2733-2736, 1996.
Kunkler and Kraig, "Calcium waves precede electrophysiological changes of spreading depression in hippocampal organ cultures", J. Neurosci., 18(9):3416-3425, 1998.
Kunkler and Kraig, "Reactive astrocytosis from excitotoxic injury in hippocampal organ culture parallels that seen in vivo", J. Cereb. Blood Flow Metab., 17(1):26-43, 1997.
Kunkler et al., "Hippocampal spreading depression bilaterally activates the caudal trigeminal nucleus in rodents." *Hippocampus* 2003; 13, 835-844.
Kunkler et al., "Multiplexed cytokine protein expression profiles from spreading depression in hippocampal organotypic cultures", J. Cereb. Blood Flow Metab., 24(8):829-839, 2004.
Kunkler et al., "Neural activity-dependent modulation of myelination", Sco. Neurosi., 32:87.5, 2006.
Kunkler et al., "Optical current source density analysis in hippocampal organotypic culture shows that spreading depression occurs with uniquely reversing currents", J. Neurosci., 25(15):3952-3961, 2005.
Lamas et al., "Effects of Interferon-gamma on Nitric Oxide Synthase Activity and Endothelin-1 Production by Vascular Endothelial Cells", J. Clin. Nvest, 90:879-887, 1992.
Lauritzen and Kraig, "Spreading Depression", In:The Headaches,Olsen et al. (Eds), 3rd Ed., Lippincott-Raven, Philadelphia, p. 269-276, 2005.
Lees and Cross, "A little stress is good: IFN-gamma, demyelination, and multiple sclerosis", J. Clin. Invest., 117(2):297-299, 2007.
Li et al., "Regional distribution of cortical interneurons and development of inhibitory tone are regulated by Cxcl12/Cxcr4 signaling", J. Neurosci., 28(5):1085-1098, 2008.
Lin et al., "Enhanced integrated stress response promotes myelinating oligodendrocyte survival in response to interferon-gamma", Am. J. Pathol., 173(5):1508-1517, 2008.
Lovatt et al., "The transcriptome and metabolic gene signature of protoplasmic astrocytes in the adult murine cortex", J. Nerosci., 27(45):12255-12266, 2007.
Mannerkorpi et al., "Acute effects of physical exercise on the serum insulin-like growth factor system in women with fibromyalgia." *BMC Musculoskelet Disord*. 2017, 18(37), 8 pages.
Mansuy et al., "Restricted and regulated overexpression reveals calcineurin as a key component in the transition from short-term to long-term memory", Cell., 92(1):39-49, 1998.
Mariani, "Targeting Cancer Cells—More pathways, more inhibitors, more trials" Highlights of 9th annual drug discovery technology world congress; Boston, MA. Accessed from www.medscape.com.
McGlade-McCulloh et al., "Individual microglia move rapidly and directly to nerve lesions in the leech central nervous system", Proc. Natl. Acad. Sci. USA, 86(3):1093-1097, 1989.
MedlinePlus 2015 "Migraine" accessed from www.nlm.nih.gov/medlineplus.
Melo-Carrillo et al., "Fremanezumab—A Humanized Monoclonal Anti-CGRP Antibody—Inhibits Thinly Myelinated (Aδ) But Not Unmyelinated (C) Meningeal Nociceptors" *J Neurosci*. 2017, 37:10587-10596.
Melo-Carrillo et al., "Selective Inhibition of Trigeminovascular Neurons by Fremanezumab: A Humanized Monoclonal Anti-CGRP Antibody" *J Neurosci*. 2017, 37(30), 7149-7163.
Mendes et al., "Lithium reduces Gsk3b mRNA levels: implications for Alzheimer Disease", Eur. Arch. Psychiatry Clin. Neurosci., 259(1):16-22, 2009.
Merkler et al., "Propagation of spreading depression inversely correlates with cortical myelin content", Ann. Neurol., 66(3):355-365, 2009.
Mitchell et al., "Cold pre-conditioning neuroprotection depends on TNF-α and is enhanced by blockade of interleukin-11", J. Neurochem., 117(2):187-196, 2011.
Mitchell et al., "Strategies for study of neuroprotection from cold-preconditioning", J. Vis. Exp., 2(43):pii02192, 2010.
Mody et al., "Low extracellular magnesium induces epileptiform activity and spreading depression in rat hippocampal slices", J. Neurophysiol., 57(3):869-888, 1987.
Moskowitz et al., "Neocortical spreading depression provokes the expression of c-fos protein-like immunoreactivity within trigeminal nucleus caudalis via trigeminovascular mechanisms." *J Neurosci*. 1993, 13, 1167-1177.
Muller et al., "Effects of interferons and hydrogen peroxide on CA3 pyramidal cells in rat hippocampal slice cultures", Brain Research, 619:157-162, 1993.
Mumby et al., "Hippocampal damage and exploratory preferences in rats: memory for objects, places, and contexts", Learn Mem., 9(2):49-57, 2002.
Nimmerjahn et al., "Resting microglial cells are highly dynamic surveillants of brain parenchyma in vivo", Science, 308(5726):1314-1318, 2005.
Nishijima et al., "Neuronal activity drives localized blood-brain-barrier transport of serum insulin-like growth factor-I into the CNS", Neuron, 67(5):834-846, 2010.
Nunez et al., "Insulin-like growth factor I modifies electrophysiological properties of rat brain stem neurons", J. Neurophysiol., 89(6):3008-3017, 2003.
O'Brien et al., "Laminin α2(merosine)-deficient muscular dystrophy and demyelinating neuropathy in two cats", Journal of the Neurological Science, 189:37-43, 2001.
Otamkhov et al., "Forskolin-induced LTP in the CA1 hippocampal region is NMDA receptor dependent", J. Neurophysiol., 91(5):1955-1962, 2004.
Otamkhov et al., "Persistent accumulation of calcium/calmodulin-dependent protein kinase II in dendritic spines after induction of NMDA receptor-dependent chemical long-term potentiation", J. Neurosci., 24(42):9324-9331, 2004.
Papadia et al., "Synaptic NMDA receptor activity boosts intrinsic antioxidant defenses", Nat. Neurosci., 11(4):476-487, 2008.
Popko et al., "The effects of interferon-gamma on the central nervous system", Mol. Neurobiol., 14(1-2):19-35, 1997.
Pusic and Kraig, "Inflammatory gene micro array profiling demonstrates 'T-cell-like' activation after recurrent spreading depression—Implications for migraine pathogenesis", Soc. Neurosci., 36:Prog #346.2, 2010.
Pusic et al., "Modeling neural immune signaling of episodic and chronic migraine using spreading depression in vitro", J. Vis. Exp., 52:2910, 2011.
Ramirez et al., "Inhibition of glycogen synthase kinase 3beta (GSK3beta) decreases inflammatory responses in brain endothelial cells", Am. J. Pathol., 176(2):881-892, 2010.
Rampon et al., "Enrichment induces structural changes and recovery from nonspatial memory deficits in CA1 NMDAR1-knockout mice", Nat. Neurosci., 3(3):238-244, 2000.
Ramsey et al., "Functional characterization of des-IGF-1 action at excitatory synapses in the CA1 region of rat hippocampus", J. Neurophysiol., 94(1):247-254, 2005.
Ren et al., "Brusatol enhances the efficacy of chemotherapy by inhibiting the Nrf2- mediated defense mechanism", Proc. Natl. Acad. Sci. USA, 108(4):1433-1438, 2011.
Reuter et al., "Nuclear Factor-kB as a Molecular Target for Migraine Therapy", Ann. Neurol., 51:507-516, 2002.
Reynolds, "Animals that randomly reorient at cues left by correlated random walkers do the Lévy walk", Am. Nat., 175(5):607-613, 2010b.
Reynolds, "Bridging the gulf between correlated random walks and Lévy walks: autocorrelation as a source of Lévy walk movement patterns", J. R. Soc. Interface, 7(53):1753-1758, 2010.
Rohl et al., "Activated microglia modulate astroglial enzymes involved in oxidative and inflammatory stress and increase the resistance of astrocytes to oxidative stress in vitro", Glia, 56(10):1114-1126, 2008.

(56) References Cited

OTHER PUBLICATIONS

Romera et al., "In vitro ischemic tolerance involves upregulation of glutamate transport partly mediated by the TACE/ADAM17-tumor necrosis factor-alpha pathway", J. Neurosci., 24(6):1350-1357, 2004.
Ruby et al., "Hippocampal-dependent learning requires a functional circadian system", Proc. Natl. Acad. Sci. USA, 105(40):15593-15598, 2008.
Selmeczi et al., "Cell motility as persistent random motion: theories from experiments", Biophys J., 89(2):912-931, 2005.
Selmeczi et al., "Cell motility as random motion: A review", In: The European Physical Journal Special Topics, 157(1):1-5, Springer Berlin/Heidelberg, 2008.
Shao and Dudek, "Both synaptic and intrinsic mechanisms underlie the different properties of population bursts in the hippocampal CA3 area of immature versus adult rats", J. Physiol., 587(Pt 24):5907-5923, 2009.
Silberstein and Olesen, "Cronich Migraines", In: The Headaches, 3rd Ed., Olsen et al. (Eds.), p. 613-617, Philadelphia, Lippincott-Raven, 2005.
Steinmetz and Turrigiano, "Tumor necrosis factor-a signaling maintains the ability of cortical synapses to express synaptic scaling", J. Neurosci., 30(44):14685-14690, 2010.
Stellwagen and Malenka, "Synaptic scaling mediated by glial TNF-alpha", Nature, 440(7087):1054-1059, 2006.
Stellwagen et al., "Differential regulation of AMPA receptor and GABA receptor trafficking by tumor necrosis factor-alpha", J. Neurosci., 25(12):3219-3228, 2005.
Stockhorst et al., "Insulin and the CNS: effects on food intake, memory, and endocrine parameters and the role of intranasal insulin administration in humans", Physiol. Behave., 83(1):47-54, 2004.
Takagi et al., "Functional analysis of spontaneous cell movement under different physiological conditions", PLoS One, 3(7):e2648, 2008.
Thorne et al., "Delivery of insulin-like growth factor-I to the rat brain and spinal cord along olfactory and trigeminal pathways following intranasal administration", Neuroscience, 127(2):481-496, 2004.
Thuret et al., "Hippocampus-dependent learning is associated with adult neurogenesis in MRL/MpJ mice", Hippocampus, 19(7):658-669, 2009.
Trepicchio et al., "Recombinant Human IL-11 Attenuates the Inflammatory Response Cytokine Through Down-Regulation of Proinflammatory Release and Nitric Oxide Production", J. Immunol, 157:3627-3634, 1996.
Viswanathan et al., "Optimizing the success of random searches", Nature, 401(6756):911-914, 1999.
Waldbaum and Dudek, "Single and repetitive paired-pulse suppression: a parametric analysis and assessment of usefulness in epilepsy research", Epilepsia, 50(4):904-916, 2009.
Waldbaum and Patel, "Mitochondria, oxidative stress, and temporal lobe epilepsy", Epilepsy Res., 88(1):23-45, 2010.
Won et al., "Insulin-like growth factor-1 inhibits spreading depression-induced trigeminal calcitonin gene related peptide, oxidative stress & neuronal activation in rat" *Brain Research* 2020, 1732:146673, 11 pages.
Won et al., "Nose-to-brain delivery of IGF-1 abrogates trigeminal system activation including oxidative stress and CGRP from recurrent spreading depression." *Soc. Neurosci.* 2019, 45: #3725.
Yildiz et al., "Acute hemorrhagic leukoencephalitis (Weston-Hurst syndrome) in a patient with relapse-remitting multiple sclerosis" Journal of Neuroinflammation 2015, 12:175.
Young et al., "Environmental enrichment inhibits spontaneous apoptosis, prevents seizures and is neuroprotective", Nat. Med., 5(4):448-453, 1999.
Ziv et al., "Immune cells contribute to the maintenance of neurogenesis and spatial learning abilities in adulthood.", Nat. Neurosci., 9(2):268-275, 2006.
Bookshelf, "The Voice of the Patent: Fibromyalgia", Oct. 2014.
Filiz, et al., "CGRP receptor antagonist MK-8825 attenuates cortical spreading depression induced pain behavior", *Cephalalgia*, vol. 39(3), pp. 354-365, 2019.
Forte, et al., "Treatments for Fibromyalgia in Adult Subgroups", *Comparative Effective ness Review*, vol. 148, 2015.
Zobdeh, et al., "Pharmacological treatment of migraine: Drug classes, mechanisms of action, clinical trials and new treatments", *Br J Pharmacol*, vol. 178, pp. 4588-4607, 2021.
De Tommaso, Marina, "Prevalence, clinical features and potential therapies for fibromyalgia in primary headaches." *Expert Review of Neurotherapeutics*, 12:3, 287-296, DOI: 10.1586/ern.11.190 (2012).
Extended European Search Report issued in European Patent Application No. 20862880.0, dated Sep. 14, 2023.

* cited by examiner

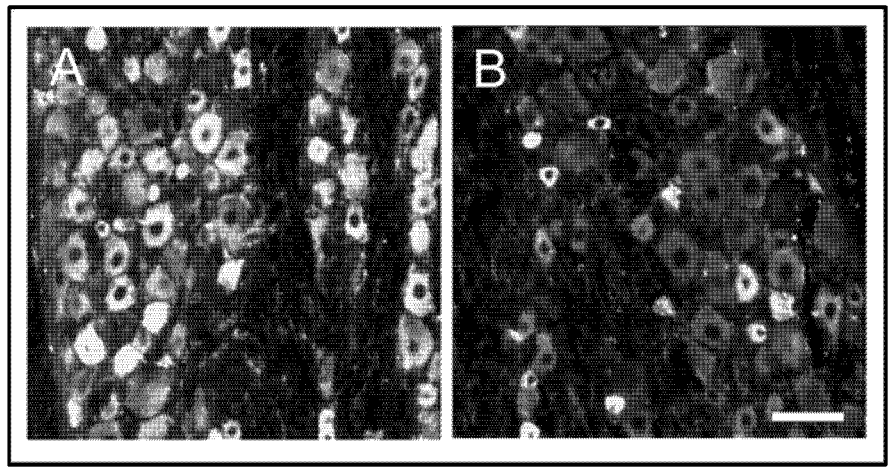
FIG. 1A-B
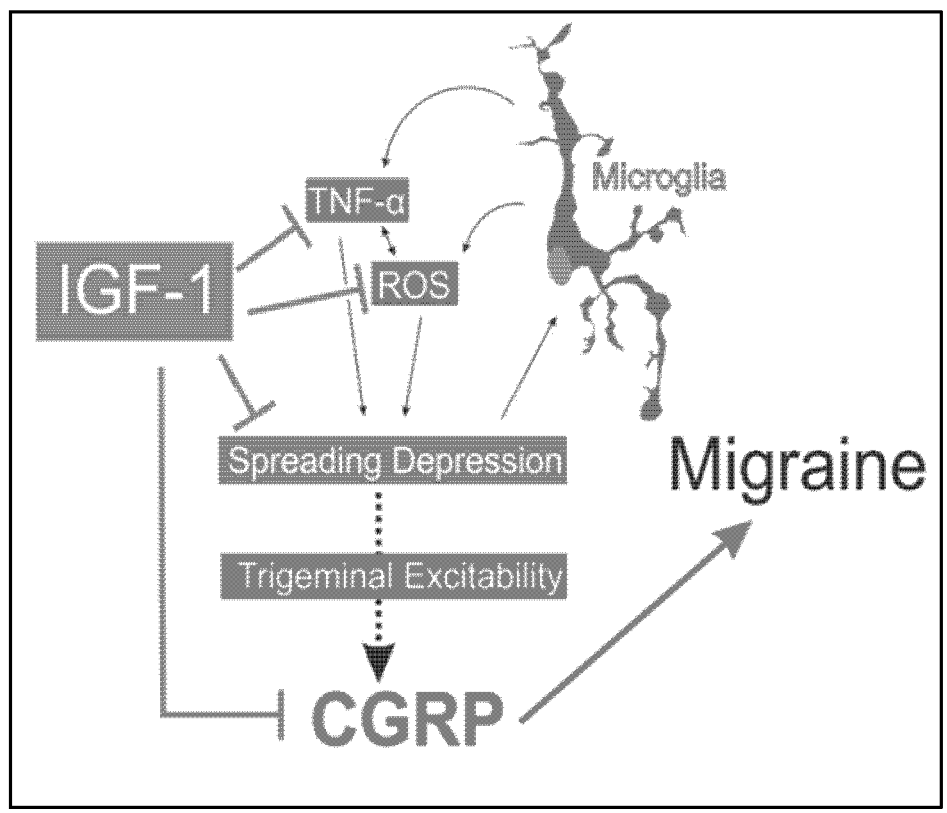
FIG. 2

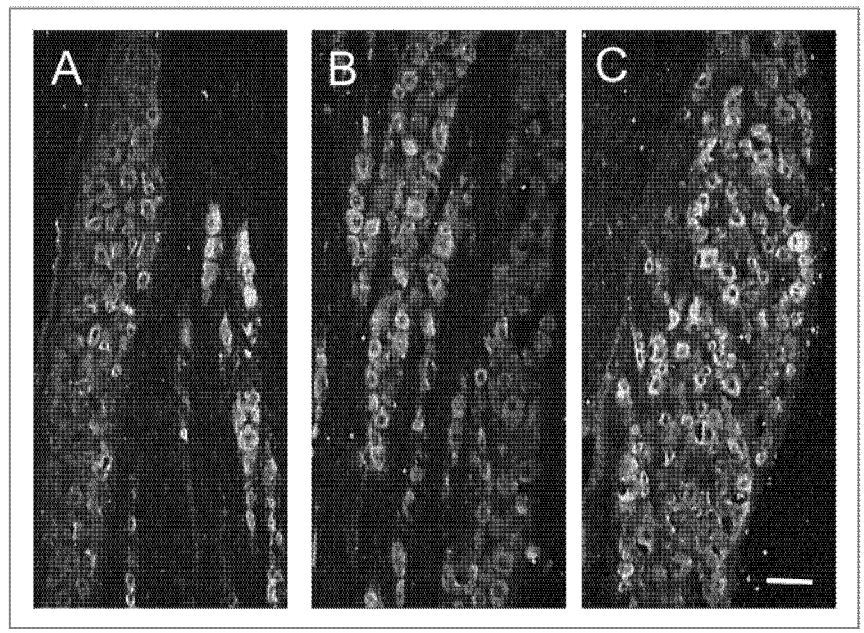
FIG. 5A-C
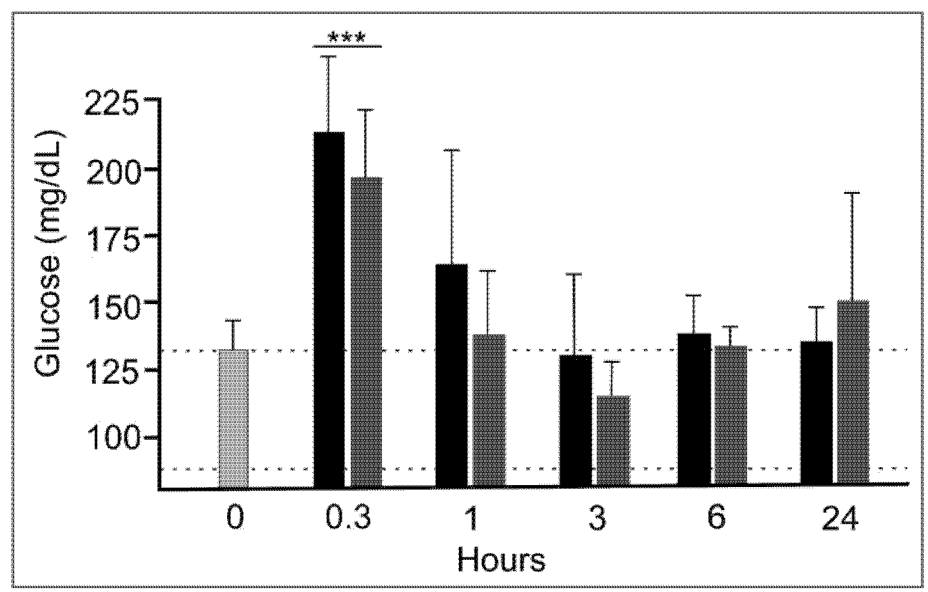
FIG. 6

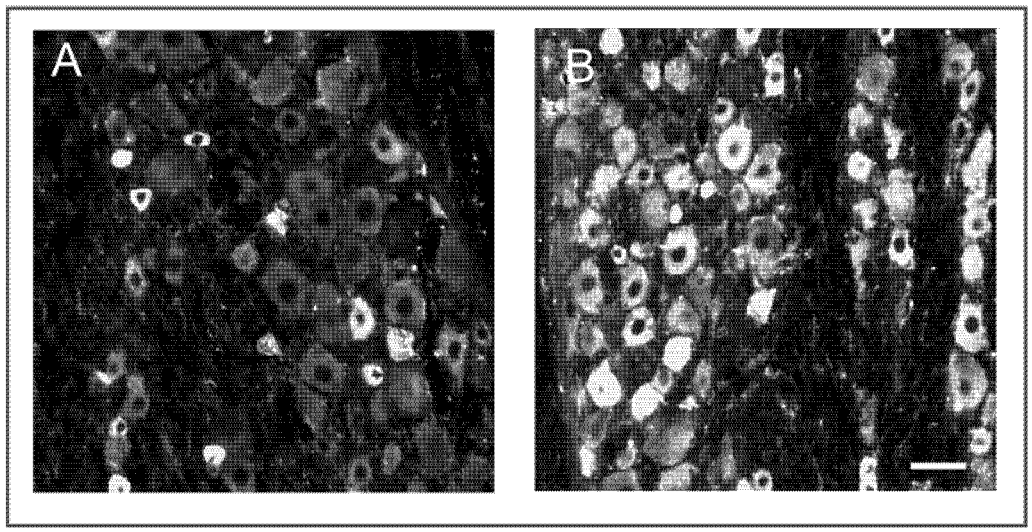
FIG. 7A-B
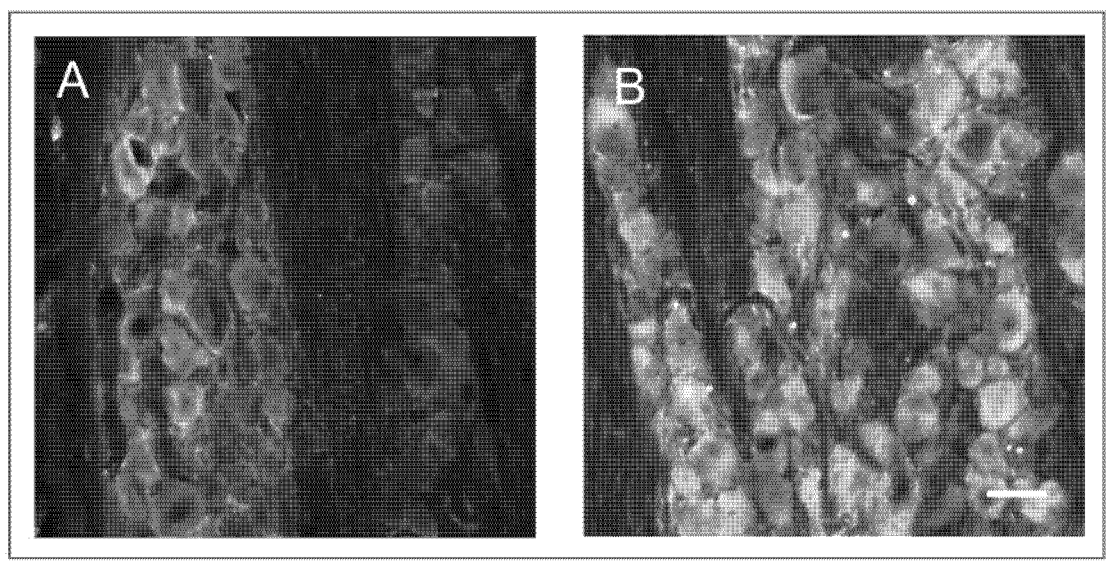
FIG. 8A-B

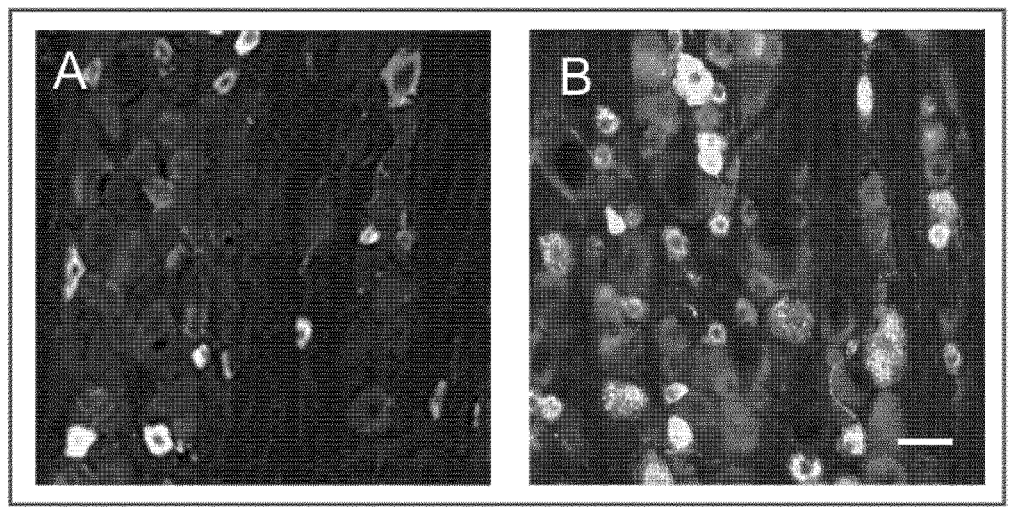
FIG. 9A-B
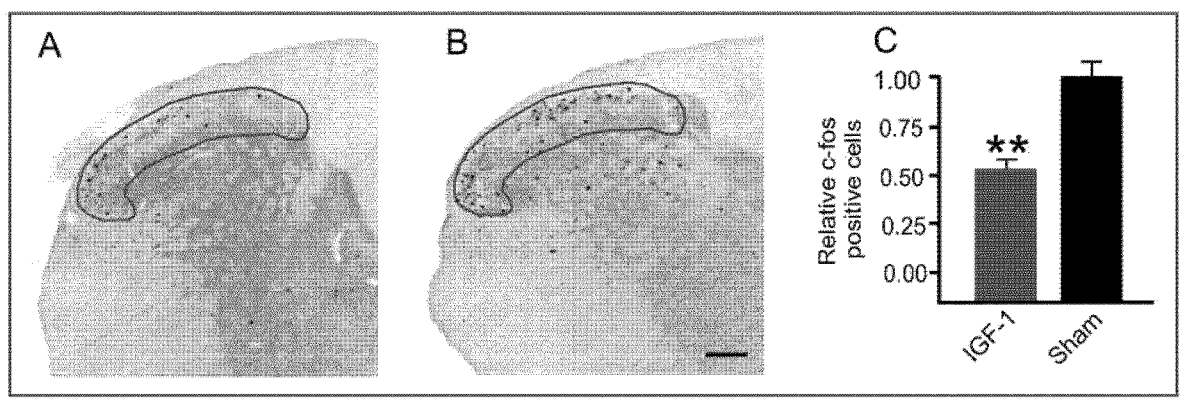
FIG. 10A-C

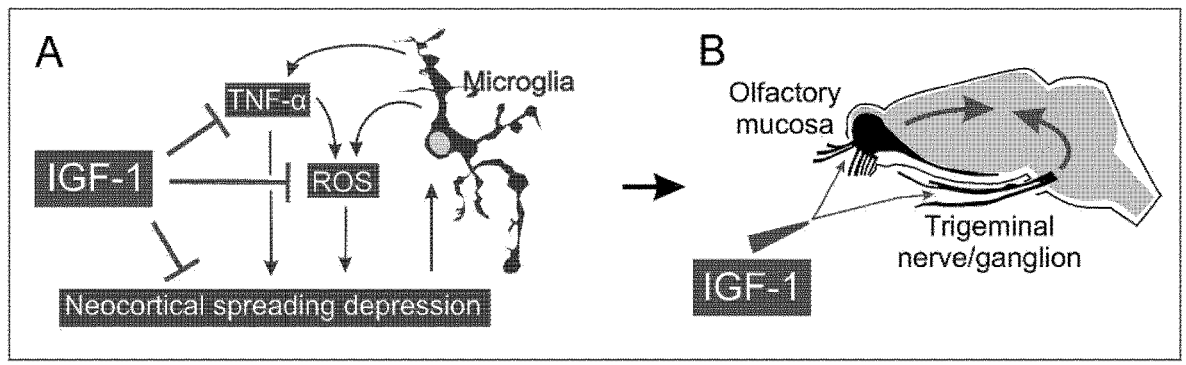
FIG. 11A-B
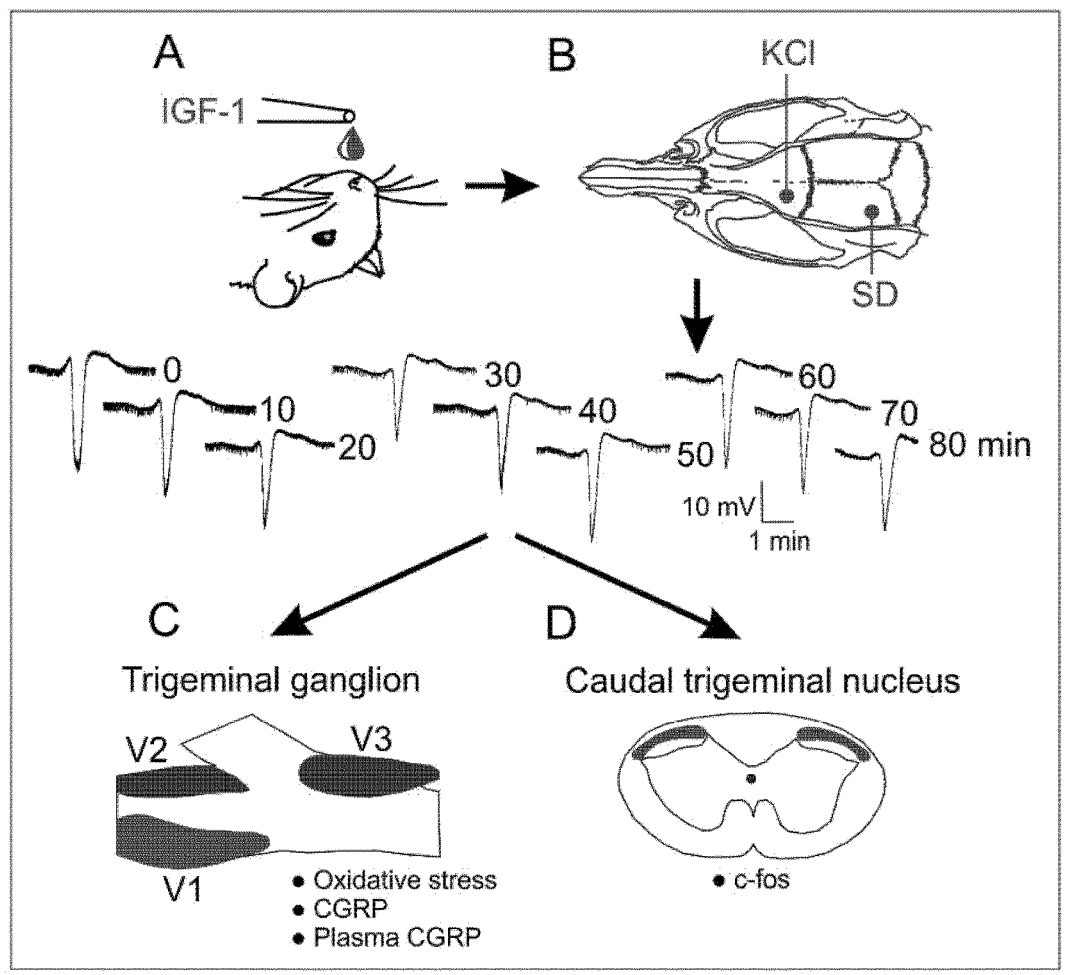
FIG. 12A-D

COMBINATION THERAPY FOR THE TREATMENT OF MIGRAINES

CROSS-REFERENCE TO RELATED APPLICATIONS

This application claims the benefit of priority of U.S. Provisional Patent Application No. 62/897,686 filed Sep. 9, 2019, and U.S. Provisional Patent Application No. 62/946,122 filed Dec. 10, 2019, all of which are hereby incorporated by reference in their entirety.

STATEMENT OF GOVERNMENT SUPPORT

This invention was made with government support under grant numbers NS019108 and NS108824 awarded by the National Institutes of Health. The government has certain rights in the invention.

BACKGROUND OF THE INVENTION

I. Field of the Invention

The present invention relates generally to medicine and neurology. In particular, embodiments are directed to the treatment of migraine and related neurological disorders.

II. Background

Migraine headache is a complex, recurrent disorder that is one of the most common complaints in medicine. In the United States, more than 30 million people have one or more migraine headaches per year. Approximately 75% of all persons who experience migraines are women.

Migraine was previously considered a vascular phenomenon that resulted from intracranial vasoconstriction followed by rebound vasodilation. Currently, however, the neurovascular theory describes migraine as primarily a neurogenic process with secondary changes in cerebral perfusion. The neurovascular theory holds that a complex series of neural and vascular events initiates migraine.

The theory of cortical spreading depression (CSD) has been advanced to explain the neurologic mechanism of migraine with aura. CSD is a well-defined wave of initial neuronal excitation followed by neuronal silence and then again excitation that returns to normal in cortical gray matter areas that spreads from its site of origin. This transient cellular depolarization is understood to cause the primary cortical phenomenon or aura phase; in turn, it activates trigeminal fibers causing the headache phase. Similar changes are understood to cause pain from migraine with and without aura. CSD is a wave of electrophysiological hyperactivity followed by a wave of inhibition, most often noted in the visual cortex. The scintillating scotoma (visual aura) of migraine in humans may be related to the neurophysiologic phenomenon termed the spreading depression of Leão.

Migraine treatment involves acute (abortive) and preventive (prophylactic) therapy. Patients with frequent attacks may require both. Acute treatments are intended to stop or prevent the progression of a headache or reverse a headache that has started. Preventive treatment, which is given even in the absence of a headache, is intended to reduce the frequency and severity of the migraine attack, make acute attacks more responsive to abortive therapy, and perhaps also improve the patient's quality of life. New CGRP antibodies represent an additional therapeutic approach to treating migraines. However, these therapies are not effective in every patient. The differential impact on activation of mechanosensitive primary afferent meningeal nociceptors may begin to explain why CGRP antibodies are not effective in all patients. Another important of consideration is that while these agents reduce nociceptive activation by blocking pain related CGRP in the trigeminal system, they do so without impacting the underlying causes of migraine—brain hyperexcitability and oxidative stress. Thus, there is a need in the art for improved therapies or combination treatments that may provide additional effectiveness.

SUMMARY OF THE INVENTION

The current disclosure address a need in the art by providing methods and compositions for treating migraines and certain pain-related disorders with a combination therapy. Accordingly, aspects of the disclosure relate to a method for treating a migraine, post-traumatic headache, or chronic pain syndrome patient, the method comprising administering to the patient an effective amount of an insulin growth factor receptor (IGFR) activator and a calcitonin gene-related peptide (CGRP) inhibitor. Further aspects relate to a composition comprising insulin-like growth factor-1 (IGF-1) and a CGRP inhibitor.

Further aspects relate to a method for treating spreading depression in a patient comprising administering to the patient an effective amount of an insulin growth factor receptor (IGFR) activator and a calcitonin gene-related peptide (CGRP) inhibitor. In some embodiments, spreading depression is further defined as spreading depression related demyelination. In some embodiments, the spreading depression related demyelination comprises spreading depression demyelination occurring or associated with multiple sclerosis, Parkinson's disease, Alzheimer's disease, acute or chronic post-traumatic brain injury, Amyotrophic Lateral Sclerosis, Huntington's disease, depression, schizophrenia, radiation-induced encephalitis, or oxygen-deprivation-induced encephalitis.

Further aspects relate to methods for treating ischemic stroke, toxin-induced encephalopathy, infectious agent-induced encephalopathy, or acute cerebral edema comprising administering to the patient an effective amount of an insulin growth factor receptor (IGFR) activator and a calcitonin gene-related peptide (CGRP) inhibitor. In some embodiments, spreading depression is further defined as spreading depression related demyelination. In some embodiments, treating a patient comprises treating or inhibiting spreading depression in the patient.

Further aspects relate to a method for treating a chronic pain syndrome patient, the method comprising administering to the patient an effective amount of an insulin growth factor receptor (IGFR) activator; wherein the chronic pain syndrome comprises fibromyalgia or chronic fatigue syndrome.

In some embodiments, the CGRP inhibitor comprises a CGRP antibody, a CGRP receptor antibody, an antigen binding fragment from a CGRP antibody or CGRP receptor antibody, a CGRP inhibitory fusion protein, a CGRP bioneutralizing agent, a CGRP receptor antagonists, a small molecule inhibitor, or a polypeptide inhibitor. In some embodiments, the antibody fragment comprises an scFv, a diabody, or a single domain antibody. In some embodiments, the antibody fragment comprises an antibody fragment described herein. In some embodiments, the antibody comprises a monoclonal antibody, a humanized antibody, a bivalent antibody, or a chimeric antibody. In some embodiments, the antibody is further defined according to antibody embodiments described herein.

In some embodiments, the migraine is further defined as chronic, acute, episodic, vestibular, ocular, complex, menstrual, acephalgic, hormonal, stress, cluster, or vascular. In some embodiments, the migraine is defined as chronic. In some embodiments, the migraine is defined as acute. In some embodiments, the migraine is defined as episodic. In some embodiments, the migraine is defined as cluster or as a cluster headache. In some embodiments, the migraine is further defined as high frequency migraine.

The term "acute migraine" is defined as a single attack and is typically used when discussing "acute" treatment for a migraine. "Acute" treatments are abortives to stop a given attack; "prophylactic medications" are used to reduce tendency for next attack (i.e., in high frequency or chronic migraine patients). Accordingly, in embodiments of the disclosure, the compositions of the disclosure may be further defined as prophylactic medications. In some embodiments the compositions of the disclosure may be further defined as an acute treatment. The term "episodic migraine" refers to a migraine in a patient that experiences, has experienced, or experiences on average 0-14 headache days per month. Chronic migraine is defined as a migraine in a patient that experiences, has experienced, or experiences on average 15 headache days or more per month. The term "high frequency migraine" refers to a migraine or headache in a patient that experiences, has experienced, or experiences on average 4-14 headaches a month.

In some embodiments, the patient is suffering from symptoms of a migraine. In some embodiments, the patient is suffering from acute migraine. In some embodiments, the patient is suffering from episodic migraine. In some embodiments, the patient is suffering from frequent migraine. In some embodiments, the patient is suffering from chronic migraine.

In some embodiments, the chronic pain syndrome comprises neurological pain, musculoskeletal pain, gastrointestinal pain, fibromyalgia, chronic fatigue syndrome, or heightened pain response.

In some embodiments, the IGFR activator comprises IGF-1 or insulin. In some embodiments, the IGFR activator comprises IGF-1. In some embodiments, the IGFR activator comprises a polypeptide of any one of SEQ ID NOS:1-5. In some embodiments, the IGFR activator comprises a polypeptide of SEQ ID NO:1 or a polypeptide with at least 80% identity to SEQ ID NO:1. In some embodiments, the IGFR activator comprises a polypeptide of SEQ ID NO:2 or a polypeptide with at least 80% identity to SEQ ID NO:2. In some embodiments, the IGFR activator comprises a polypeptide of SEQ ID NO:3 or a polypeptide with at least 80% identity to SEQ ID NO:3. In some embodiments, the IGFR activator comprises a polypeptide of SEQ ID NO:4 or a polypeptide with at least 80% identity to SEQ ID NO:4. In some embodiments, the IGFR activator comprises a polypeptide of SEQ ID NO:5 or a polypeptide with at least 80% identity to SEQ ID NO:5. In some embodiments, the IGFR activator comprises mecasermin. In some embodiments, the IGFR activator comprises a polypeptide with at least 75, 76, 77, 78, 79, 80, 81, 82, 83, 84, 85 86, 87, 88, 89, 90, 91, 92, 93, 94, 95, 96, 97, 98, 99, or 100% (or any derivable range therein) sequence identity to one of SEQ ID NOS:1-5.

In some embodiments, the CGRP inhibitor comprises a CGRP antibody or a CGRP receptor antibody. In some embodiments, the CGRP or CGRP receptor antibody comprises an inhibitory antibody. In some embodiments, the patient is administered an effective amount of an insulin growth factor receptor (IGFR) activator and a CGRP or CGRP receptor antibody antigen binding fragment comprising one or both of a heavy chain variable region and a light chain variable region from a CGRP or CGRP receptor antibody. In some embodiments, the heavy chain variable region comprises HCDR1, HCDR2, and HCDR3 from the heavy chain variable region of a CGRP or CGRP receptor antibody and/or wherein the light chain variable region comprises LCDR1, LCDR2, and LCDR3 from the light chain variable region of a CGRP or CGRP receptor antibody. In some embodiments, the heavy chain variable region and/or light chain variable region comprises the heavy chain variable region and/or light chain variable region of a CGRP or CGRP receptor antibody. In some embodiments, the antibody or antigen binding fragment comprises fremanezumab, erenumab, galcanezumab, eptinezumab, or an antigen binding fragment thereof. In some embodiments, the antibody comprises fremanezumab. In some embodiments, the antibody comprises an antigen binding fragment from fremanezumab.

In some embodiments, the CGRP inhibitor comprises a small molecule. In some embodiments, the small molecule comprises a gepant. In some embodiments, the inhibitor comprises one or more of atogepant, BI 44370, MK-3207, BMS-927711, olcegepant, rimegepant, telcagepant, and ubrogepant. In some embodiments, the small molecule comprises ubrogepant, rimegepant, atogepant, or combinations thereof.

In some embodiments, the IGFR activator and/or the CGRP inhibitor are administered parenterally, orally, and/or topically. In some embodiments, the IGFR activator and the CGRP inhibitor are in the same composition. In some embodiments, the IGFR activator and the CGRP inhibitor are in different compositions. In some embodiments, the method further comprises administering a second IGFR activator, and optionally wherein the second IGFR activator comprises insulin. In some embodiments, the composition comprises a second IGFR activator, and optionally wherein the second IGFR activator comprises insulin. In some embodiments, one or both of the IGFR activator and the CGRP inhibitor is administered to the patient intranasally. In some embodiments, the CGRP inhibitor is administered subcutaneously. In some embodiments, the IGFR activator is administered intranasally and the CGRP inhibitor is administered subcutaneously. In some embodiments, the CGRP inhibitor is administered parenterally.

In some embodiments, about 0.1 ng to about 2.0 g of IGFR activator is administered to the patient. In some embodiments, at least, at most, or about 0.1 ng, 0.5 ng, 1.0 ng, 5.0 ng, 10.0 ng, 25.0 ng, 50 ng, 75 ng, 100 ng, 125 ng, 150 ng, 175 ng, 200 ng, 225 ng, 250 ng, 275 ng, 300 ng, 325 ng, 350 ng, 375 ng, 400 ng, 425 ng, 450 ng, 575 ng, 600 ng, 625 ng, 650 ng, 675 ng, 700 ng, 725 ng, 750 ng, 775 ng, 800 ng, 825 ng, 850 ng, 875 ng, 900 ng, 925 ng, 950 ng, 975 ng, 1 µg, 10 µg, 20 µg, 30 µg, 40 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 800 µg, 825 µg, 850 µg, 875 µg, 900 µg, 925 µg, 950 µg, 975 µg, 1 mg, 2 mg, 3 mg, 4 mg, 5 mg, 6 mg, 7 mg, 8 mg, 9 mg, 10 mg, 11 mg, 12 mg 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 1 g, 1.5 g, or 2 g (or ranges derivable therein).

In some embodiments, about 0.1 ng to about 2.0 g of a CGRP inhibitor is administered to the patient. In some embodiments, at least, at most, or about 0.1 ng, 0.5 ng, 1.0 ng, 5.0 ng, 10.0 ng, 25.0 ng, 50 ng, 75 ng, 100 ng, 125 ng, 150 ng, 175 ng, 200 ng, 225 ng, 250 ng, 275 ng, 300 ng, 325 ng, 350 ng, 375 ng, 400 ng, 425 ng, 450 ng, 575 ng, 600 ng, 625 ng, 650 ng, 675 ng, 700 ng, 725 ng, 750 ng, 775 ng, 800 ng, 825 ng, 850 ng, 875 ng, 900 ng, 925 ng, 950 ng, 975 ng, 1 µg, 10 µg, 20 µg, 30 µg, 40 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 800 µg, 825 µg, 850 µg, 875 µg, 900 µg, 925 µg, 950 µg, 975 µg, 1 mg, 2 mg, 3 mg, 4 mg, 5 mg, 6 mg, 7 mg, 8 mg, 9 mg, 10 mg, 11 mg, 12 mg 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 1 g, 1.5 g, or 2 g (or ranges derivable therein).

In some embodiments, the CGRP inhibitor comprises Eptinezumab and is administered at a dose of 100 mg, 300 mg, or 100-300 mg. In some embodiments, a dose of Eptinezumab is administered every three months. In some embodiments, the CGRP inhibitor comprises Erenumab and is administered at a dose of 70 mg, 140 mg, or 70-140 mg. In some embodiments, a dose of Erenumab is administered every month. In some embodiments, the CGRP inhibitor comprises Fremanezumab and is administered at a dose of 225 mg, 675 mg, or 225-675 mg. In some embodiments, a dose of Fremanezumab is administered every month or every three months. In some embodiments, an initial dose of 675 mg of Fremanezumab is administered as an initial dose and followed by 225 mg administration as monthly doses or every 3 months. In some embodiments, the CGRP inhibitor comprises Galcanezumab and is administered at a dose of 120 mg, 240 mg, or 120-240 mg. In some embodiments, a dose of Galcanezumab is administered every month. It is also contemplated that the dose of the CGRP inhibitor, such as a dose administered herein may be reduced by at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80% (or any derivable range therein) when co-administered with an IGFR activator in the methods and compositions described herein.

In some embodiments, the patient is administered up to about 10 ml of a composition comprising the IGFR activator and/or CGRP inhibitor per dose. In some embodiments, the patient is administered up to about, at least about, or about 0.1, 0.2, 0.3, 0.4, 0.5, 0.6, 0.7, 0.8, 0.9, 1, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25 ml (or any derivable range therein).

In some embodiments, the method further comprises administering the IGFR activator and/or administering the CGRP inhibitor to the patient up to four times a day.

In some embodiments, the IGFR activator is administered 1-2 times per week for a period of at least 1 week. In some embodiments, the period comprises at least, at most, or about 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60 weeks, or any derivable range therein. In some embodiments, the IGFR activator is administered at least, at most, or exactly 1, 2, 3, 4, 5, 6, 7, or 8 times, or any derivable range therein, to the patient daily or at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, or 28 times, or any derivable range therein, to the patient in one week, or per week. In some embodiments, the IGFR activator is administered at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times, or any derivable range therein, to the patient in one month, or per month. In some embodiments, the IGFR activator is administered to the patient on a weekly, daily, or monthly basis for at least 1, 2, 3, 4, 5, 6, or 7 days or 1, 2, 3, or 4 weeks, or 1, 2, 3, 4, 5, 6, 7, 8, 9, 10, 11, or 12 months (or any derivable range therein).

In some embodiments, the CGPR inhibitor is administered at least, at most, or exactly 1, 2, 3, 4, 5, 6, 7, or 8 times, or any derivable range therein, to the patient daily or at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, or 28 times, or any derivable range therein, to the patient in one week, or per week. In some embodiments, the CGPR inhibitor is administered at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times, or any derivable range therein, to the patient in one month, or per month. In some embodiments, the CGPR inhibitor is administered to the patient on a weekly, daily, or monthly basis for at least 1, 2, 3, 4, 5, 6, or 7 days or 1, 2, 3, or 4 weeks, or 1, 2, 3, 4, 5, 6, 7, 8, 9, 10, 11, or 12 months (or any derivable range therein).

In some embodiments, the IGFR activator is administered at least every, at most every, or about every 2, 4, 6, 8, or 12 hours (or any derivable range therein). In some embodiments, the CGPR inhibitor is administered at least every, at most every, or about every 2, 4, 6, 8, or 12 hours (or any derivable range therein). In some embodiments, the IGFR activator and CGPR inhibitor or administered at the same time or within about 5, 10, 15, 20, 30, 60, 90, or 120 hours (or any derivable range therein) of each other. In some embodiments, the IGFR activator is administered at least, at most, or about 1, 2, 3, 4, 8, 12, 18, or 24 hours, or 1, 2, 3, 4, 5, 6, 7 days (or any derivable range therein) before the CGPR inhibitor. In some embodiments, the CGPR inhibitor is administered at least, at most, or about 1, 2, 3, 4, 8, 12, 18, or 24 hours, or 1, 2, 3, 4, 5, 6, 7 days (or any derivable range therein) before the IGFR activator. In some embodiments, the patient is administered one or both of the IGFR activator and the CGRP inhibitor daily, weekly, monthly, quarterly, or yearly.

In some embodiments, the method further comprises administering to the patient IL-11 and/or interferon γ. In some embodiments, the composition further comprises IL-11 and/or interferon γ. In some embodiments, the method alters the patient's central nervous system. In some embodiments, the composition alters the patient's central nervous system.

In some embodiments, the patient has experienced one or more migraines in a 4 week period or in a month. In some embodiments, the patient has experience more than, less than, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 migraines (or any derivable range therein) in a period of at least, at most, or about 1, 2, 3, 4, 5, 6, 7, 8, 9, or 10 weeks (or any derivable range therein) or at least, at most, or about 1 or 2 months or at least, at most, or about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 days (or any derivable range therein). In some embodiments, the patient has experienced at least one migraine lasting for at least 3 hours in the previous 24 hours prior to administration. In some embodiments, the patient has experienced at least or at most 1, 2, 3, 4, 5, 6, 7, 8, 9, 10, 11, 12, 13, or 14 migraine(s) lasting for at least 0.5, 1, 2, 3, 4, 5, or 6 hours (or any derivable range therein) in the previous 0.5, 1, 2, 3, 4, 5, 6, or 7 days (or any derivable range therein) prior to administration. In some embodiments, the patient is one that, on average, experiences 14 or fewer migraines within a month. In some embodiments, the patient is one that experiences or has experienced 14 or fewer migraines within a month.

In some embodiments, the patient is a human patient that is 18 years or older. In some embodiments, the patient is a pediatric patient of less than 18 years. In some embodiments, the patient is younger than 50. In some embodiments, the patient is older than 50. In some embodiments, the patient is at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 years old (or any derivable range therein).

In some embodiments, the patient is a human patient. In some embodiments, the patient is dog, cat, mouse, rat, horse, pig, or rabbit.

In some embodiments, the migraine is further defined as a migraine with aura. In some embodiments, the patient is further defined as one that has one or more symptoms comprising visual disruptions, numbness, dizziness, speech disruptions, ataxia, dysarthria, vertigo, tinnitus, hypacusis, diplopia, decreased consciousness, allodynia, and unilateral visual disruptions. In some embodiments, the symptom is further being defined as on one aspect of the head or neck. In some embodiments, the aura or symptom begins before the headache begins. In some embodiments, the aura or symptom begins at least or at most 1, 2, 3, 4, 5, 6, 7, 8, 9, 10, 11, or 12 hours (or any derivable range therein) before the headache begins. In some embodiments, the patient has not had or has not been diagnosed with ischemia. In some embodiments, the migraine is further defined as a migraine without aura.

In some embodiments, the patient is also administered an anti-migraine drug. In some embodiments, the composition further comprises an anti-migraine drug. In some embodiments, the anti-migraine drug comprises a 5-HT1F (ditan) receptor agonist. In some embodiments, the anti-migraine drug comprises one or more of alniditan, lasmiditan (COL-144), and LY-334370.

In some embodiments, the anti-migraine drug is in the same composition as the IGFR activator. In some embodiments, the anti-migraine drug is in the same composition as the CGPR inhibitor. In some embodiments, the anti-migraine drug comprises acetaminophen or ibuprofen. In some embodiments, the patient is administered the anti-migraine drug within 24 hours of being administered the composition.

In some embodiments, the method further comprises administering an additional agent. In some embodiments, the composition comprises an additional agent. In some embodiments, the additional agent either activates or inhibits pituitary adenylate cyclase-activating peptide (PACAP), vasoactive intestinal peptide (VIP), PACAP/VIP receptors (PAC1, VPAC1 and VPAC2). In some embodiments, the additional agent comprises one or more of an inhibitor of PACAP, VIP, PACAP receptor, and VIP receptor. In some embodiments, the additional agent either activates or inhibits transient receptor potential (TRP) channels. In some embodiments, the additional agent comprises one or more of an inhibitor of TRP and TRP receptor. In some embodiments, the IGFR activator, CGRP inhibitor, anti-migraine drug, and/or additional agent are co-administered and/or are in the same composition. In some embodiments, the additional agent comprises a polypeptide, nucleic acid, or small molecule. In some embodiments, treating comprises reducing brain hyperexcitability, reducing spreading depression, and/or reducing oxidative stress. In some embodiments, treating comprises reducing oxidative stress in the trigeminal system. The spreading depression may further be defined as cortical spreading depression.

In some embodiments, the compositions of the disclosure are formulated for intranasal, parenteral, oral, subcutaneous, intravenous, and/or topical administration. In some embodiments, the compositions of the disclosure are formulated for a route of administration described herein.

In some embodiments, the compositions or methods of the disclosure exclude an additional anti-migraine therapy or an additional therapy. In some embodiments of the disclosure, the compositions and methods exclude a EPO. In some embodiments of the disclosure, the compositions and methods exclude agents in addition to the therapeutic agents in recited in the claims. For example, compositions and methods of the disclosure may exclude one or more of a cytokine, growth factor, inhibitor, antigen binding fragment from an antibody, or analgesic. This exclusion applies in addition to the elements and therapeutic agents recited in the claims. For example, the claims may recite administration of an antibody in the method of the disclosure but may exclude the administration of an additional antibody that is not recited in the method of the disclosure.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Nasal IGF-1 significantly reduced level of CGRP in the trigeminal ganglion (TG). Rats (n=5/group) were anesthetized with isoflurane and treated with succinate buffer (sham) or IGF-1 (150 µg) in 50 µL. 24 hours later animals were re-anesthetized, brains harvested and processed for CGRP immunostaining of the TG. Images were obtained from each animal and image fluorescence intensity quantified via a digital imaging strategy. Three images were measured per animal and the averages recorded. Nasal delivery and image processing was completed while blinded to conditions. Experiments, immunostaining and imaging were done in pairs (i.e., sham and IGF-1) to reduce potential variability. Staining ratios (IGF-1/sham) were converted to natural logs so that 0 corresponded to no difference and a value less than 0 meant IGF-1 reduced CGRP and so that a t-test could be used to determine if difference in logs varied significantly from 0 (Kraig et al., J Neurosci, 1991). Representative results show (A) succinate sham TG CGRP immunostaining and (B) the reduction in CGRP staining after nasal IGF-1. This reduction was significant (p<0.001; alpha=0.05; power of 1.00). Scale bar=50 µm.

FIG. 2. Schematic of IGF-1 results from in vitro and in vivo studies. Initial studies done using hippocampal brain slice cultures show that IGF-1 inhibits spreading depression (SD) by abrogating microglial activation and release of TNFα and reactive oxygen species (ROS). It has been shown that SD in vivo leads to trigeminal system activation which is known to increase levels of CGRP. Nasal delivery of IGF-1 reduces trigeminal ganglion CGRP expression and therefore it is likely that it will also reduce SD induced CGRP there, and by extension migraine.

FIGS. 5A-C. Trigeminal ganglion IGF-1 receptor distribution. Representative images show that IGF-1 can have direct ligand-receptor interactions via its cognate receptor that is found throughout the adult rat trigeminal ganglion [(A) V1, ophthalmic division; (B) V2, maxillary division; and (C) V3, mandibular division]. Scale bar=50 µm.

FIG. 6. Nose to brain (N2B) treatment with IGF-1 did not cause hypoglycemia. Serum glucose was measured in non-fasted rats under brief isoflurane anesthesia after N2B delivery of vehicle (black) or IGF-1 (red) compared to immediately before treatments (light gray). As expected, glucose rose at the conclusion of N2B treatments due to continued isoflurane exposure. However, no significant differences were seen between treatment pairs (t-test) or 0 time (light gray) versus other values when compared via ANOVA plus post hoc Holm-Sidak except at the 0.3 hour point (***p<0.001). The lowest IGF-1 glucose-related level seen was 114 mg/dL [compared to control (132 mg/dL; time 0)], which is within the normal range for Wistar rats [85-132 mg/dL]. Dotted lines show normal glucose range. While the glucose level that defines hypoglycemia is variable, a drop of 1 mM is not considered hypoglycemic. Furthermore, no IGF-1 glucose level was hypoglycemic. Results shown as mean±SEM.

FIGS. 7A-B. Nose-to-brain (N2B) delivery of IGF-1 significantly reduced CGRP levels in the trigeminal ganglion of naïve animals. Representative images show CGRP immunostaining of the V1 area of the trigeminal ganglion after treatment with (A) IGF-1 or (B) vehicle. Natural log ratio levels of immunostaining levels after N2B treatment (IGF-1/sham) showed that IGF-1 significantly (p<0.001) reduced CGRP levels by 75%. Scale bar=25 µm.

FIGS. 8A-B. Nose-to-brain (N2B) delivery of IGF-1 significantly reduced oxidative stress in the trigeminal ganglion after recurrent spreading depression. Representative images show malondialdehyde immunostaining of the V1 area of the trigeminal ganglion after pre-treatment with (A) IGF-1 or (B) vehicle which was followed a day later by 90 minutes of recurrent spreading depression. Natural log ratio levels of immunostaining after N2B treatment (IGF-1/sham) showed that IGF-1 significantly (p<0.001) reduced malondialdehyde levels by 82%. Scale bar=25 µm.

FIGS. 9A-B. Nose-to-brain (N2B) delivery of IGF-1 significantly reduced CGRP levels in the trigeminal ganglion after recurrent spreading depression. Representative images show CGRP immunostaining of the V1 area of the trigeminal ganglion after pre-treatment with (A) IGF-1 or (B) vehicle which was followed a day later by 90 minutes of recurrent spreading depression. Natural log ratio levels of immunostaining after N2B treatment (IGF-1/sham) showed that IGF-1 significantly (p<0.001) reduced CGRP levels by 44%. Scale bar=25 µm.

FIGS. 10A-C. Nose-to-brain (N2B) delivery of IGF-1 significantly reduced caudal trigeminal nucleus c-fos labelling after recurrent spreading depression. Representative images show c-fos immunostaining at −4.5 mm caudal to the obex within (red area of interest) laminae I and II of the caudal trigeminal nucleus after pre-treatment with (A) IGF-1 or (B) succinate buffer which was followed a day later by 90 minutes of recurrent spreading depression. (C) The number of c-fos positive nuclei at this level, the predominant caudal trigeminal nucleus area of activation from spreading depression, was significantly (**p=0.003) reduced by 48%. Scale bar=200 µm.

FIGS. 11A-B. Summary nasal IGF-1 data and its relation to the impact of anti-CGRPs for migraine modeled in rats. (A) Work using rat hippocampal brain slice cultures, showed that IGF-1 significantly inhibited spreading depression, a model of migraine, by selectively reducing microglial tumor necrosis factor alpha (TNF-α) production and reactive oxygen specifies (ROS), factors that otherwise promote spreading depression (Grinberg et al., 2017). (B) In a second phase of development, nasal delivery of IGF-1, which is known to rapidly enter brain via the olfactory and trigeminal nerve pathways, significantly inhibited spreading depression in whole animals.

FIGS. 12A-D. Paradigm for study of the impact of intranasal delivery of human recombinant IGF-1 on trigeminal system activation after spreading depression (SD). (A) IGF-1 (150 µg/50 µL) [or vehicle (sham)] was administered to rats over 20 minutes in a recumbent position while under inhalational isoflurane anesthesia. (B) 24 hours later, SD was induced every 9-10 minutes for 90 minutes via pressurized episodic micro-injections of nL amounts of 0.5 M KCl into rostral neocortex with confirmation of SD established via electrophysiological microelectrode recordings from caudal neocortex. Representative SDs are shown. Immediately after SD, tissues were harvested for immunostaining assessment of trigeminal system activation in the trigeminal ganglion using OS lipid peroxidation marker, malondialdehyde, and CGRP (C) and c-fos in the caudal trigeminal nucleus (D).

DETAILED DESCRIPTION OF THE INVENTION

I. IGFR Activator

Figure 3:
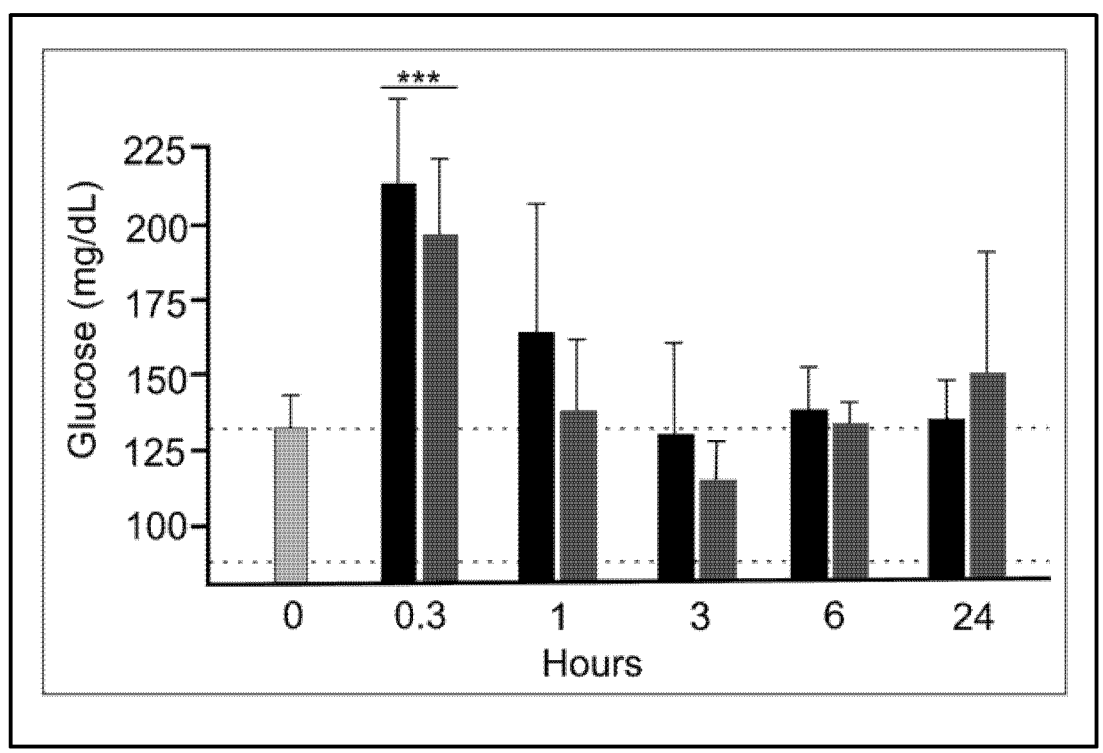
FIG. 3. Nose to brain IGF-1 did not cause hypoglycemia. Non-fasted rats (day time; n=4/group) were anesthetized with isoflurane and tail samples taken for blood glucose analysis using a Bayer Contour Next EZ glucometer (0 hr time). Animals were then treated with intra-nasal succinate buffer (black) or IGF-1 (red) over 20 minutes. As expected, glucose rose at the conclusion of treatments due to continued isoflurane. However, no significant differences were seen with treatment pairs (t-test) or 0 time (gray) versus other values when compared via ANOVA plus post hoc Holm-Sidak except at the 0.3 hr point (*p<0.001). The lowest IGF-1 glucose-related level seen was 114 mg/dL [compared to control (132 mg/dL; time 0)], which is within the normal range for Wistar rats [85-132 mg/dL (Kohn D F and Clifford C B, 2002)]. Dotted lines show normal glucose range. While the glucose level that defines hypoglycemia is variable, a drop of 1 mM is not considered hypoglycemic. Furthermore, no IGF-1-glucose level was hypoglycemic. Results shown as mean±SD.

Insulin-like growth factor 1 (IGF-1) is also known as somatomedin C or mechano growth factor, and has also been referred to as a "sulfation factor" or "nonsuppressible insulin-like activity" (NSILA). The insulin-like growth factor family includes two ligands, IGF-1 and IGF-2, two cell membrane receptors, IGF-1R and IGF-2R, and six IGF-1-binding proteins IGFBP1-6. In humans, the IGF-1 protein is encoded by the IGF1 gene. Insulin-like growth factor 1 has been shown to interact with the IGF-1 receptor (IGF1R), and the insulin receptor.

An example of an IGF-1 amino acid sequence is found in GenBank accession number CAA01955: MALCLLTFTS-SATAGPETLCGAEL-VDALQFVCGDRGFYFNKPTGYGSSSRRAPQTGI VDECCFRSCDLRRLEMYCA-PLKPAKSARSVRAQRHTDMPKTQKEVHLKNAS-RGSA GNKNYRM (SEQ ID NO:1). A further example of an IGF-1 amino acid sequence comprises MGPETLC-GAELVDALQFVCGDRGFYFNKPTGYGSSSRRA-PQTGMVDECCFRSCDLR RLEMYCAPLKPAKSA (SEQ ID NO:2). A further example of IGF-1 includes a polypeptide comprising the following sequence: GPETLCGAEL-VDALQFVCGDRGFYFNKPTGYGSSSRRAPQTGIV-DECCFRSCDLRRL EMYCAPLKPAKSA (SEQ ID NO:5). Certain aspects are directed to isoforms and variants of IGF-1 that retain one or more functions of IGF-1, particularly the therapeutic effects described herein.

Insulin is a hormone central to regulating carbohydrate and fat metabolism in the body. Insulin is synthesized in the pancreas within the β-cells of the islets of Langerhans. Insulin has also been shown to be produced within the brain. The proinsulin precursor of insulin is encoded by the INS gene. Insulin has been shown to interact with the insulin receptor. An example of an insulin amino acid sequence is found in GenBank accession number AAA59172: MALWMRLLPLLALLALWGPDPAAAF- VNQHLCGSHLVEALYLVCGERGFFYTPKTR REAE-
DLQVGQVELGGGPGAGSLQPLALEGSLQKR-
GIVEQCCTSICSLYQLENYCN (SEQ ID NO:3) and
GenBank accession number AAA59179:

```
                                              (SEQ ID NO: 4)
MALWMRLLPLLALLALWGPDPAAAFVNQHLCGSHLVEALYLVCGERGFFY

TPKTRREAEVGQVELGGGPGAGSLQPLALEGSLQKRGIVEQCCTSICSLY

QLENYCN.
```

Certain aspects are directed to isoforms and variants of insulin that retain one or more functions of insulin, particularly the therapeutic effects described herein. Insulin peptides or polypeptides can comprise all or part of an amino acid sequence similar to that provided in SEQ ID NO:3 or 4.

II. Antibodies

Aspects of the disclosure relate to antibodies comprising a heavy and/or light chain of a CGRP antibody, or fragments thereof. The term "antibody" refers to an intact immunoglobulin of any isotype, or a fragment thereof that can compete with the intact antibody for specific binding to the target antigen, and includes chimeric, humanized, fully human, and bispecific antibodies. As used herein, the terms "antibody" or "immunoglobulin" are used interchangeably and refer to any of several classes of structurally related proteins that function as part of the immune response of an animal, including IgG, IgD, IgE, IgA, IgM, and related proteins, as well as polypeptides comprising antibody CDR domains that retain antigen-binding activity.

The term "antigen" refers to a molecule or a portion of a molecule capable of being bound by a selective binding agent, such as an antibody. An antigen may possess one or more epitopes that are capable of interacting with different antibodies.

The term "epitope" includes any region or portion of molecule capable eliciting an immune response by binding to an immunoglobulin or to a T-cell receptor. Epitope determinants may include chemically active surface groups such as amino acids, sugar side chains, phosphoryl or sulfonyl groups, and may have specific three-dimensional structural characteristics and/or specific charge characteristics. Generally, antibodies specific for a particular target antigen will preferentially recognize an epitope on the target antigen within a complex mixture.

The epitope regions of a given polypeptide can be identified using many different epitope mapping techniques are well known in the art, including: x-ray crystallography, nuclear magnetic resonance spectroscopy, site-directed mutagenesis mapping, protein display arrays, see, e.g., Epitope Mapping Protocols, (Johan Rockberg and Johan Nilvebrant, Ed., 2018) Humana Press, New York, N.Y. Such techniques are known in the art and described in, e.g., U.S. Pat. No. 4,708,871; Geysen et al. Proc. Natl. Acad. Sci. USA 81:3998-4002 (1984); Geysen et al. Proc. Natl. Acad. Sci. USA 82:178-182 (1985); Geysen et al. Molec. Immunol. 23:709-715 (1986). Additionally, antigenic regions of proteins can also be predicted and identified using standard antigenicity and hydropathy plots.

The term "immunogenic sequence" means a molecule that includes an amino acid sequence of at least one epitope such that the molecule is capable of stimulating the production of antibodies in an appropriate host. The term "immunogenic composition" means a composition that comprises at least one immunogenic molecule (e.g., an antigen or carbohydrate).

An intact antibody is generally composed of two full-length heavy chains and two full-length light chains, but in some instances may include fewer chains, such as antibodies naturally occurring in camelids that may comprise only heavy chains. Antibodies as disclosed herein may be derived solely from a single source or may be "chimeric," that is, different portions of the antibody may be derived from two different antibodies. For example, the variable or CDR regions may be derived from a rat or murine source, while the constant region is derived from a different animal source, such as a human. The antibodies or binding fragments may be produced in hybridomas, by recombinant DNA techniques, or by enzymatic or chemical cleavage of intact antibodies. Unless otherwise indicated, the term "antibody" includes derivatives, variants, fragments, and muteins thereof, examples of which are described below (Sela-Culang et al., Front Immunol. 2013; 4: 302; 2013).

The term "light chain" includes a full-length light chain and fragments thereof having sufficient variable region sequence to confer binding specificity. A full-length light chain has a molecular weight of around 25,000 Daltons and includes a variable region domain (abbreviated herein as VL), and a constant region domain (abbreviated herein as CL). There are two classifications of light chains, identified as kappa (?) and lambda (?). The term "VL fragment" means a fragment of the light chain of a monoclonal antibody that includes all or part of the light chain variable region, including CDRs. A VL fragment can further include light chain constant region sequences. The variable region domain of the light chain is at the amino-terminus of the polypeptide.

The term "heavy chain" includes a full-length heavy chain and fragments thereof having sufficient variable region sequence to confer binding specificity. A full-length heavy chain has a molecular weight of around 50,000 Daltons and includes a variable region domain (abbreviated herein as VH), and three constant region domains (abbreviated herein as CH1, CH2, and CH3). The term "VH fragment" means a fragment of the heavy chain of a monoclonal antibody that includes all or part of the heavy chain variable region, including CDRs. A VH fragment can further include heavy chain constant region sequences. The number of heavy chain constant region domains will depend on the isotype. The VH domain is at the amino-terminus of the polypeptide, and the CH domains are at the carboxy-terminus, with the CH3 being closest to the —COOH end. The isotype of an antibody can be IgM, IgD, IgG, IgA, or IgE and is defined by the heavy chains present of which there are five classifications: mu (μ), delta (d), gamma (?), alpha (a), or epsilon (e) chains, respectively. IgG has several subtypes, including, but not limited to, IgG1, IgG2, IgG3, and IgG4. IgM subtypes include IgM1 and IgM2. IgA subtypes include IgA1 and IgA2.

A. Types of Antibodies

Antibodies can be whole immunoglobulins of any isotype or classification, chimeric antibodies, or hybrid antibodies with specificity to two or more antigens. They may also be fragments (e.g., F(ab')2, Fab', Fab, Fv, and the like), including hybrid fragments. An immunoglobulin also includes natural, synthetic, or genetically engineered proteins that act like an antibody by binding to specific antigens to form a complex. The term antibody includes genetically engineered or otherwise modified forms of immunoglobulins.

The term "monomer" means an antibody containing only one Ig unit. Monomers are the basic functional units of antibodies. The term "dimer" means an antibody containing two Ig units attached to one another via constant domains of the antibody heavy chains (the Fc, or fragment crystallizable, region). The complex may be stabilized by a joining (J) chain protein. The term "multimer" means an antibody containing more than two Ig units attached to one another via constant domains of the antibody heavy chains (the Fc region). The complex may be stabilized by a joining (J) chain protein.

The term "bivalent antibody" means an antibody that comprises two antigen-binding sites. The two binding sites may have the same antigen specificities or they may be bispecific, meaning the two antigen-binding sites have different antigen specificities.

Bispecific antibodies are a class of antibodies that have two paratopes with different binding sites for two or more distinct epitopes. In some embodiments, bispecific antibodies can be biparatopic, wherein a bispecific antibody may specifically recognize a different epitope from the same antigen. In some embodiments, bispecific antibodies can be constructed from a pair of different single domain antibodies termed "nanobodies". Single domain antibodies are sourced and modified from cartilaginous fish and camelids. Nanobodies can be joined together by a linker using techniques typical to a person skilled in the art; such methods for selection and joining of nanobodies are described in PCT Publication No. WO2015044386A1, No. WO2010037838A2, and Bever et al., Anal Chem. 86:7875-7882 (2014), each of which are specifically incorporated herein by reference in their entirety.

Bispecific antibodies can be constructed as: a whole IgG, Fab'2, Fab'PEG, a diabody, or alternatively as scFv. Diabodies and scFvs can be constructed without an Fc region, using only variable domains, potentially reducing the effects of anti-idiotypic reaction. Bispecific antibodies may be produced by a variety of methods including, but not limited to, fusion of hybridomas or linking of Fab' fragments. See, e.g., Songsivilai and Lachmann, Clin. Exp. Immunol. 79:315-321 (1990); Kostelny et al., J. Immunol. 148:1547-1553 (1992), each of which are specifically incorporated by reference in their entirety.

In certain aspects, the antigen-binding domain may be multispecific or heterospecific by multimerizing with VH and VL region pairs that bind a different antigen. For example, the antibody may bind to, or interact with, (a) a cell surface antigen, (b) an Fc receptor on the surface of an effector cell, or (c) at least one other component. Accordingly, aspects may include, but are not limited to, bispecific, trispecific, tetraspecific, and other multispecific antibodies or antigen-binding fragments thereof that are directed to epitopes and to other targets, such as Fc receptors on effector cells.

In some embodiments, multispecific antibodies can be used and directly linked via a short flexible polypeptide chain, using routine methods known in the art. One such example is diabodies that are bivalent, bispecific antibodies in which the VH and VL domains are expressed on a single polypeptide chain, and utilize a linker that is too short to allow for pairing between domains on the same chain, thereby forcing the domains to pair with complementary domains of another chain creating two antigen binding sites. The linker functionality is applicable for embodiments of triabodies, tetrabodies, and higher order antibody multimers.

(see, e.g., Hollinger et al., Proc Natl. Acad. Sci. USA 90:6444-6448 (1993); Polijak et al., Structure 2:1121-1123 (1994); Todorovska et al., J. Immunol. Methods 248:47-66 (2001)).

Bispecific diabodies, as opposed to bispecific whole antibodies, may also be advantageous because they can be readily constructed and expressed in E. coli. Diabodies (and other polypeptides such as antibody fragments) of appropriate binding specificities can be readily selected using phage display (WO94/13804) from libraries. If one arm of the diabody is kept constant, for instance, with a specificity directed against a protein, then a library can be made where the other arm is varied and an antibody of appropriate specificity selected. Bispecific whole antibodies may be made by alternative engineering methods as described in Ridgeway et al., (Protein Eng., 9:616-621, 1996) and Krah et al., (N Biotechnol. 39:167-173, 2017), each of which is hereby incorporated by reference in their entirety.

Heteroconjugate antibodies are composed of two covalently linked monoclonal antibodies with different specificities. See, e.g., U.S. Pat. No. 6,010,902, incorporated herein by reference in its entirety.

The part of the Fv fragment of an antibody molecule that binds with high specificity to the epitope of the antigen is referred to herein as the "paratope." The paratope consists of the amino acid residues that make contact with the epitope of an antigen to facilitate antigen recognition. Each of the two Fv fragments of an antibody is composed of the two variable domains, VH and VL, in dimerized configuration. The primary structure of each of the variable domains includes three hypervariable loops separated by, and flanked by, Framework Regions (FR). The hypervariable loops are the regions of highest primary sequences variability among the antibody molecules from any mammal. The term hypervariable loop is sometimes used interchangeably with the term "Complementarity Determining Region (CDR)." The length of the hypervariable loops (or CDRs) varies between antibody molecules. The framework regions of all antibody molecules from a given mammal have high primary sequence similarity/consensus. The consensus of framework regions can be used by one skilled in the art to identify both the framework regions and the hypervariable loops (or CDRs) which are interspersed among the framework regions. The hypervariable loops are given identifying names which distinguish their position within the polypeptide, and on which domain they occur. CDRs in the VL domain are identified as L1, L2, and L3, with L1 occurring at the most distal end and L3 occurring closest to the CL domain. The CDRs may also be given the names CDR-1, CDR-2, and CDR-3. The L3 (CDR-3) is generally the region of highest variability among all antibody molecules produced by a given organism. The CDRs are regions of the polypeptide chain arranged linearly in the primary structure, and separated from each other by Framework Regions. The amino terminal (N-terminal) end of the VL chain is named FR1. The region identified as FR2 occurs between L1 and L2 hypervariable loops. FR3 occurs between L2 and L3 hypervariable loops, and the FR4 region is closest to the CL domain. This structure and nomenclature is repeated for the VH chain, which includes three CDRs identified as H1, H2 and H3. The majority of amino acid residues in the variable domains, or Fv fragments (VH and VL), are part of the framework regions (approximately 85%). The three dimensional, or tertiary, structure of an antibody molecule is such that the framework regions are more internal to the molecule and provide the majority of the structure, with the CDRs on the external surface of the molecule.

Several methods have been developed and can be used by one skilled in the art to identify the exact amino acids that constitute each of these regions. This can be done using any of a number of multiple sequence alignment methods and algorithms, which identify the conserved amino acid residues that make up the framework regions, therefore identifying the CDRs that may vary in length but are located between framework regions. Three commonly used methods have been developed for identification of the CDRs of antibodies: Kabat (as described in T. T. Wu and E. A. Kabat, "AN ANALYSIS OF THE SEQUENCES OF THE VARIABLE REGIONS OF BENCE JONES PROTEINS AND MYELOMA LIGHT CHAINS AND THEIR IMPLICATIONS FOR ANTIBODY COMPLEMENTARITY," J Exp Med, vol. 132, no. 2, pp. 211-250, August 1970); Chothia (as described in C. Chothia et al., "Conformations of immunoglobulin hypervariable regions," Nature, vol. 342, no. 6252, pp. 877-883, December 1989); and IMGT (as described in M.-P. Lefranc et al., "IMGT unique numbering for immunoglobulin and T cell receptor variable domains and Ig superfamily V-like domains," Developmental & Comparative Immunology, vol. 27, no. 1, pp. 55-77, January 2003). These methods each include unique numbering systems for the identification of the amino acid residues that constitute the variable regions. In most antibody molecules, the amino acid residues that actually contact the epitope of the antigen occur in the CDRs, although in some cases, residues within the framework regions contribute to antigen binding.

One skilled in the art can use any of several methods to determine the paratope of an antibody. These methods include:

1) Computational predictions of the tertiary structure of the antibody/epitope binding interactions based on the chemical nature of the amino acid sequence of the antibody variable region and composition of the epitope.

2) Hydrogen-deuterium exchange and mass spectroscopy

3) Polypeptide fragmentation and peptide mapping approaches in which one generates multiple overlapping peptide fragments from the full length of the polypeptide and evaluates the binding affinity of these peptides for the epitope.

4) Antibody Phage Display Library analysis in which the antibody Fab fragment encoding genes of the mammal are expressed by bacteriophage in such a way as to be incorporated into the coat of the phage. This population of Fab expressing phage are then allowed to interact with the antigen which has been immobilized or may be expressed in by a different exogenous expression system. Non-binding Fab fragments are washed away, thereby leaving only the specific binding Fab fragments attached to the antigen. The binding Fab fragments can be readily isolated and the genes which encode them determined. This approach can also be used for smaller regions of the Fab fragment including Fv fragments or specific VH and VL domains as appropriate.

In certain aspects, affinity matured antibodies are enhanced with one or more modifications in one or more CDRs thereof that result in an improvement in the affinity of the antibody for a target antigen as compared to a parent antibody that does not possess those alteration(s). Certain affinity matured antibodies will have nanomolar or picomolar affinities for the target antigen. Affinity matured antibodies are produced by procedures known in the art, e.g., Marks et al., Bio/Technology 10:779 (1992) describes affinity maturation by VH and VL domain shuffling, random mutagenesis of CDR and/or framework residues employed in phage display is described by Rajpal et al., PNAS. 24: 8466-8471 (2005) and Thie et al., Methods Mol Biol. 525:309-22 (2009) in conjugation with computation methods as demonstrated in Tiller et al., Front. Immunol. 8:986 (2017).

Chimeric immunoglobulins are the products of fused genes derived from different species; "humanized" chimeras generally have the framework region (FR) from human immunoglobulins and one or more CDRs are from a non-human source.

In certain aspects, portions of the heavy and/or light chain are identical or homologous to corresponding sequences from another particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity. U.S. Pat. No. 4,816,567; and Morrison et al., Proc. Natl. Acad. Sci. USA 81:6851 (1984). For methods relating to chimeric antibodies, see, e.g., U.S. Pat. No. 4,816,567; and Morrison et al., Proc. Natl. Acad. Sci. USA 81:6851-6855 (1985), each of which are specifically incorporated herein by reference in their entirety. CDR grafting is described, for example, in U.S. Pat. Nos. 6,180, 370, 5,693,762, 5,693,761, 5,585,089, and 5,530,101, which are all hereby incorporated by reference for all purposes.

In some embodiments, minimizing the antibody polypeptide sequence from the non-human species optimizes chimeric antibody function and reduces immunogenicity. Specific amino acid residues from non-antigen recognizing regions of the non-human antibody are modified to be homologous to corresponding residues in a human antibody or isotype. One example is the "CDR-grafted" antibody, in which an antibody comprises one or more CDRs from a particular species or belonging to a specific antibody class or subclass, while the remainder of the antibody chain(s) is identical or homologous to a corresponding sequence in antibodies derived from another species or belonging to another antibody class or subclass. For use in humans, the V region composed of CDR1, CDR2, and partial CDR3 for both the light and heavy chain variance region from a non-human immunoglobulin, are grafted with a human antibody framework region, replacing the naturally occurring antigen receptors of the human antibody with the non-human CDRs. In some instances, corresponding non-human residues replace framework region residues of the human immunoglobulin. Furthermore, humanized antibodies may comprise residues that are not found in the recipient antibody or in the donor antibody to further refine performance. The humanized antibody may also comprise at least a portion of an immunoglobulin constant region (Fc), typically that of a human immunoglobulin. See, e.g., Jones et al., Nature 321:522 (1986); Riechmann et al., Nature 332:323 (1988); Presta, Curr. Op. Struct. Biol. 2:593 (1992); Vaswani and Hamilton, Ann. Allergy, Asthma and Immunol. 1:105 (1998); Harris, Biochem. Soc. Transactions 23; 1035 (1995); Hurle and Gross, Curr. Op. Biotech. 5:428 (1994); Verhoeyen et al., Science 239:1534-36 (1988).

Intrabodies are intracellularly localized immunoglobulins that bind to intracellular antigens as opposed to secreted antibodies, which bind antigens in the extracellular space.

Polyclonal antibody preparations typically include different antibodies against different determinants (epitopes). In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies or "mAb" refer to an antibody obtained from a population of homogeneous antibodies from an exclusive parental cell, e.g., the population is identical except for naturally occurring mutations that may be present in minor amounts. Each monoclonal antibody is directed against a single antigenic determinant.

B. Functional Antibody Fragments and Antigen-Binding Fragments

1. Antigen-Binding Fragments

Certain aspects relate to antibody fragments, such as antibody fragments that bind to antigen. The term functional antibody fragment includes antigen-binding fragments of an antibody that retain the ability to specifically bind to an antigen. These fragments are constituted of various arrangements of the variable region heavy chain (VH) and/or light chain (VL); and in some embodiments, include constant region heavy chain 1 (CH1) and light chain (CL). In some embodiments, they lack the Fc region constituted of heavy chain 2 (CH2) and 3 (CH3) domains. Embodiments of antigen binding fragments and the modifications thereof may include: (i) the Fab fragment type constituted with the VL, VH, CL, and CH1 domains; (ii) the Fd fragment type constituted with the VH and CH1 domains; (iii) the Fv fragment type constituted with the VH and VL domains; (iv) the single domain fragment type, dAb, (Ward, 1989; McCafferty et al., 1990; Holt et al., 2003) constituted with a single VH or VL domain; (v) isolated complementarity determining region (CDR) regions. Such terms are described, for example, in Harlow and Lane, Antibodies: A Laboratory Manual, Cold Spring Harbor Laboratory, NY (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, 2d ed., Wiley-Liss, Inc. New York, N.Y. (1990); Antibodies, 4:259-277 (2015), each of which are incorporated by reference.

Antigen-binding fragments also include fragments of an antibody that retain exactly, at least, or at most 1, 2, or 3 complementarity determining regions (CDRs) from a light chain variable region. Fusions of CDR-containing sequences to an Fc region (or a CH2 or CH3 region thereof) are included within the scope of this definition including, for example, scFv fused, directly or indirectly, to an Fc region are included herein.

The term Fab fragment means a monovalent antigen-binding fragment of an antibody containing the VL, VH, CL and CH1 domains. The term Fab' fragment means a monovalent antigen-binding fragment of a monoclonal antibody that is larger than a Fab fragment. For example, a Fab' fragment includes the VL, VH, CL and CH1 domains and all or part of the hinge region. The term F(ab')2 fragment means a bivalent antigen-binding fragment of a monoclonal antibody comprising two Fab' fragments linked by a disulfide bridge at the hinge region. An F(ab')2 fragment includes, for example, all or part of the two VH and VL domains, and can further include all or part of the two CL and CH1 domains.

The term Fd fragment means a fragment of the heavy chain of a monoclonal antibody, which includes all or part of the VH, including the CDRs. An Fd fragment can further include CH1 region sequences.

The term Fv fragment means a monovalent antigen-binding fragment of a monoclonal antibody, including all or part of the VL and VH, and absent of the CL and CH1 domains. The VL and VH include, for example, the CDRs. Single-chain antibodies (sFv or scFv) are Fv molecules in which the VL and VH regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference. The term (scFv)2 means bivalent or bispecific sFv polypeptide chains that include oligomerization domains at their C-termini, separated from the sFv by a hinge region (Pack et al. 1992). The oligomerization domain comprises self-associating a-helices, e.g., leucine zippers, which can be further stabilized by additional disulfide bonds. (scFv)2 fragments are also known as "miniantibodies" or "minibodies."

single domain antibody is an antigen-binding fragment containing only a VH or the VL domain. In some instances, two or more VH regions are covalently joined with a peptide linker to create a bivalent domain antibody. The two VH regions of a bivalent domain antibody may target the same or different antigens.

2. Fragment Crystallizable Region, Fc

An Fc region contains two heavy chain fragments comprising the CH2 and CH3 domains of an antibody. The two heavy chain fragments are held together by two or more disulfide bonds and by hydrophobic interactions of the CH3 domains. The term "Fc polypeptide" as used herein includes native and mutein forms of polypeptides derived from the Fc region of an antibody. Truncated forms of such polypeptides containing the hinge region that promotes dimerization are included.

C. Polypeptides with Antibody CDRs & Scaffolding Domains that Display the CDRs Antigen-binding peptide scaffolds, such as complementarity-determining regions (CDRs), are used to generate protein-binding molecules in accordance with the embodiments. Generally, a person skilled in the art can determine the type of protein scaffold on which to graft at least one of the CDRs. It is known that scaffolds, optimally, must meet a number of criteria such as: good phylogenetic conservation; known three-dimensional structure; small size; few or no post-transcriptional modifications; and/or be easy to produce, express, and purify. Skerra, J Mol Recognit, 13:167-87 (2000).

The protein scaffolds can be sourced from, but not limited to: fibronectin type III FN3 domain (known as "monobodies"), fibronectin type III domain 10, lipocalin, anticalin, Z-domain of protein A of *Staphylococcus aureus*, thioredoxin A or proteins with a repeated motif such as the "ankyrin repeat", the "armadillo repeat", the "leucine-rich repeat" and the "tetratricopeptide repeat". Such proteins are described in US Patent Publication Nos. 2010/0285564, 2006/0058510, 2006/0088908, 2005/0106660, and PCT Publication No. WO2006/056464, each of which are specifically incorporated herein by reference in their entirety. Scaffolds derived from toxins from scorpions, insects, plants, mollusks, etc., and the protein inhibiters of neuronal NO synthase (PIN) may also be used.

D. Antibody Binding

The term "selective binding agent" refers to a molecule that binds to an antigen. Non-limiting examples include antibodies, antigen-binding fragments, scFv, Fab, Fab', F(ab')2, single chain antibodies, peptides, peptide fragments and proteins.

The term "binding" refers to a direct association between two molecules, due to, for example, covalent, electrostatic, hydrophobic, and ionic and/or hydrogen-bond interactions, including interactions such as salt bridges and water bridges. "Immunologically reactive" means that the selective binding agent or antibody of interest will bind with antigens present in a biological sample. The term "immune complex" refers the combination formed when an antibody or selective binding agent binds to an epitope on an antigen.

1. Affinity/Avidity

The term "affinity" refers the strength with which an antibody or selective binding agent binds an epitope. In antibody binding reactions, this is expressed as the affinity constant (Ka or ka sometimes referred to as the association constant) for any given antibody or selective binding agent. Affinity is measured as a comparison of the binding strength of the antibody to its antigen relative to the binding strength of the antibody to an unrelated amino acid sequence. Affinity can be expressed as, for example, 20-fold greater binding ability of the antibody to its antigen then to an unrelated amino acid sequence. As used herein, the term "avidity" refers to the resistance of a complex of two or more agents to dissociation after dilution. The terms "immunoreactive" and "preferentially binds" are used interchangeably herein with respect to antibodies and/or selective binding agent.

There are several experimental methods that can be used by one skilled in the art to evaluate the binding affinity of any given antibody or selective binding agent for its antigen. This is generally done by measuring the equilibrium dissociation constant (KD or Kd), using the equation KD=koff/kon=[A][B]/[AB]. The term koff is the rate of dissociation between the antibody and antigen per unit time, and is related to the concentration of antibody and antigen present in solution in the unbound form at equilibrium. The term kon is the rate of antibody and antigen association per unit time, and is related to the concentration of the bound antigen-antibody complex at equilibrium. The units used for measuring the KD are mol/L (molarity, or M), or concentration. The Ka of an antibody is the opposite of the KD, and is determined by the equation Ka=1/KD. Examples of some experimental methods that can be used to determine the KD value are: enzyme-linked immunosorbent assays (ELISA), isothermal titration calorimetry (ITC), fluorescence anisotropy, surface plasmon resonance (SPR), and affinity capillary electrophoresis (ACE). The affinity constant (Ka) of an antibody is the opposite of the KD, and is determined by the equation Ka=1/KD.

Antibodies deemed useful in certain embodiments may have an affinity constant (Ka) of about, at least about, or at most about 106, 107, 108, 109, or 1010 M or any range derivable therein. Similarly, in some embodiments, antibodies may have a dissociation constant of about, at least about or at most about 10-6, 10-7, 10-8, 10-9, 10-10 M, or any range derivable therein. These values are reported for antibodies discussed herein and the same assay may be used to evaluate the binding properties of such antibodies. An antibody of the invention is said to "specifically bind" its target antigen when the dissociation constant (KD) is ?10-8 M. The antibody specifically binds antigen with "high affinity" when the KD is ?5×10-9 M, and with "very high affinity" when the KD is ?5×10-10 M.

2. Epitope Specificity

The epitope of an antigen is the specific region of the antigen for which an antibody has binding affinity. In the case of protein or polypeptide antigens, the epitope is the specific residues (or specified amino acids or protein segment) that the antibody binds with high affinity. An antibody does not necessarily contact every residue within the protein. Nor does every single amino acid substitution or deletion within a protein necessarily affect binding affinity. For purposes of this specification and the accompanying claims, the terms "epitope" and "antigenic determinant" are used interchangeably to refer to the site on an antigen to which B and/or T cells respond or recognize. Polypeptide epitopes can be formed from both contiguous amino acids and noncontiguous amino acids juxtaposed by tertiary folding of a polypeptide. An epitope typically includes at least 3, and typically 5-10 amino acids in a unique spatial conformation.

Epitope specificity of an antibody can be determined in a variety of ways. One approach, for example, involves testing a collection of overlapping peptides of about 15 amino acids spanning the full sequence of the protein and differing in increments of a small number of amino acids (e.g., 3 to 30 amino acids). The peptides are immobilized in separate wells of a microtiter dish. Immobilization can be accomplished, for example, by biotinylating one terminus of the peptides. This process may affect the antibody affinity for the epitope, therefore different samples of the same peptide can be biotinylated at the N and C terminus and immobilized in separate wells for the purposes of comparison. This is useful for identifying end-specific antibodies. Optionally, additional peptides can be included terminating at a particular amino acid of interest. This approach is useful for identifying end-specific antibodies to internal fragments. An antibody or antigen-binding fragment is screened for binding to each of the various peptides. The epitope is defined as a segment of amino acids that is common to all peptides to which the antibody shows high affinity binding.

3. Modification of Antibody Antigen-Binding Domains

It is understood that the antibodies of the present invention may be modified, such that they are substantially identical to the antibody polypeptide sequences, or fragments thereof, and still bind the epitopes of the present invention. Polypeptide sequences are "substantially identical" when optimally aligned using such programs as Clustal Omega, IGBLAST, GAP or BESTFIT using default gap weights, they share at least 80% sequence identity, at least 90% sequence identity, at least 95% sequence identity, at least 96% sequence identity, at least 97% sequence identity, at least 98% sequence identity, or at least 99% sequence identity or any range therein.

As discussed herein, minor variations in the amino acid sequences of antibodies or antigen-binding regions thereof are contemplated as being encompassed by the present invention, providing that the variations in the amino acid sequence maintain at least 75%, more preferably at least 80%, at least 90%, at least 95%, at least 96%, at least 97%, at least 98% and most preferably at least 99% sequence identity. In particular, conservative amino acid replacements are contemplated.

Conservative replacements are those that take place within a family of amino acids that are related in their side chains. Genetically encoded amino acids are generally divided into families based on the chemical nature of the side chain; e.g., acidic (aspartate, glutamate), basic (lysine, arginine, histidine), nonpolar (alanine, valine, leucine, isoleucine, proline, phenylalanine, methionine, tryptophan), and uncharged polar (glycine, asparagine, glutamine, cysteine, serine, threonine, tyrosine). For example, it is reasonable to expect that an isolated replacement of a leucine moiety with an isoleucine or valine moiety, or a similar replacement of an amino acid with a structurally related amino acid in the same family, will not have a major effect on the binding or properties of the resulting molecule, especially if the replacement does not involve an amino acid within a framework site. Whether an amino acid change results in a functional peptide can readily be determined by assaying the specific activity of the polypeptide derivative. Standard ELISA, Surface Plasmon Resonance (SPR), or other antibody binding assays can be performed by one skilled in the art to make a quantitative comparison of antigen binging affinity between the unmodified antibody and any polypeptide derivatives with conservative substitutions generated through any of several methods available to one skilled in the art.

Fragments or analogs of antibodies or immunoglobulin molecules can be readily prepared by those skilled in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Standard methods to identify protein sequences that fold into a known three-dimensional structure are available to those skilled in the art; Dill and McCallum., Science 338:1042-1046 (2012). Several algorithms for predicting protein structures and the gene sequences that encode these have been developed, and many of these algorithms can be found at the National Center for Biotechnology Information (on the World Wide Web at ncbi.nlm.nih.gov/guide/proteins/) and at the Bioinformatics Resource Portal (on the World Wide Web at expasy.org/proteomics). Thus, the foregoing examples demonstrate that those of skill in the art can recognize sequence motifs and structural conformations that may be used to define structural and functional domains in accordance with the invention.

Framework modifications can be made to antibodies to decrease immunogenicity, for example, by "backmutating" one or more framework residues to a corresponding germline sequence.

It is also contemplated that the antigen-binding domain may be multi-specific or multivalent by multimerizing the antigen-binding domain with VH and VL region pairs that bind either the same antigen (multi-valent) or a different antigen (multi-specific).

E. Chemical Modification of Antibodies

In some aspects, also contemplated are glycosylation variants of antibodies, wherein the number and/or type of glycosylation site(s) has been altered compared to the amino acid sequences of the parent polypeptide. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861). In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked glycosylation sites are created. Antibodies typically have an N-linked glycosylation site in the Fc region.

Additional antibody variants include cysteine variants, wherein one or more cysteine residues in the parent or native amino acid sequence are deleted from or substituted with another amino acid (e.g., serine). Cysteine variants are useful, inter alia, when antibodies must be refolded into a biologically active conformation. Cysteine variants may have fewer cysteine residues than the native antibody and typically have an even number to minimize interactions resulting from unpaired cysteines.

In some aspects, the polypeptides can be pegylated to increase biological half-life by reacting the polypeptide with polyethylene glycol (PEG) or a reactive ester or aldehyde derivative of PEG, under conditions in which one or more PEG groups become attached to the polypeptide. Polypeptide pegylation may be carried out by an acylation reaction or an alkylation reaction with a reactive PEG molecule (or an analogous reactive water-soluble polymer). Methods for pegylating proteins are known in the art and can be applied to the polypeptides of the invention to obtain PEGylated derivatives of antibodies. See, e.g., EP 0 154 316 and EP 0 401 384. In some aspects, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols, and polyvinyl alcohols. As used herein, the term "polyethylene glycol" is intended to encompass any of the forms of PEG that have been used to derivatized other proteins.

1. Conjugation

Derivatives of the antibodies and antigen binding fragments that are described herein are also provided. The derivatized antibody or fragment thereof may comprise any molecule or substance that imparts a desired property to the antibody or fragment. The derivatized antibody can comprise, for example, a detectable (or labeling) moiety (e.g., a radioactive, colorimetric, antigenic, or enzymatic molecule, or a detectable bead), a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses).

Optionally, an antibody or an immunological portion of an antibody can be chemically conjugated to, or expressed as, a fusion protein with other proteins. In some aspects, polypeptides may be chemically modified by conjugating or fusing the polypeptide to serum protein, such as human serum albumin, to increase half-life of the resulting molecule. See, e.g., EP 0322094 and EP 0 486 525. In some aspects, the polypeptides may be conjugated to a diagnostic agent and used diagnostically, for example, to monitor the development or progression of a disease and determine the efficacy of a given treatment regimen. In some aspects, the polypeptides may also be conjugated to a therapeutic agent to provide a therapy in combination with the therapeutic effect of the polypeptide. Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. The functional nucleic acid molecules may act as effectors, inhibitors, modulators, and stimulators of a specific activity possessed by a target molecule, or the functional nucleic acid molecules may possess a de novo activity independent of any other molecules.

In some aspects, disclosed are antibodies and antibody-like molecules that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules include toxins, therapeutic enzymes, antibiotics, radiolabeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles, or ligands.

2. Conjugate Types

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to be detected, and/or further quantified if desired. Examples of detectable labels include, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, streptavidin or haptens) and the like. Particular examples of labels are, but not limited to, horseradish peroxidase (HRP), fluorescein, FITC, rhodamine, dansyl, umbelliferone, dimethyl acridinium ester (DMAE), Texas red, luminol, NADPH and a- or β-galactosidase. Antibody conjugates include those intended primarily for use in vitro, where the antibody is linked to a secondary binding ligand and/or to an enzyme to generate a colored product upon contact with a chromogenic substrate. Examples of suitable enzymes include, but are not limited to, urease, alkaline phosphatase, (horseradish) hydrogen peroxidase, or glucose oxidase. Preferred secondary binding ligands are biotin and/or avidin and streptavidin compounds. The uses of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference. Molecules containing azido groups may also be used to form covalent bonds to proteins through reactive nitrene intermediates that are generated by low intensity ultraviolet light (Potter & Haley, 1983).

In some aspects, contemplated are immunoconjugates comprising an antibody or antigen-binding fragment thereof conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In this way, the agent of interest can be targeted directly to cells bearing cell surface antigen. The antibody and agent may be associated through non-covalent interactions such as through electrostatic forces, or by covalent bonds. Various linkers, known in the art, can be employed in order to form the immunoconjugate. Additionally, the immunoconjugate can be provided in the form of a fusion protein. In one aspect, an antibody may be conjugated to various therapeutic substances in order to target the cell surface antigen. Examples of conjugated agents include, but are not limited to, metal chelate complexes, drugs, toxins and other effector molecules, such as cytokines, lymphokines, chemokines, immunomodulators, radiosensitizers, asparaginase, carboranes, and radioactive halogens.

In antibody drug conjugates (ADC), an antibody (Ab) is conjugated to one or more drug moieties (D) through a linker (L). The ADC may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Antibody drug conjugates may also be produced by modification of the antibody to introduce electrophilic moieties, which can react with nucleophilic substituents on the linker reagent or drug. Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another aspect, the antibody may be conjugated to a "receptor" (such as streptavidin) for utilization in tumor or cancer cell pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Examples of an antibody-drug conjugates known to a person skilled in the art are pro-drugs useful for the local delivery of cytotoxic or cytostatic agents, i.e. drugs to kill or inhibit tumor cells in the treatment of cancer (Syrigos and Epenetos, Anticancer Res. 19:605-614 (1999); Niculescu-Duvaz and Springer, Adv. Drg. Del. Rev. 26:151-172 (1997); U.S. Pat. No. 4,975,278). In contrast, systematic administration of these unconjugated drug agents may result in unacceptable levels of toxicity to normal cells as well as the target tumor cells (Baldwin et al., Lancet 1:603-5 (1986); Thorpe, (1985) "Antibody Carriers of Cytotoxic Agents in Cancer Therapy: A Review," In: Monoclonal Antibodies '84: Biological and Clinical Applications, A. Pincera et al., (eds.) pp. 475-506). Both polyclonal antibodies and monoclonal antibodies have been reported as useful in these strategies (Rowland et al., Cancer Immunol. Immunother. 21:183-87 (1986)).

In certain aspects, ADC include covalent or aggregative conjugates of antibodies, or antigen-binding fragments thereof, with other proteins or polypeptides, such as by expression of recombinant fusion proteins comprising heterologous polypeptides fused to the N-terminus or C-terminus of an antibody polypeptide. For example, the conjugated peptide may be a heterologous signal (or leader) polypeptide, e.g., the yeast alpha-factor leader, or a peptide such as an epitope tag (e.g., V5-His). Antibody-containing fusion proteins may comprise peptides added to facilitate purification or identification of the antibody (e.g., poly-His). An antibody polypeptide also can be linked to the FLAG® (Sigma-Aldrich, St. Louis, Mo.) peptide as described in Hopp et al., Bio/Technology 6:1204 (1988), and U.S. Pat. No. 5,011,912. Oligomers that contain one or more antibody polypeptides may be employed as antagonists. Oligomers may be in the form of covalently linked or non-covalently linked dimers, trimers, or higher oligomers. Oligomers comprising two or more antibody polypeptides are contemplated for use. Other oligomers include heterodimers, homotrimers, heterotrimers, homotetramers, heterotetramers, etc. In certain aspects, oligomers comprise multiple antibody polypeptides joined via covalent or non-covalent interactions between peptide moieties fused to the antibody polypeptides. Such peptides may be peptide linkers (spacers), or peptides that have the property of promoting oligomerization. Leucine zippers and certain polypeptides derived from antibodies are among the peptides that can promote oligomerization of antibody polypeptides attached thereto, as described in more detail below.

3. Conjugation Methodology

Several methods are known in the art for the attachment or conjugation of an antibody to its conjugate moiety. Some attachment methods involve the use of a metal chelate complex employing, for example, an organic chelating agent such as diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates may also be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bos(p-diazoniumbenzoyl)-ethylenediamine), diisocyanates (such as toluene 2,6-diisocyanate), and bis-active fluorine compounds (such as 1,5-difluoro-2,4-dinitrobenzene). In some aspects, derivatization of immunoglobulins by selectively introducing sulfhydryl groups in the Fc region of an immunoglobulin, using reaction conditions that do not alter the antibody combining site, are contemplated. Antibody conjugates produced according to this methodology are disclosed to exhibit improved longevity, specificity, and sensitivity (U.S. Pat. No. 5,196,066, incorporated herein by reference). Site-specific attachment of effector or reporter molecules, wherein the reporter or effector molecule is conjugated to a carbohydrate residue in the Fc region has also been disclosed in the literature (O'Shannessy et al., 1987).

III. Proteins

As used herein, a "protein" or "polypeptide" refers to a molecule comprising at least five amino acid residues. As used herein, the term "wild-type" refers to the endogenous version of a molecule that occurs naturally in an organism. In some embodiments, wild-type versions of a protein or polypeptide are employed, however, in many embodiments of the disclosure, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Where a protein is specifically mentioned herein, it is in general a reference to a native (wild-type) or recombinant (modified) protein or, optionally, a protein in which any signal sequence has been removed. The protein may be isolated directly from the organism of which it is native, produced by recombinant DNA/exogenous expression methods, or produced by solid-phase peptide synthesis (SPPS) or other in vitro methods. In particular embodiments, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino acid residues or greater, and any range derivable therein, or derivative of a corresponding amino sequence described or referenced herein. It is contemplated that polypeptides may be mutated by truncation, rendering them shorter than their corresponding wild-type form, also, they might be altered by fusing or conjugating a heterologous protein or polypeptide sequence with a particular function (e.g., for targeting or localization, for enhanced immunogenicity, for purification purposes, etc.). As used herein, the term "domain" refers to any distinct functional or structural unit of a protein or polypeptide, and generally refers to a sequence of amino acids with a structure or function recognizable by one skilled in the art.

The polypeptides, proteins, or polynucleotides encoding such polypeptides or proteins of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID Nos:1-5.

In some embodiments, the protein or polypeptide may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000, (or any derivable range therein) of SEQ ID NOs:1-5.

In some embodiments, the protein, polypeptide, or nucleic acid may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000, (or any derivable range therein) contiguous amino acids of SEQ ID NOs:1-5.

In some embodiments, the polypeptide, protein, or nucleic acid may comprise at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 (or any derivable range therein) contiguous amino acids of SEQ ID NOs:1-5 that are at least, at most, or about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous with one of SEQ ID NOS:1-5.

In some aspects there is a nucleic acid molecule or polypeptide starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 of any of SEQ ID NOS:1-5 and comprising at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 (or any derivable range therein) contiguous amino acids or nucleotides of any of SEQ ID NOS:1-5.

The nucleotide as well as the protein, polypeptide, and peptide sequences for various genes have been previously disclosed, and may be found in the recognized computerized databases. Two commonly used databases are the National Center for Biotechnology Information's Genbank and Gen-Pept databases (on the World Wide Web at ncbi.nlm.nih.gov/) and The Universal Protein Resource (UniProt; on the World Wide Web at uniprot.org). The coding regions for these genes may be amplified and/or expressed using the techniques disclosed herein or as would be known to those of ordinary skill in the art.

It is contemplated that in compositions of the disclosure, there is between about 0.001 mg and about 10 mg of total polypeptide, peptide, and/or protein per nil. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein).

A. Variant Polypeptides

The following is a discussion of changing the amino acid subunits of a protein to create an equivalent, or even improved, second-generation variant polypeptide or peptide. For example, certain amino acids may be substituted for other amino acids in a protein or polypeptide sequence with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence and in its corresponding DNA coding sequence, and nevertheless produce a protein with similar or desirable properties. It is thus contemplated by the inventors that various changes may be made in the DNA sequences of genes which encode proteins without appreciable loss of their biological utility or activity.

The term "functionally equivalent codon" is used herein to refer to codons that encode the same amino acid, such as the six different codons for arginine. Also considered are "neutral substitutions" or "neutral mutations" which refers to a change in the codon or codons that encode biologically equivalent amino acids.

Amino acid sequence variants of the disclosure can be substitutional, insertional, or deletion variants. A variation in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the protein or polypeptide, as compared to wild-type. A variant can comprise an amino acid sequence that is at least 50%, 60%, 70%, 80%, or 90%, including all values and ranges there between, identical to any sequence provided or referenced herein. A variant can include 2, 3, 4, 5, 6, 7, 8, 9, 10, 11, 12, 13, 14, 15, 16, 17, 18, 19, 20, or more substitute amino acids.

It also will be understood that amino acid and nucleic acid sequences may include additional residues, such as additional N- or C-terminal amino acids, or 5' or 3' sequences, respectively, and yet still be essentially identical as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Deletion variants typically lack one or more residues of the native or wild type protein. Individual residues can be deleted or a number of contiguous amino acids can be deleted. A stop codon may be introduced (by substitution or insertion) into an encoding nucleic acid sequence to generate a truncated protein.

Insertional mutants typically involve the addition of amino acid residues at a non-terminal point in the polypeptide. This may include the insertion of one or more amino acid residues. Terminal additions may also be generated and can include fusion proteins which are multimers or concatemers of one or more peptides or polypeptides described or referenced herein.

Substitutional variants typically contain the exchange of one amino acid for another at one or more sites within the protein or polypeptide, and may be designed to modulate one or more properties of the polypeptide, with or without the loss of other functions or properties. Substitutions may be conservative, that is, one amino acid is replaced with one of similar chemical properties. "Conservative amino acid substitutions" may involve exchange of a member of one amino acid class with another member of the same class. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Conservative amino acid substitutions may encompass non-naturally occurring amino acid residues, which are typically incorporated by chemical peptide synthesis rather than by synthesis in biological systems. These include peptidomimetics or other reversed or inverted forms of amino acid moieties.

Alternatively, substitutions may be "non-conservative", such that a function or activity of the polypeptide is affected. Non-conservative changes typically involve substituting an amino acid residue with one that is chemically dissimilar, such as a polar or charged amino acid for a nonpolar or uncharged amino acid, and vice versa. Non-conservative substitutions may involve the exchange of a member of one of the amino acid classes for a member from another class.

B. Considerations for Substitutions

One skilled in the art can determine suitable variants of polypeptides as set forth herein using well-known techniques. One skilled in the art may identify suitable areas of the molecule that may be changed without destroying activity by targeting regions not believed to be important for activity. The skilled artisan will also be able to identify amino acid residues and portions of the molecules that are conserved among similar proteins or polypeptides. In further embodiments, areas that may be important for biological activity or for structure may be subject to conservative amino acid substitutions without significantly altering the biological activity or without adversely affecting the protein or polypeptide structure.

In making such changes, the hydropathy index of amino acids may be considered. The hydropathy profile of a protein is calculated by assigning each amino acid a numerical value ("hydropathy index") and then repetitively averaging these values along the peptide chain. Each amino acid has been assigned a value based on its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5). The importance of the hydropathy amino acid index in conferring interactive biologic function on a protein is generally understood in the art (Kyte et al., J. Mol. Biol. 157:105-131 (1982)). It is accepted that the relative hydropathic character of the amino acid contributes to the secondary structure of the resultant protein or polypeptide, which in turn defines the interaction of the protein or polypeptide with other molecules, for example, enzymes, substrates, receptors, DNA, antibodies, antigens, and others. It is also known that certain amino acids may be substituted for other amino acids having a similar hydropathy index or score, and still retain a similar biological activity. In making changes based upon the hydropathy index, in certain embodiments, the substitution of amino acids whose hydropathy indices are within ±2 is included. In some aspects of the invention, those that are within ±1 are included, and in other aspects of the invention, those within ±0.5 are included.

It also is understood in the art that the substitution of like amino acids can be effectively made based on hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. In certain embodiments, the greatest local average hydrophilicity of a protein, as governed by the hydrophilicity of its adjacent amino acids, correlates with its immunogenicity and antigen binding, that is, as a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments, the substitution of amino acids whose hydrophilicity values are within ±2 are included, in other embodiments, those which are within ±1 are included, and in still other embodiments, those within ±0.5 are included. In some instances, one may also identify epitopes from primary amino acid sequences based on hydrophilicity. These regions are also referred to as "epitopic core regions." It is understood that an amino acid can be substituted for another having a similar hydrophilicity value and still produce a biologically equivalent and immunologically equivalent protein.

Additionally, one skilled in the art can review structure-function studies identifying residues in similar polypeptides or proteins that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar proteins or polypeptides. In view of such information, one skilled in the art may predict the alignment of amino acid residues of an antibody with respect to its three-dimensional structure. One skilled in the art may choose not to make changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using standard assays for binding and/or activity, thus yielding information gathered from such routine experiments, which may allow one skilled in the art to determine the amino acid positions where further substitutions should be avoided either alone or in combination with other mutations. Various tools available to determine secondary structure can be found on the world wide web at expasy.org/proteomics/protein_structure.

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally occurring sequence. Substitutions can be made in that portion of the antibody that lies outside the domain(s) forming intermolecular contacts. In such embodiments, conservative amino acid substitutions can be used that do not substantially change the structural characteristics of the protein or polypeptide (e.g., one or more replacement amino acids that do not disrupt the secondary structure that characterizes the native antibody).

IV. Nucleic Acids

In certain embodiments, nucleic acid sequences can exist in a variety of instances such as: isolated segments and recombinant vectors of incorporated sequences or recombinant polynucleotides encoding one or both chains of an antibody, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing described herein. Nucleic acids that encode the epitope to which certain of the antibodies provided herein are also provided. Nucleic acids encoding fusion proteins that include these peptides are also provided. The nucleic acids can be single-stranded or double-stranded and can comprise RNA and/or DNA nucleotides and artificial variants thereof (e.g., peptide nucleic acids).

The term "polynucleotide" refers to a nucleic acid molecule that either is recombinant or has been isolated from total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

A. Hybridization

The nucleic acids that hybridize to other nucleic acids under particular hybridization conditions. Methods for hybridizing nucleic acids are well known in the art. See, e.g., Current Protocols in Molecular Biology, John Wiley and Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C. in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequence that are at least 65%, at least 70%, at least 75%, at least 80%, at least 85%, at least 90%, at least 95%, at least 96%, at least 97%, at least 98% or at least 99% identical to each other typically remain hybridized to each other.

The parameters affecting the choice of hybridization conditions and guidance for devising suitable conditions are set forth by, for example, Sambrook, Fritsch, and Maniatis (Molecular Cloning: A Laboratory Manual, Cold Spring Harbor Laboratory Press, Cold Spring Harbor, N.Y., chapters 9 and 11 (1989); Current Protocols in Molecular Biology, Ausubel et al., eds., John Wiley and Sons, Inc., sections 2.10 and 6.3-6.4 (1995), both of which are herein incorporated by reference in their entirety for all purposes) and can be readily determined by those having ordinary skill in the art based on, for example, the length and/or base composition of the DNA.

B. Mutation

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. See, eg., Romain Studer et al., Biochem. J. 449: 581-594 (2013). For example, the mutation can quantitatively or qualitatively change the biological activity. Examples of quantitative changes include increasing, reducing or eliminating the activity. Examples of qualitative changes include altering the antigen specificity of an antibody.

C. Probes

In another aspect, nucleic acid molecules are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion of a given polypeptide.

In another embodiment, the nucleic acid molecules may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of antibodies. See, eg., Gaily Kivi et al., BMC Biotechnol. 16:2 (2016). In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or part of one or more of the CDRs.

Probes based on the desired sequence of a nucleic acid can be used to detect the nucleic acid or similar nucleic acids, for example, transcripts encoding a polypeptide of interest. The probe can comprise a label group, e.g., a radioisotope, a fluorescent compound, an enzyme, or an enzyme co-factor. Such probes can be used to identify a cell that expresses the polypeptide.

V. Antibody Production

A. Antibody Production

Methods for preparing and characterizing antibodies for use in diagnostic and detection assays, for purification, and for use as therapeutics are well known in the art as disclosed in, for example, U.S. Pat. Nos. 4,011,308; 4,722,890; 4,016,043; 3,876,504; 3,770,380; and 4,372,745 (see, e.g., Antibodies: A Laboratory Manual, Cold Spring Harbor Laboratory, 1988; incorporated herein by reference). These antibodies may be polyclonal or monoclonal antibody preparations, monospecific antisera, human antibodies, hybrid or chimeric antibodies, such as humanized antibodies, altered antibodies, F(ab')2 fragments, Fab fragments, Fv fragments, single-domain antibodies, dimeric or trimeric antibody fragment constructs, minibodies, or functional fragments thereof which bind to the antigen in question. In certain aspects, polypeptides, peptides, and proteins and immunogenic fragments thereof for use in various embodiments can also be synthesized in solution or on a solid support in accordance with conventional techniques. See, for example, Stewart and Young, (1984); Tarn et al, (1983); Merrifield, (1986); and Barany and Merrifield (1979), each incorporated herein by reference.

Briefly, a polyclonal antibody is prepared by immunizing an animal with an antigen or a portion thereof and collecting antisera from that immunized animal. The antigen may be altered compared to an antigen sequence found in nature. In some embodiments, a variant or altered antigenic peptide or polypeptide is employed to generate antibodies. Inocula are typically prepared by dispersing the antigenic composition in a physiologically tolerable diluent to form an aqueous composition. Antisera is subsequently collected by methods known in the arts, and the serum may be used as-is for various applications or else the desired antibody fraction may be purified by well-known methods, such as affinity chromatography (Harlow and Lane, Antibodies: A Laboratory Manual 1988).

Methods of making monoclonal antibodies are also well known in the art (Kohler and Milstein, 1975; Harlow and Lane, 1988, U.S. Pat. No. 4,196,265, herein incorporated by reference in its entirety for all purposes). Typically, this technique involves immunizing a suitable animal with a selected immunogenic composition, e.g., a purified or partially purified protein, polypeptide, peptide or domain. Resulting antibody-producing B-cells from the immunized animal, or all dissociated splenocytes, are then induced to fuse with cells from an immortalized cell line to form hybridomas. Myeloma cell lines suited for use in hybridoma-producing fusion procedures preferably are non-antibody-producing and have high fusion efficiency and enzyme deficiencies that render then incapable of growing in certain selective media that support the growth of only the desired fused cells (hybridomas). Typically, the fusion partner includes a property that allows selection of the resulting hybridomas using specific media. For example, fusion partners can be hypoxanthine/aminopterin/thymidine (HAT)-sensitive. Methods for generating hybrids of antibody-producing spleen or lymph node cells and myeloma cells usually comprise mixing somatic cells with myeloma cells in the presence of an agent or agents (chemical or electrical) that promote the fusion of cell membranes. Next, selection of hybridomas can be performed by culturing the cells by single-clone dilution in microtiter plates, followed by testing the individual clonal supernatants (after about two to three weeks) for the desired reactivity. Fusion procedures for making hybridomas, immunization protocols, and techniques for isolation of immunized splenocytes for fusion are known in the art.

Other techniques for producing monoclonal antibodies include the viral or oncogenic transformation of B-lymphocytes, a molecular cloning approach may be used to generate a nucleic acid or polypeptide, the selected lymphocyte antibody method (SLAM) (see, e.g., Babcook et al., Proc. Natl. Acad. Sci. USA 93:7843-7848 (1996), the preparation of combinatorial immunoglobulin phagemid libraries from RNA isolated from the spleen of the immunized animal and selection of phagemids expressing appropriate antibodies, or producing a cell expressing an antibody from a genomic sequence of the cell comprising a modified immunoglobulin locus using Cre-mediated site-specific recombination (see, e.g., U.S. Pat. No. 6,091,001).

Monoclonal antibodies may be further purified using filtration, centrifugation, and various chromatographic methods such as HPLC or affinity chromatography. Monoclonal antibodies may be further screened or optimized for properties relating to specificity, avidity, half-life, immunogenicity, binding association, binding disassociation, or overall functional properties relative to being a treatment for infection. Thus, monoclonal antibodies may have alterations in the amino acid sequence of CDRs, including insertions, deletions, or substitutions with a conserved or non-conserved amino acid.

The immunogenicity of a particular immunogen composition can be enhanced by the use of non-specific stimulators of the immune response, known as adjuvants. Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, and monophosphoryl lipid A (MPL). Exemplary adjuvants may include complete Freund's adjuvant (a non-specific stimulator of the immune response containing killed Mycobacterium tuberculosis), incomplete Freund's adjuvants, and/or aluminum hydroxide adjuvant. In addition to adjuvants, it may be desirable to co-administer biologic response modifiers (BRM), such as but not limited to, Cimetidine (CIM; 1200 mg/d) (Smith/Kline, PA); low-dose Cyclophosphamide (CYP; 300 mg/m2) (Johnson/Mead, NJ), cytokines such as β-interferon, IL-2, or IL-12, or genes encoding proteins involved in immune helper functions, such as B-7. A phage-display system can be used to expand antibody molecule populations in vitro. Saiki, et al., Nature 324:163 (1986); Scharf et al., Science 233:1076 (1986); U.S. Pat. Nos. 4,683,195 and 4,683,202; Yang et al., J Mol Biol. 254:392 (1995); Barbas, III et al., Methods: Comp. Meth Enzymol. (1995) 8:94; Barbas, III et al., Proc Natl Acad Sci USA 88:7978 (1991).

B. Fully Human Antibody Production

Methods are available for making fully human antibodies. Using fully human antibodies can minimize the immunogenic and allergic responses that may be caused by administering non-human monoclonal antibodies to humans as therapeutic agents. In one embodiment, human antibodies may be produced in a non-human transgenic animal, e.g., a transgenic mouse capable of producing multiple isotypes of human antibodies to protein (e.g., IgG, IgA, and/or IgE) by undergoing V-D-J recombination and isotype switching. Accordingly, this aspect applies to antibodies, antibody fragments, and pharmaceutical compositions thereof, but also non-human transgenic animals, B-cells, host cells, and hybridomas that produce monoclonal antibodies. Applications of humanized antibodies include, but are not limited to, detect a cell expressing an anticipated protein, either in vivo or in vitro, pharmaceutical preparations containing the antibodies of the present invention, and methods of treating disorders by administering the antibodies.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., Proc. Natl. Acad. Sci. USA 90:2551-2555 (1993); Jakobovits et al., Nature 362:255-258 (1993); Bruggermann et al., Year in Immunol. 7:33 (1993). In one example, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then crossbred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, International Patent Application Publication Nos. WO 96/33735 and WO 94/02602, which are hereby incorporated by reference in their entirety. Additional methods relating to transgenic mice for making human antibodies are described in U.S. Pat. Nos. 5,545,807; 6,713,610; 6,673,986; 6,162,963; 6,300,129; 6,255,458; 5,877,397; 5,874,299 and 5,545,806; in International Patent Application Publication Nos. WO 91/10741 and WO 90/04036; and in European Patent Nos. EP 546073B1 and EP 546073A1, all of which are hereby incorporated by reference in their entirety for all purposes.

The transgenic mice described above, referred to herein as "HuMAb" mice, contain a human immunoglobulin gene minilocus that encodes unrearranged human heavy (μ and ?) and ? light chain immunoglobulin sequences, together with targeted mutations that inactivate the endogenous μ and ? chain loci (Lonberg et al., Nature 368:856-859 (1994)). Accordingly, the mice exhibit reduced expression of mouse IgM or ? chains and in response to immunization, the introduced human heavy and light chain transgenes undergo class switching and somatic mutation to generate high affinity human IgG ? monoclonal antibodies (Lonberg et al., supra; Lonberg and Huszar, Intern. Ref. Immunol. 13:65-93 (1995); Harding and Lonberg, Ann. N.Y. Acad. Sci. 764:536-546 (1995)). The preparation of HuMAb mice is described in detail in Taylor et al., Nucl. Acids Res. 20:6287-6295 (1992); Chen et al., Int. Immunol. 5:647-656 (1993); Tuaillon et al., J. Immunol. 152:2912-2920 (1994); Lonberg et al., supra; Lonberg, Handbook of Exp. Pharmacol. 113: 49-101 (1994); Taylor et al., Int. Immunol. 6:579-591 (1994); Lonberg and Huszar, Intern. Ref. Immunol. 13:65-93 (1995); Harding and Lonberg, Ann. N.Y. Acad. Sci. 764:536-546 (1995); Fishwild et al., Nat. Biotechnol. 14:845-851(1996); the foregoing references are herein incorporated by reference in their entirety for all purposes. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as International Patent Application Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., Nat. Genetics 15:146-156 (1997), which are herein incorporated by reference. For example, the HCo7 and HCo12 transgenic mice strains can be used to generate human antibodies.

Using hybridoma technology, antigen-specific humanized monoclonal antibodies with the desired specificity can be produced and selected from the transgenic mice such as those described above. Such antibodies may be cloned and expressed using a suitable vector and host cell, or the antibodies can be harvested from cultured hybridoma cells. Fully human antibodies can also be derived from phage-display libraries (as disclosed in Hoogenboom et al., J. Mol. Biol. 227:381 (1991); and Marks et al., J. Mol. Biol. 222:581 (1991)). One such technique is described in International Patent Application Publication No. WO 99/10494 (herein incorporated by reference), which describes the isolation of high affinity and functional agonistic antibodies for MPL- and msk-receptors using such an approach.

C. Antibody Fragments Production

Antibody fragments that retain the ability to recognize the antigen of interest will also find use herein. A number of antibody fragments are known in the art that comprise antigen-binding sites capable of exhibiting immunological binding properties of an intact antibody molecule and can be subsequently modified by methods known in the arts. Functional fragments, including only the variable regions of the heavy and light chains, can also be produced using standard techniques such as recombinant production or preferential proteolytic cleavage of immunoglobulin molecules. These fragments are known as Fv. See, e.g., Inbar et al., Proc. Nat. Acad. Sci. USA 69:2659-2662 (1972); Hochman et al., Biochem. 15:2706-2710 (1976); and Ehrlich et al., Biochem. 19:4091-4096 (1980).

Single-chain variable fragments (scFvs) may be prepared by fusing DNA encoding a peptide linker between DNAs encoding the two variable domain polypeptides (VL and VH). scFvs can form antigen-binding monomers, or they can form multimers (e.g., dimers, trimers, or tetramers), depending on the length of a flexible linker between the two variable domains (Kortt et al., Prot. Eng. 10:423 (1997); Kort et al., Biomol. Eng. 18:95-108 (2001)). By combining different VL- and VH-comprising polypeptides, one can form multimeric scFvs that bind to different epitopes (Kriangkum et al., Biomol. Eng. 18:31-40 (2001)). Antigen-binding fragments are typically produced by recombinant DNA methods known to those skilled in the art. Although the two domains of the Fv fragment, VL and VH, are coded for by separate genes, they can be joined using recombinant methods by a synthetic linker that enables them to be made as a single chain polypeptide (known as single chain Fv (sFv or scFv); see e.g., Bird et al., Science 242:423-426 (1988); and Huston et al., Proc. Natl. Acad. Sci. USA 85:5879-5883 (1988). Design criteria include determining the appropriate length to span the distance between the C-terminus of one chain and the N-terminus of the other, wherein the linker is generally formed from small hydrophilic amino acid residues that do not tend to coil or form secondary structures. Suitable linkers generally comprise polypeptide chains of alternating sets of glycine and serine residues, and may include glutamic acid and lysine residues inserted to enhance solubility. Antigen-binding fragments are screened for utility in the same manner as intact antibodies. Such fragments include those obtained by amino-terminal and/or carboxy-terminal deletions, where the remaining amino acid sequence is substantially identical to the corresponding positions in the naturally occurring sequence deduced, for example, from a full-length cDNA sequence.

Antibodies may also be generated using peptide analogs of the epitopic determinants disclosed herein, which may consist of non-peptide compounds having properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al., J. Med. Chem. 30:1229 (1987). Liu et al. (2003) also describe "antibody like binding peptidomimetics" (ABiPs), which are peptides that act as pared-down antibodies and have certain advantages of longer serum half-life as well as less cumbersome synthesis methods. These analogs can be peptides, non-peptides or combinations of peptide and non-peptide regions. Fauchere, Adv. Drug Res. 15:29 (1986); Veber and Freidiner, TINS p. 392 (1985); and Evans et al., J. Med. Chem. 30:1229 (1987), which are incorporated herein by reference in their entirety for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as the ability to bind a protein, but have one or more peptide linkages optionally replaced by a linkage selected from: —CH2NH—, —CH2S—, —CH2-CH2-, —CH—CH— (cis and trans), —COCH2-, —CH(OH)CH2-, and —CH2SO— by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, Ann. Rev. Biochem. 61:387 (1992), incorporated herein by reference), for example, by adding internal cysteine residues capable of forming intramolecular disulfide bridges which cyclize the peptide.

Once generated, a phage display library can be used to improve the immunological binding affinity of the Fab molecules using known techniques. See, e.g., Figini et al., J. Mol. Biol. 239:68 (1994). The coding sequences for the heavy and light chain portions of the Fab molecules selected from the phage display library can be isolated or synthesized and cloned into any suitable vector or replicon for expression. Any suitable expression system can be used.

VI. Obtaining Encoded Antibodies

In some aspects, there are nucleic acid molecule encoding antibody polypeptides (e.g., heavy or light chain, variable domain only, or full-length). These may be generated by methods known in the art, e.g., isolated from B cells of mice that have been immunized and isolated, phage display, expressed in any suitable recombinant expression system and allowed to assemble to form antibody molecules.

A. Expression

The nucleic acid molecules may be used to express large quantities of recombinant antibodies or to produce chimeric antibodies, single chain antibodies, immunoadhesins, diabodies, mutated antibodies, and other antibody derivatives. If the nucleic acid molecules are derived from a non-human, non-transgenic animal, the nucleic acid molecules may be used for antibody humanization.

B. Vectors

In some aspects, contemplated are expression vectors comprising a nucleic acid molecule encoding a polypeptide of the desired sequence or a portion thereof (e.g., a fragment containing one or more CDRs or one or more variable region domains). Expression vectors comprising the nucleic acid molecules may encode the heavy chain, light chain, or the antigen-binding portion thereof. In some aspects, expression vectors comprising nucleic acid molecules may encode fusion proteins, modified antibodies, antibody fragments, and probes thereof. In addition to control sequences that govern transcription and translation, vectors and expression vectors may contain nucleic acid sequences that serve other functions as well.

To express the antibodies, or antigen-binding fragments thereof, DNAs encoding partial or full-length light and heavy chains are inserted into expression vectors such that the gene area is operatively linked to transcriptional and translational control sequences. In some aspects, a vector that encodes a functionally complete human CH or CL immunoglobulin sequence with appropriate restriction sites engineered so that any VH or VL sequence can be easily inserted and expressed. Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Such sequences and methods of using the same are well known in the art.

1. Expression Systems

Numerous expression systems exist that comprise at least a part or all of the expression vectors discussed above. Prokaryote- and/or eukaryote-based systems can be employed for use with an embodiment to produce nucleic acid sequences, or their cognate polypeptides, proteins and peptides. Commercially and widely available systems include in but are not limited to bacterial, mammalian, yeast, and insect cell systems. Different host cells have characteristic and specific mechanisms for the post-translational processing and modification of proteins. Appropriate cell lines or host systems can be chosen to ensure the correct modification and processing of the foreign protein expressed. Those skilled in the art are able to express a vector to produce a nucleic acid sequence or its cognate polypeptide, protein, or peptide using an appropriate expression system.

2. Methods of Gene Transfer

Suitable methods for nucleic acid delivery to effect expression of compositions are anticipated to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563, 055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Other methods include viral transduction, such as gene transfer by lentiviral or retroviral transduction.

3. Host Cells

In another aspect, contemplated are the use of host cells into which a recombinant expression vector has been introduced. Antibodies can be expressed in a variety of cell types. An expression construct encoding an antibody can be transfected into cells according to a variety of methods known in the art. Vector DNA can be introduced into prokaryotic or eukaryotic cells via conventional transformation or transfection techniques. Some vectors may employ control sequences that allow it to be replicated and/or expressed in both prokaryotic and eukaryotic cells. In certain aspects, the antibody expression construct can be placed under control of a promoter that is linked to T-cell activation, such as one that is controlled by NFAT-1 or NF-??, both of which are transcription factors that can be activated upon T-cell activation. Control of antibody expression allows T cells, such as tumor-targeting T cells, to sense their surroundings and perform real-time modulation of cytokine signaling, both in the T cells themselves and in surrounding endogenous immune cells. One of skill in the art would understand the conditions under which to incubate host cells to maintain them and to permit replication of a vector. Also understood and known are techniques and conditions that would allow large-scale production of vectors, as well as production of the nucleic acids encoded by vectors and their cognate polypeptides, proteins, or peptides.

For stable transfection of mammalian cells, it is known, depending upon the expression vector and transfection technique used, only a small fraction of cells may integrate the foreign DNA into their genome. In order to identify and select these integrants, a selectable marker (e.g., for resistance to antibiotics) is generally introduced into the host cells along with the gene of interest. Cells stably transfected with the introduced nucleic acid can be identified by drug selection (e.g., cells that have incorporated the selectable marker gene will survive, while the other cells die), among other methods known in the arts.

C. Isolation

The nucleic acid molecule encoding either or both of the entire heavy and light chains of an antibody or the variable regions thereof may be obtained from any source that produces antibodies. Methods of isolating mRNA encoding an antibody are well known in the art. See e.g., Sambrook et al., supra. The sequences of human heavy and light chain constant region genes are also known in the art. See, e.g., Kabat et al., 1991, supra. Nucleic acid molecules encoding the full-length heavy and/or light chains may then be expressed in a cell into which they have been introduced and the antibody isolated.

VII. Administration of Therapeutic Compositions

The therapy provided herein may comprise administration of a combination of therapeutic agents, such as a first cancer therapy and a second cancer therapy. The therapies may be administered in any suitable manner known in the art. For example, the first and second cancer treatment may be administered sequentially (at different times) or concurrently (at the same time). In some embodiments, the first and second cancer treatments are administered in a separate composition. In some embodiments, the first and second cancer treatments are in the same composition.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. In some embodiments, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 µg/kg, mg/kg, µg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 µM to 150 µM. In another embodiment, the effective dose provides a blood level of about 4 µM to 100 µM.; or about 1 µM to 100 µM; or about 1 µM to 50 µM; or about 1 µM to 40 µM; or about 1 µM to 30 µM; or about 1 µM to 20 µM; or about 1 µM to 10 µM; or about 10 µM to 150 µM; or about 10 µM to 100 µM; or about 10 µM to 50 µM; or about 25 µM to 150 µM; or about 25 µM to 100 µM; or about 25 µM to 50 µM; or about 50 µM to 150 µM; or about 50 µM to 100 µM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of µg/kg or mg/kg of body weight can be converted and expressed in comparable concentration units of µg/ml or mM (blood levels), such as 4 µM to 100 µM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

VIII. Kits

Certain aspects of the present invention also concern kits containing compositions of the invention or compositions to implement methods of the invention. In some embodiments, kits can be used to evaluate one or more biomarkers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein. In some embodiments, there are kits for evaluating biomarker activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, synthetic nucleic acids, nonsynthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker.

In certain aspects, negative and/or positive control nucleic acids, probes, and inhibitors are included in some kit embodiments. In addition, a kit may include a sample that is a negative or positive control for methylation of one or more biomarkers. In some embodiments, a control includes a nucleic acid that contains at least one CpG or is capable of identifying a CpG methylation site.

It is contemplated that any method or composition described herein can be implemented with respect to any other method or composition described herein and that different embodiments may be combined. The claims originally filed are contemplated to cover claims that are multiply dependent on any filed claim or combination of filed claims.

Any embodiment of the disclosure involving specific biomarker by name is contemplated also to cover embodiments involving biomarkers whose sequences are at least 80, 81, 82, 83, 84, 85, 86, 87, 88, 89, 90, 91, 92, 93, 94, 95, 96, 97, 98, 99% identical to the mature sequence of the specified nucleic acid.

Embodiments of the disclosure include kits for analysis of a pathological sample by assessing biomarker profile for a sample comprising, in suitable container means, two or more biomarker probes, wherein the biomarker probes detect one or more of the biomarkers identified herein. The kit can further comprise reagents for labeling nucleic acids in the sample. The kit may also include labeling reagents, including at least one of amine-modified nucleotide, poly(A) polymerase, and poly(A) polymerase buffer. Labeling reagents can include an amine-reactive dye.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Probing for Synergy Against Migraine Modeled in Rats Using Combined Anti-CGRP mAb and IGF-1

There is evidence calcitonin gene-related peptide (CGRP) is involved in the nociceptive signaling of migraine, and this preclinical and clinical data has led to the development of CGRP monoclonal antibodies (CGRP-mAbs) to treat migraine. Yet, the mechanisms by which CGRP-mAbs impact migraine are only beginning to be defined.

In recent work, others have demonstrated that the CGRP-mAb [fremanezumab (TEV-48125)] selectively modulates meningeal sensory fibers (Melo-Carrillo et al., 2017a). Using cortical spreading depression (CSD), a well-accepted model of migraine and its related hyperexcitability, they show that, with time, TEV-48125 inhibited activation and sensitization of high threshold trigeminal system neurons after CSD. Furthermore, TEV-48125 inhibited naïve high threshold neurons and reduced their activation following stimulation of the intracranial dura, but not the facial skin or cornea. However, TEV-481245 had no effect on wide dynamic range neurons of the caudal trigeminal nucleus. In subsequent work, it was demonstrated that, although TEV-48125 did not directly inhibit CSD, it did reduce CSD-based activation of Aδ fibers but not activation of C-fiber afferents in the trigeminal ganglion (Melo-Carrillo et al., 2017b).

The authors suggest that this differential impact on activation of mechanosensitive primary afferent meningeal nociceptors may explain why the CGRP-mAb is not effective in all patients. The authors note that C-fibers are the source of CGRP in the trigeminal ganglion, and release CGRP upon activation (e.g., from CSD and by extension migraine). In contrast, Aδ fibers are activated in response to CGRP, an effect that is inhibited by TEV-48125.

It is hypothesized that the addition of insulin-like growth factor-1 (IGF-1) will significantly improve the efficacy of TEV-48125 as a migraine therapeutic. The inventors are developing IGF-1 as a novel, naturally-occurring migraine treatment. IGF-1 reduces the hyperexcitability and oxidative stress needed to trigger CSD, and the inventors reason the hyperexcitability and oxidative stress known to occur in the trigeminal system with models of migraine. The inventors' work is based on research into understanding how increased physical and intellectual activity (i.e., environmental enrichment) reduces susceptibility to CSD. In humans, increased physical activity reduces susceptibility to migraine. IGF-1 increases with environmental enrichment and enters brain with increased neural activity from sensory stimulation. Using both in vitro and in vivo models of migraine, the inventors show that IGF-1 is significantly protective against CSD. This effect involves abrogation of microglial-derived oxidative stress, which otherwise triggers the hyperexcitability burst needed to initiate CSD. Also, IGF-1 significantly protects against CSD after nose-to-brain (N2B) administration in vivo to adult rats (Grinberg et al., 2017).

Work from the inventors' laboratory showed that N2B IGF-1 significantly reduced naïve levels of CGRP in the trigeminal ganglion by ~75% (see below). In recently completed work, the inventors extend these results to show that N2B also significantly reduced trigeminal system activation from recurrent CSD (see below).

Accordingly, it is contemplated that combined treatment with subcutaneous CGRP-mAb inhibitor and N2B delivery of IGF-1 mitigates trigeminal system activation compared to either agent alone. This work will be done using the systemic NTG model of migraine. The primary objectives are to determine trigeminal ganglion levels of activation (i.e., CGRP expression, oxidative stress markers). Secondary objectives are to make parallel measurements of trigeminal nucleus caudalis activation (i.e., c-fos) and measure blood levels of CGRP.

A. Results

The inventors have completed a full-length study examining the ability of N2B IGF-1 to reduce trigeminal system activation from recurrent CSD (Won and Kraig 2019a,b, 2020). The points enumerated below emphasize the utility of combining IGF-1 with a representative CGRP-mAb as a combined therapy. 1) N2B administration of IGF-1 to adult rats did not induce nociceptive activation of the trigeminal nucleus as would be expected if such delivery causes headache, a side effect seen in up to 5% of patients treated with systemic IGF-1 for short stature. Instead, it was found that nose to brain delivery of IGF-1 significantly ($p<0.001$; n=5/group) reduced trigeminal ganglion levels of CGRP by 75% (FIG. 1). This new data is incorporated into a schematic that illustrates the inventors' understanding (from in vitro and in vivo work) of the underlying biology used to propose IGF-1 as a novel therapeutic for migraine (FIG. 2). 2) Nasal administration of IGF-1 did not induce hypoglycemia (FIG. 3).

B. Significance

Migraine is an immense healthcare burden that costs $30 billion a year in the United States alone. New CGRP-mAbs represent a therapeutic means to mitigate the impact of migraine in many patients. However, the differential impact on activation of mechanosensitive primary afferent meningeal nociceptors may begin to explain why CGRP-mAbs are not effective in all patients. Another important of consideration is that while these agents reduce nociceptive activation by blocking pain related CGRP in the trigeminal system, they do so without impacting the underlying causes of migraine—brain hyperexcitability and oxidative stress. Thus, improvement of therapies that extend from the basic physiology of CGRP-mAbs are warranted. The inventors suggest that combining CGRP-mAbs with other anti-migraine agents may provide added relief compared to individual agents alone.

This project will determine the utility of combined treatment with a representative CGRP-mAb and nasal delivery of IGF-1 as a therapeutic against trigeminal system activation associated with migraine.

C. Methods

Migraine will be modeled via intraperitoneal injection of nitroglycerin (NTG) in rats (Moye and Pradhan, 2017). Two days before NTG treatment, animals will be administered subcutaneous CGRP-mAb (30 mg/kg) or isotype antibody control. Then the day before NTG injection, rats will be anesthetized with inhalational isoflurane [~5% via nasal mask in oxygen with temperature ($37\pm0.5°$ C.) and arterial oxygen (95-100 mm Hg) monitoring] and given human recombinant IGF-1 (150 µg) in 50 µL succinate buffer or vehicle (50 µL of succinate buffer) intranasally over 20 minutes (Grinberg et al., 2017). Afterward, rats will be returned to single animal standard housing. 24 hours later, rats will briefly restrained and given an intraperitoneal injection of NTG. A stock of 5 mg/mL pharmaceutical grade NTG in 30% alcohol, 30% propylene glycol, and water will be freshly diluted each day with 0.9% saline to obtain a final concentration of 1 mg/mL NTG in 6% alcohol, 6% propylene glycol in 0.9% saline. Dilution of the NTG stock is needed to achieve a lower alcohol and propylene glycol concentration which does not affect pain related indices (mechanical sensitivity) when used as a vehicle for mouse chronic migraine studies [Moye And Pradhan, 2017]. In contrast, vehicle effects on photophobia and locomotor activity were reported when composed of 30% ETOH and 30% propylene glycol (Harris et al., (2017). Rats will be allowed to recover for 2 hours post-NTG injection in individual cages before being anesthetized with intraperitoneal Ketamine/Xylazine and euthanized via intra-cardiac perfusion-fixation and tissues harvested for histological analyses. Animal groups and endpoints are defined below.

D. Design

Animal groups. The inventors' previous work shows that 5/group is sufficient to reach statistical significance with a power $>0.80$ and near or equal to 1.00 for whole animal experiments involving CSD and trigeminal system activation. Therefore, the inventors anticipate using n=5 animals per group here. Animal groups will consist of: 1) naïve controls; 2) treatment with IP NTG; 3) treatment with IP NTG vehicle; 4) treatment with IP NTG and SQ CGRP-mAbs; 5) treatment with IP NTG and SQ isotype antibody control; 6) treatment with IP NTG and nasally delivered IGF-1; 7) treatment with IP NTG and nasally delivered succinate buffer; 8) treatment with IP NTG and SQ CGRP-mAb plus nasally delivered IGF-1; 9) treatment with IP NTG and SQ CGRP-mAb plus nasally delivered succinate buffer; and 10) treatment with IP NTG and SQ isotype antibody control plus nasally delivered IGF-1.

Endpoints. The endpoints for this project are to harvest brain and trigeminal ganglia tissues for immunohistochemical analyses following perfusion with fixative 4 hours post-NTG injection. Trigeminal ganglion measurements will be: immunohistochemical assays of CGRP and oxidative stress. Caudal trigeminal nucleus measurements will be assays of superficial laminae c-fos immunostaining. Blood will be collected from cardiac puncture for CGRP levels immediately before perfusion-fixation.

Statistical procedures: All data analyses will be performed blinded to treatments, according to STAIR and ARRIVE criteria, and statistically treated via ANOVA and post-hoc testing or t-testing as appropriate.

All data will be analyzed using SigmaPlot (v.12.5; Systat Software, Inc., San Jose, CA). All data were subject to normality testing (p-value to reject: 0.05), equal variance testing (p-value to reject: 0.05), and power ($1-\beta$: $>0.8$). Data will be presented as a natural log ratio of experimental over control data. In this way, a value of "0" would reflect no change from control while a positive logarithm would indicate an increase and a negative logarithm a decrease. The inventors have used this statistical method for computer-based semi-quantitative immunohistochemical analyses (Kraig et al, 1991).

REFERENCES

The following references, to the extent that they provide exemplary procedural or other details supplementary to those set forth herein, are specifically incorporated herein by reference.

1. Melo-Carrillo A. et al., Noseda R, Nir R R, Schain A J, Stratton J, Strassman A M, Burstein R (2017a) Selective Inhibition of Trigeminovascular Neurons by Fremanezumab: A Humanized Monoclonal Anti-CGRP Antibody. J Neurosci. 37:7149-7163.
2. Melo-Carrillo A, Strassman A M, Nir R R, Schain A J, Noseda R, Stratton J, Burstein R (2017b) Fremanezumab-A Humanized Monoclonal Anti-CGRP Antibody-Inhibits Thinly Myelinated (Aδ) But Not Unmyelinated (C) Meningeal Nociceptors. J Neurosci. 37:10587-10596.

3. Grinberg Y Y, Zitzow L A, Kraig R P (2017) Intranasally administered IGF-1 inhibits spreading depression in vivo. Brain Res. 1677:47-57.
4. Kraig R P, Dong L M, Thisted R, Jaeger C B (1991) Spreading depression increases immunohistochemical staining of glial fibrillary acidic protein. J Neurosci. 11:2187-98.
5. Kohn D F, Clifford C B. Biology and diseases of rats. In: J G Fox, L C Anderson, F M Lowe, F Quimby, editors. Laboratory Animal Medicine. New York: Academic Press, 2002. pp. 121-167.
6. Cohen J M, Dodick D W, Yang R, Newman L C, Li T, Aycardi E, Bigal M E (2017) Fremanezumab as Add-On Treatment for Patients Treated With Other Migraine Preventive Medicines. Headache. 57:1375-1384
7. Moye L S & Pradhan A A A (2017). Animal model of chronic migraine-associated pain. Current Protocols in Neuroscience, 80, 9.60.1-9.60.9. doi: 10.1002/cpns.33.
8. Harris H M, Carpenter J M, Black J R, Smitherman T A, Sufka K J (2017) The effects of repeated nitroglycerin administrations in rats; modeling migraine-related endpoints and chronification. J Neurosci Methods. 284:63-70.
9. Won L. Kraig R P (2019a) Development of nasal insulin-like growth factor-1 as a treatment for migraine. American Headache Society. 59: (Supplement 1) P221LB.
10. Won L, Kraig R P (2019b) Nose-to-brain delivery of IGF-1 abrogates trigeminal system activation including oxidative stress and CGRP from recurrent spreading depression. Soc. Neurosci. 45: #3725.
11. Won L, Kraig R P. (2020) Insulin-like growth factor-1 inhibits spreading depression-induced trigeminal calcitonin gene related peptide, oxidative stress & neuronal activation in rat. Brain Res. 1732:146673. doi: 10.1016/j.brainres.2020.146673. Epub 2020 Jan. 21. PMID: 31978377. PMCID: 6733989.

Example 2

Insulin-Like Growth Factor-1 Inhibits Spreading Depression-Induced Trigeminal Calcitonin Gene Related Peptide, Oxidative Stress & Neuronal Activation in Rat Migraineurs show brain hyperexcitability and increased oxidative stress. Since hyperexcitability enhances oxidative stress and oxidative stress promotes hyperexcitability, ending this vicious feed-back loop may lead to novel therapeutics for migraine. Spreading depression, the most likely cause of migraine aura and perhaps pain, triggers oxidative stress not only in the cortical area involved in spreading depression, but also in the trigeminal system, a locus important to pain pathway activation in migraine. Additionally, oxidative stress causes increased trigeminal calcitonin gene-related peptide release and oxidative stress can reduce spreading depression threshold. Previously, the inventors showed that insulin-like growth factor-1 significantly protects against spreading depression in vitro by reducing oxidative stress. Additionally, insulin-like growth factor-1 significantly protects against spreading depression after nasal administration in vivo to adult rats.

Methods/Results: Here, the inventors extend this work using adult male rats to the trigeminal system where insulin-like growth factor-1 receptors are highly expressed. Nasal delivery of insulin-like growth factor-1 significantly reduced naïve levels of trigeminal ganglion calcitonin gene related peptide and unlike systemic delivery, no impact on blood glucose levels occurred. Furthermore, nasal delivery of insulin-like growth factor-1 a day before recurrent cortical spreading depression (CSD) significantly reduced trigeminal ganglion oxidative stress and calcitonin gene related peptide levels plus caudal trigeminal nucleus c-fos activation.

This work provides strong evidence to indicate that nasal delivery of insulin-like growth factor-1 can mitigate not only the spreading depression related cause of migraine modeled in animals, but also nociceptive consequences in the trigeminal system.

A. Introduction

CNS hyperexcitability occurs in migraine patients (1) along with increased levels of oxidative stress (OS) (2, 3). Since hyperexcitability enhances OS and OS promotes hyperexcitability, unraveling this vicious cycle especially as it relates to the trigeminal system (TS) may lead to novel therapeutics for migraine (4, 5). Shatillo and colleagues (6) show that neocortical spreading depression (SD), the most likely cause of migraine aura and perhaps pain (7, 8), triggers OS not only in the cortical area involved in SD, but also the TS, a locus important to pain pathway activation in migraine (9). They also note that OS can increase calcitonin gene-related peptide (CGRP) release in dorsal root ganglion neurons (6). Anti-CGRP biologics designed to block migraine pain are now available and are making important improvements to migraine treatment. However, they do not prevent the root cause of migraine (10, 11) and may be no more effective than existing therapeutics (12). Thus, there is an unmet need for therapeutics to treat frequent migraine sufferers more effectively.

In this example, the inventors show that N2B delivery of IGF-1 significantly prevents nociceptive activation of the TS from recurrent SD. This work appeared in preliminary form (22, 23) and has now been published as a full-length manuscript (51).

B. Methods

1. Animals

Adult (250-450 g) male Wistar rats (n=80) (Charles River Laboratories, Wilmington, MA) were used in this study and initially housed two/cage until after surgery when animals were housed with one animal/cage. In this initial proof-of-concept study (i.e., does N2B IGF-1 reduce trigeminal system (TS) activation from recurrent SD) the inventors have focused to the use of only males. Future work will include females. Housing included use of static micro isolator cages with corn cob bedding, Enviro-dri nesting material (Shepard Specialty Papers, Watertown, TN) and nestlets (Ancare Corporation, Bellmore, NY) for enrichment. Rats were maintained in a 12-hour light-dark cycle with controlled humidity and temperature in the Central Animal Facility. Rats had free access to food and water throughout experiments and were observed at least daily for evidence of normal feeding, grooming and ambulatory activity.

Animals were removed from the central facility for N2B treatment and surgical procedures as described below in the investigators' nearby lab. Once awake after treatment and initial surgery (see below), they were returned to the central animal facility. The next day, animals were again brought to the investigators' lab for induction of SD followed by harvesting of brains. Experiments were performed during the mid-portion of the light cycle. All treatments and data analyses were completed under blinded conditions.

No adverse effects of treatments were seen in any animals consistent with previous work (21,51). All animals continued to feed, groom, ambulate and drink normally.

2. Nose-To-Brain (N2B) Treatment

N2B delivery of 150 µg human recombinant IGF-1 (#191-G1; R&D Systems, Minneapolis, MN) in 50 µL sodium succinate buffer followed the previously described approach (21,51) that was based on the techniques of Liu and coworkers (24) in the recording laboratory under isoflurane anesthesia with spontaneous ventilation.

a. Blood Glucose Analyses

Blood glucose was monitored in a subset of animals. Immediately before N2B treatments and while anesthetized, blood glucose was sampled at time zero using a sterile, 27 gauge hypodermic needle to puncture the tip of the tail. A second drop of blood from punctures was used for glucose measurements (Contour Next EZ; Ascensia Diabetes Care, US, Inc.; Parsippany, NJ). After N2B treatments (IGF-1 or vehicle), animals were briefly re-anesthetized and maintained as above for each blood draw done over time (i.e., 0.3, 3, 6, and 24 hours).

b. Spreading Depression

Figure 4:
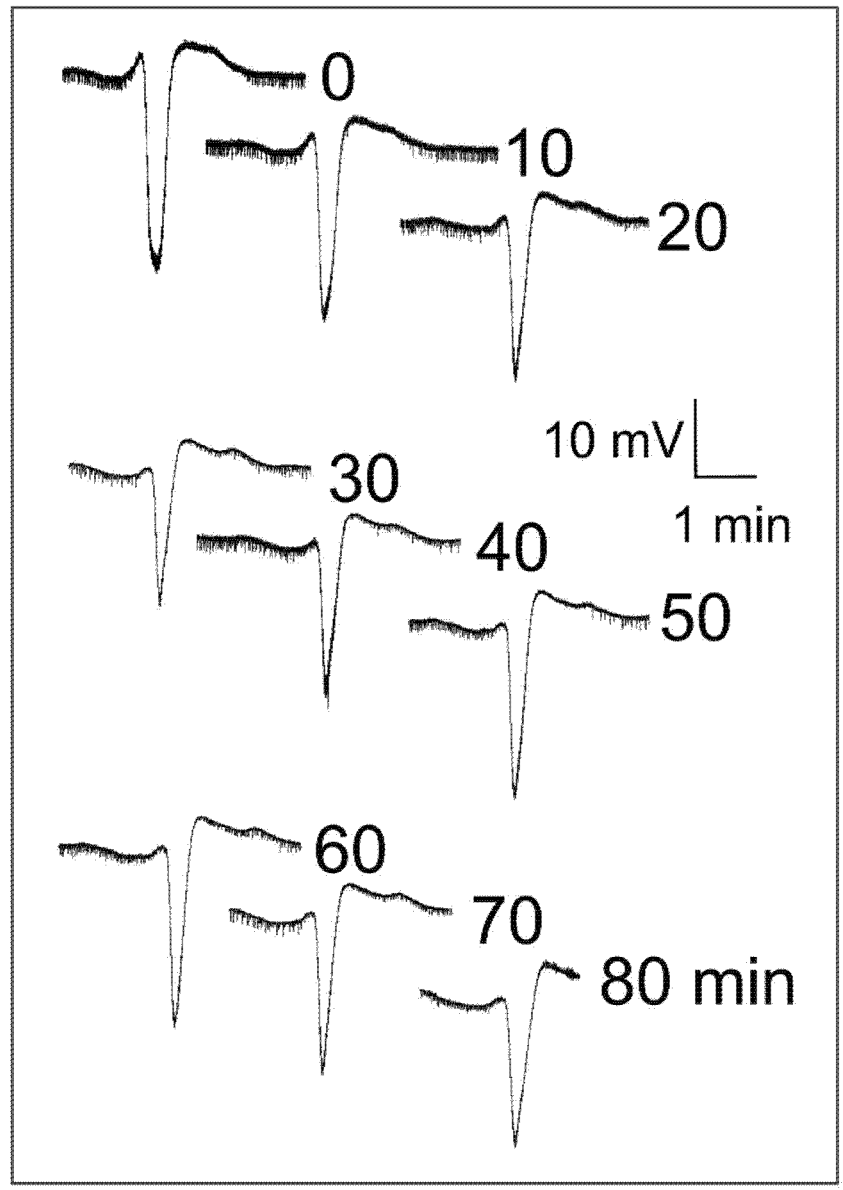
FIG. 4. Representative spreading depression (SD) responses from KCl stimulation. Records show typical large extracellular voltage deflections of SD. Nose to brain administration of IGF-1 (or vehicle) was delivered. Twenty-four hours later, SD was induced every 10 minutes for 90 minutes via pressurized episodic micro-injections of nL quantities of 0.5 M KCl into the rostral neocortex with confirmation of SD established via electrophysiological microelectrode recordings from caudal neocortex. Representative SD slow electrical changes are shown. 10 mV scale bar is negative down. Immediately after SD stimulation, tissues were harvested for determination of the degree of trigeminal system activation in the trigeminal ganglion and caudal trigeminal nucleus.

Induction of recurrent SD followed previously published aseptic techniques from the inventors' laboratory (8, 13, 21, 25, 26, 51) (FIG. 4). Animals were anesthetized with 5% isoflurane, which was later reduced to 1.5% inhalational isoflurane in oxygen during procedures and followed previous procedures for assessing the impact of recurrent SD after pretreatment with N2B IGF-1 (21, 51)).

One day after N2B treatment and surgery, animals were again anesthetized with 5% isoflurane in oxygen that was reduced to 1.5% during recordings of CSD followed by procedures to induce recurrent CSD every 10 minutes for 90 minutes as previously described (FIG. 4) (21,51). CSD was induced using nanoliter injections of 0.5 M KCL through a rostral microelectrode while confirming the occurrence of SD from a second more caudal microelectrode (21,51). At the conclusion of SD induction/recording sessions, animals were more deeply anesthetized with addition of intraperitoneal ketamine/Xylazine, and euthanized by perfusion fixation for harvesting of brains and the trigeminal nerves.

3. Immunostaining

Immunostaining was completed using verified procedures (13, 20-23, 25, 26, 48). The ipsilateral (left) to CSD trigeminal ganglion of each animal was cut into 20 µm thick, consecutive, longitudinal sections using a cryostat (#3050S; Leica, Buffalo Grove, IL) and mounted as one section per gelatin coated slide. Sections containing the V1 (ophthalmic) division of the trigeminal ganglion were identified and three sections, at least 40 µm apart, from each animal were selected for malondialdehyde (MDA), a marker of OS (27), and CGRP immunohistochemistry.

Sections for MDA immunohistochemistry of the trigeminal ganglion were blocked in 10% normal donkey serum containing 0.3% Triton X-100 (diluent buffer) for 1 hour at room temperature and then incubated overnight in primary antibody (Table 1) in diluent buffer at 4° C. Sections were rinsed with PBS and incubated in secondary antibody (Table 1) for 1 hour at room temperature.

For CGRP immunostaining of the trigeminal ganglion, sections were pre-treated with cold acetone (−20° C.) for 10 minutes, rinsed with PBS and then incubated in PBS containing 0.1% Triton X-100 (PBS-T) for 15 minutes. The sections were blocked in 5% normal goat serum/PBS for 1 hour at room temperature before overnight incubation at 4° C. in rabbit anti-CGRP (Table 1) diluted in PBS-T containing 1% bovine serum albumin and 3% normal goat serum. Sections were then incubated in 2° antibody (Table 1) diluted in PBS-T containing 1% bovine serum albumin for 1 hour at room temperature.

For c-fos immunostaining of the trigeminal nucleus, brainstem/cervical spinal cord was cut into 40 µm thick coronal sections using a cryostat. Six consecutive sections were collected every 1.5 mm from the obex (0 mm) caudally through cervical spinal cord (i.e., −1.5 mm, −3.0 mm, −4.5 mm, 6.0 mm) as previously described (8, 26). For each animal, three sections were randomly selected from each brainstem/spinal cord level and processed for c-fos expression. c-fos immunohistochemistry was performed on free floating sections by incubating in 10% normal donkey serum containing 0.3% Triton X-100 for 1 hour at room temperature and then overnight in rabbit anti-c-fos (Table 1) in diluent buffer at 4° C. Sections were rinsed with PBS and incubated in 2o antibody (Table 1) for 1 hour at room temperature. The sections were rinsed with PBS and mounted on gelatin coated slides.

Slides containing immunostained sections were cover-slipped with Prolong™ Gold Antifade mounting media (#P36930; Life Technologies, Eugene, OR). The specificity of the immunolabeling was verified by omission of the primary antibody, using only secondary antibody staining.

4. Computer-Based Digital Image Quantification

The inventors used computer-based and blinded semi-quantitative digital quantification of immunostaining metrics to test the ability of N2B IGF-1 to impact TS activation. To help reduce inter-experiment variability, immunostaining was performed on paired samples (e.g., sham and experimental) sections for all markers (MDA, CGRP and c-fos).

Imaging was performed using a Photometrics self-calibrating digital camera QuantEM-512SC camera (500×500 pixels; Photometrics, Tucson, AZ) run on MetaMorph software (v. 7.0.4; Molecular Devices, Sunnyvale, CA) under blinded conditions (as previously described (13, 20-22). Image exposure, camera gain and thresholding were uniformly set (i.e., equivalently for experimental and sham groups for each imaging metric (i.e., MDA, CGRP and c-fos). Resultant images were digitally stored as TIFF files for subsequent analyses that continued under blinded conditions where image integrated fluorescence intensity was registered using MetaMorph software for MDA and CGRP.

For c-fos image analyses, the 5× digitally stored TIFF files were electronically enlarged to facilitate cell counting to 6,400×6,400 pixels and adjusted for brightness/contrast equivalently between experimental group pairs using Image J (v. 1.43i; National Institutes of Health public access). c-fos labeled nuclei were manually counted by an observer blinded to experimental conditions. Only intensely stained, round or oval-shaped nuclei were counted in lamina I-II [obex through −6.0 mm, recording the average of n=3 sections (technical replicates) at each anatomical level per animal (n≥5 biological replicates/group)].

5. CGRP Plasma Assays

Blood was collected via cardiac puncture using a 21 gauge syringe needle and transferred into a BD Vacutainer K3 EDTA blood collection tube (366450, Becton, Dickinson & Co., Franklin Lakes, NJ). Samples were spun 1,500 g×10 min at 4° C. The plasma was transferred to sterile 2.0 mL, screw cap, polypropylene tubes and stored at −80° C. until analysis. Plasma samples were sent to Cayman Chemical Company (Ann Arbor, Michigan) for analysis of CGRP content using ELISA methods. According to the vendor, the detection limit is <10 pg/mL.

6. Statistical Methods

The inventors used a verified method of quantifying immunostaining ratios (experimental/sham) as a further means to reduce potential run-to-run variations in immunostaining for MDA and CGRP (25) while normalization of cell counts for c-fos positive cells were otherwise used. These maneuvers were highly successful in reducing measurement variability.

Images of MDA and CGRP were analyzed while blinded and later decoded to ratios of experimental/sham image integrated optical intensity, a sensitive metric that not only accounts for the area but also the pixel intensity of related image fluorescence. Immunostaining ratios of 1 indicated no difference between experimental and sham conditions, while a ratio of less than 1 indicates that experimental treatment reduced immunostaining compared to sham. These ratios were converted to natural logarithms whereby 0 corresponded to no difference between experimental and sham conditions, and a t-test (two-tailed) could be used to determine if differences of logarithms varied significantly from 0. In the text, the inventors report p-values and power of related log ratio statistical testing (25). In addition, a more general listing of percent changes in intensity ratios is shown.

c-fos positive cell quantification was also performed under blinded conditions using a verified methodology (8, 26) and others. Since maximal caudal trigeminal nucleus changes in the superficial lamellae are evident at −4.5 mm caudal to the obex, the inventors report quantitative measurements at this level in the text.

Image pairs (experimental and sham) were adjusted equally using Adobe Photoshop, which along with CorelDraw was used for final figure construction. Digital electronic files of SD recordings were processed first in Origin (2019; Microcal, Northhampton, MA) and placed in final form using CorelDraw and Photoshop. Data were analyzed using SigmaPlot software (v. 12.5; Systat Software, Inc. San Jose, CA). All data passed normality testing (p-value to reject: 0.05) and equal variance testing (p=value to reject: 0.05) and power (1-$\beta$: >0.8). Sham controls for c-fos staining were set to 1.00 with experimental data scaled proportionally. Animals groups consisted of ≥5 biological replicates.

C. Results

1. N2B Delivery of IGF-1 does not Trigger Hypoglycemia or TS Activation

To begin exploring how IGF-1 might impact TS activation after SD, the inventors performed a series of preliminary experiments. The inventors confirmed that IGF-1 receptors are widely distributed in the trigeminal ganglion (FIG. 5), consistent with evidence shown previously by others (28).

IGF-1 (Increlex®) is FDA approved only for parenteral treatment of short stature due to primary IGF-1 deficiency in children (29). In this patient population, a subset of children receiving high doses of systemic IGF-1 exhibit hypoglycemia and headache (29). Accordingly, the inventors probed for any impact of N2B IGF-1 on blood glucose levels. In spite of the fact that evidence of radiolabeled IGF-1 can be found in blood after N2B delivery (30), the inventors did not see evidence of hypoglycemia after N2B delivery of IGF-1 (FIG. 6). Specific time-based blood glucose levels (n=8/group at 0 hour and n=4/group otherwise) for succinate buffer (sham) and IGF-1 treated groups were, respectively: 0-hour: 132±11; 0.3-hour: 213±26 and 196±22; 1.0-hour: 167±42 and 139±24; 3.0-hour: 130±30 and 114±14; 6.0-hour: 139±12 and 134±7; 24-hour: 135±12 and 150±40 mg/dL. No significant (p>0.1-0.99) difference between matched time pairs (t-test) was seen. The systematic elevation of blood glucose seen at 0.3 hours was significant (ANOVA, p<0.001, power=1.00), albeit transient over initial level, increases that most likely reflect the expected side effect of exposure to isoflurane anesthesia for the 20 minutes needed for N2B administration (31). The lowest IGF-1 glucose-related level seen was 114 mg/dL [compared to control (132 mg/dL; time 0)], which is within the normal range for Wistar rats [85-132 mg/dL (32)]. While the glucose level that defines hypoglycemia is variable, a drop of 1 mM is not considered hypoglycemic.

Since up to 5% of patients treated systemically with IGF-1 might complain of headache, the inventors probed for evidence of nociceptive TS activation after N2B IGF-1 that could be reflective of headache (FIG. 7). Selected animal studies have shown that systemic administration of IGF-1 can increase peripheral sensory neuron activation (33). However, when directly administered to brain, IGF-1 is anti-nociceptive (34). Accordingly, the inventors used CGRP immunostaining as the metric for trigeminal ganglion activation since CGRP is so widely known for its involvement in TS pain signaling (35). The inventors' results demonstrated for the first time that N2B IGF-1 did not cause an increase in CGRP levels consistent with headache, but instead showed a highly significant 75% decrease in CGRP levels in naïve animals (p<0.001, power=1.00, n=7/group). Specific natural logarithm ratios (IGF-1/sham) were −1.66±0.32 (n=7/group).

Treatment with succinate alone (i.e., log-ratios of succinate/control) showed no significant impact on baseline CGRP levels compared to control animals. Specific log ratios were −0.022±0.19, p=0.916, power=0.052, n=7/group). For these naïve animal CGRP measurements and the measurements of CGRP and MDA in the trigeminal ganglion after SD, the p value is based on comparison of the log-ratio of IGF-1/sham immunostaining integrated intensity versus 0.

2. N2B IGF-1 Inhibits Trigeminal Ganglion Activation after Recurrent SD

Next, the inventors determined how IGF-1 N2B treatment impacted trigeminal ganglion activation after recurrent SD. SD was triggered every ten minutes for a total of nine CSDs. Consistent with the results of Shatillo and coworkers (6), recurrent SD triggered OS in the trigeminal ganglion. However, OS measured via MDA immunostaining in the trigeminal ganglion following recurrent SD, was significantly (p<0.001, power 1.00) reduced by 82% from pretreatment with IGF-1 (FIG. 8). Specific natural logarithm ratios (IGF-1/sham) were −1.37±0.40 (n=5/group). Similarly, pretreatment with N2B IGF-1 caused a significant (p<0.001, power=1.00) reduction in CGRP levels in the trigeminal ganglion after recurrent CSD by 44% (FIG. 9). Specific log-ratio values were −0.90±0.15 (n=5/group). However, no significant (p=0.347, power=0.136) changes in blood CGRP levels were found after pretreatment with IGF-1 (or vehicle) followed by recurrent SD. Specific values were 12.1±3.4 pg/mL, with two samples below the detection limit (n=6/group; vehicle pretreatment) and 7.7±1.6 pg/mL with three samples below the detection limit (n=6/group; IGF-1 pretreatment).

3. N2B IGF-1 Inhibits Caudal Trigeminal Nucleus Activation after Recurrent SD

The inventors (8, 26) and others (5) have shown that recurrent CSD activates neurons in the superficial lamellae of the caudal trigeminal nucleus. The inventors used this trigeminal nucleus activation from CSD to test the impact of pretreatment with N2B delivery of IGF-1 (FIG. 10). Trigeminal nucleus c-fos positive cell counts were less variable from animal to animal such that relative cell counts alone were sufficient to pass normality and equal variance testing. Accordingly, relative cell counts are presented. Results show that N2B pretreatment with IGF-1 caused a significant (p=0.003, power=0.97) 48% reduction of c-fos positive cells in the trigeminal nucleus superficial lamellae at −4.5 mm from the obex. Specific relative cell counts for IGF-1 versus sham controls were 0.52±0.11 versus 1.00±0.06 (n=6/group).

D. Discussion

1. Summary

This study shows that N2B delivery of IGF-1 is a highly effective means to inhibit TS activation associated with migraine modeled in rats using CSD. Importantly, N2B IGF-1 treatment did not evoke hypoglycemia and gave no sign of increased headache, side effects that are seen in some patients given systemic delivery of IGF-1. Instead, IGF-1 caused a significant reduction in naïve levels of trigeminal ganglion cell CGRP. This is the first evidence that a proposed migraine agent can reduce trigeminal ganglion CGRP levels in vivo before this pain-related peptide is released to play a role in nociception. The potential impact of this CGRP reduction before nociceptive activation is enhanced by results that show N2B IGF-1 also significantly reduced TS activation after recurrent CSD.

2. N2B Delivery

N2B delivery of therapeutics is increasingly recognized to be a safe and effective means to treat neurological disorders (36). N2B administered IGF-1 quickly enters the brain within minutes through olfactory, and importantly, trigeminal routes. Evidence shows that N2B delivery of IGF-1 is protective against brain cell death, reducing the size of infarction from ischemia (24). N2B IGF-1 delivery also has a significantly positive influence on brain function since it can reduce neuronal hyperexcitability. Here the inventors extended this quieting impact of IGF-1 on neuronal electrical activity by showing N2B IGF-1 similarly abrogates the increased neuronal activation of the TS from recurrent SD.

IGF-1 passes into the brain along the olfactory and trigeminal nerves to the cerebrospinal fluid (30, 37). Soluble agents then appear to move rapidly through the cerebrospinal fluid space by bulk flow and into the brain parenchyma via flow from perivascular spaces (30, 37). This proposed route of entry is supported by biodistribution studies (30, 37).

The Thorne laboratory has studied biodistribution of radiolabeled IGF-1 after N2B delivery (30). It is notable that, following N2B delivery, the highest levels of tracer were seen in the trigeminal ganglion. The levels in the trigeminal ganglion are ~10-fold greater than levels in the olfactory bulb (30) within 30 minutes of administration. Many have questioned the translational utility of extrapolating N2B delivery data from rats to humans. This concern stems from differences between rodents and humans in nasal structure and olfactory mucosa size where delivered agents would be expected to cross. Perhaps this singular focus of N2B delivery needs to be expanded to more actively examine the potential role of the trigeminal nerves. In fact, focus to the trigeminal nerve and TS as the conduit to the brain from N2B delivery of therapeutics may be especially well-suited to developing migraine therapeutics since the trigeminal ganglion is the "first stop" along N2B-related passage way to the brain.

3. IGF-1 and Oxidative Stress

Delineation of mechanisms by which IGF-1 reduces OS in the trigeminal ganglion is beyond the scope of this work. However, some direction can be provided from the existing literature to suggest a potential mechanism.

The inventors noted above that patients with migraine show increased brain electrical excitability compared to non-migraineur counterparts (1) along with increased levels of OS (2, 3). Since hyperexcitability enhances OS and OS promotes hyperexcitability, unraveling this vicious cycle in the brain as it relates to initiation of migraine, but also activation of the TS, seems to be a promising strategy for new migraine therapeutics development. However, important differences in the source of OS and impact of IGF-1 on mitigating OS may be involved. Such differences may contribute to the overall utility of IGF-1 as a potential migraine therapeutic. SD evoked by hyperexcitability from recurrent electrical stimulation requires microglia and their activation to promote release of the pro-inflammatory cytokine tumor necrosis factor alpha and reactive oxygen species, which together help to initiate SD (13, 19, 20). Conversely, treatment with IGF-1 abrogates this microglial OS and inflammatory activation and in so doing inhibits initiation of SD (19, 20).

In contrast, OS in the trigeminal ganglion after recurrent CSD involves cells that morphologically resemble neurons with increased MDA, a product of lipid peroxidation (6). This enhanced production of MDA in the TS is so robust that it can be detected in the blood of migraine patients (2, 3) suggesting its use as a potential biomarker for migraine treatment. Activated neurons generate reactive oxygen species, which can result in OS if reactive oxygen species generation exceeds anti-oxidant levels. Given that mitochondria are concentrated in neurons, MDA can cause mitochondrial dysfunction which can directly promote production of reactive oxygen species (38). Notably, N2B IGF-1 reduced trigeminal ganglion MDA levels by 82% (FIG. 7). Furthermore, using brain slice cultures in vitro, the inventors show that OS from menadione exposure, a mitochondrial inhibitor, is significantly reduced by IGF-1 (19, 20). In fact, IGF-1 reduces naïve culture levels of reactive oxygen species significantly below that of controls [FIG. 7, (20)]. This leads us to hypothesize that a principle means by which N2B IGF-1 may inhibit MDA levels in the trigeminal ganglion after recurrent SD is likely to involve effects on mitochondrial function.

4. IGF-I Interactions with CGRP

OS, including that from mitochondrial dysfunction, may also be a key stimulus for increased CGRP production. Using various preclinical models, others have shown that trigeminal ganglion CGRP levels and related c-fos activation in the caudal trigeminal nucleus after induction of migraine and therapeutic treatments are similar to the protective 44% and 48% effects, respectively, reported here (7, 39-43).

What then might be potential advantages of N2B IGF-1? First, N2B IGF-1 effectively prevents SD ~27-fold over sham treatment (21) in comparison to pretreatment with topiramate, for example, which provides no more than a two-fold level of protection (44) against SD from KCl. KCl injection volumes here were increased to supra-threshold amounts (i.e., ~10-fold higher than that needed to induce SD) to ensure that SD occurred and TS activation could be reliably measured. Thus, actual protection against CSD and TS activation may be higher than that reported here due to inhibition of SD. Second, this is the first work to show that treatment with a putative migraine therapeutic can significantly reduce (e.g., 75%) naïve levels of trigeminal ganglion CGRP—before it is released to be involved in migraine pain. These results prompt us to suggest that N2B IGF-1 is involved in stopping the cause (i.e., brain hyperexcitability needed to evoke SD and trigeminal ganglion CGRP before it is released to trigger pain) as well as the consequences of migraine modeled in animals (i.e., increased expression of trigeminal ganglion OS and CGRP and trigeminal nucleus c-fos).

A third potential advantage to N2B IGF-1 treatment follows from work from the Burstein laboratory. Melo-Carillo show that anti-CGRP agents selectively block Aδ trigeminal electrical activity and related high threshold trigeminal nucleus neurons (45). In contrast, C-fibers, which contain CGRP and activate wide dynamic range neurons in the trigeminal nucleus, are not inhibited. The authors suggest this partial impact on the TS may account for the partial efficacy seen in treatment of migraine patients with anti-CGRP agents (45). Perhaps, N2B IGF-1 treatment will have more widespread effects because of its more global impact on migraine-related pathophysiology.

A fourth and perhaps the most important potential advantage to N2B IGF-1 treatment for migraine involves the ability of IGF-1 to reduce OS. Reactive oxygen species promote TS nociceptive activation via TRPA1 channel activation (6). Increased TRPA1 signaling promotes SD, suggesting that TRPA1 channel blockade may be a potential target for improved migraine treatment due to an ability to reduce OS (41). Most existing prophylactic migraine agents show some degree of anti-oxidant effect (46, 47) providing further support for targeting OS in migraine treatment. However, while TRPA1 channels appear to be a promising target for therapeutics development, considerable hurdles remain (47). In contrast, N2B IGF-1 showed blockade of OS, like that hoped for with TRPA1 channel blockade, including an 82% reduction in trigeminal ganglion MDA levels after recurrent SD.

5. Conclusion

Increased production of IGF-1 is a naturally occurring adaptive response to EE in animals, which is protective against modeled migraine. As a result, it may have a high benefit/risk ratio as a therapeutic for brain, especially when delivered phasically, consistent with the basic tenet of EE-based science (i.e., physiological stress followed by an adaptation period, cycled repeatedly (48) if it can be translated to the human condition. IGF-1 seems particularly well-suited for N2B delivery for migraine because of the likely dominant entry pathway via the trigeminal nerve. As a result, N2B IGF-1 delivery not only reduces brain susceptibility to migraine (modeled using SD), hyperexcitability and TS activation, but also results in decreased OS and TS CGRP levels. Perhaps N2B IGF-1 will mitigate the depletion of antioxidants seen in migraine that leads to worsening of this disorder (2, 3, 49, 50).

Important Points: 1) Migraineurs show brain hyperexcitability and increased oxidative stress. 2) Since hyperexcitability enhances oxidative stress and oxidative stress promotes hyperexcitability, ending this feed-back loop may lead to new therapeutics for migraine. 3) Other works shows that IGF-1 protects against spreading depression after nose-to-brain administration in vivo to adult rats. 4) This study shows that similar treatment inhibits trigeminal system activation associated with migraine modeled in rats. 5) This data provides strong evidence to indicate that nose-to-brain IGF-1 mitigates not only the hyperexcitability-related cause of migraine modeled in animals, but also the nociceptive consequences in the trigeminal system.

TABLE 1

Description of antibodies used for immunohistochemistry

| | Name | Catalog # | Host | Dilution | Detects | Supplier |
|---|---|---|---|---|---|---|
| 1° Ab | c-fos | ABE457 | rabbit | 1/10,000 | N-terminus of c-fos | Millipore, Temecula, CA |
| | CGRP | C8198 | rabbit | 1/1,000 | rat CGRP | Sigma, St. Louis, MO |
| | MDA | ab6463 | rabbit | 1/500 | rat MDA | AbCam, Cambridge, MA |

| | Name | Catalog # | Against | Dilution | Supplier |
|---|---|---|---|---|---|
| 2° Ab | Alexa 594 (goat) | ab150084 | rabbit | 1/500 (CGRP) 1/700 (c-fos, MDA) | AbCam, Cambridge, MA |

E. References

The following references, to the extent that they provide exemplary procedural or other details supplementary to those set forth herein, are specifically incorporated herein by reference.

1. Aurora S K, Cao Y, Bowyer S M, et al. The occipital cortex is hyperexcitable in migraine: experimental evidence. Headache. 1999; 39: 469-476.
2. Bernecker C, Ragginer C, Fauler G, et al. Oxidative stress is associated with migraine and migraine-related metabolic risk in females. Eur J Neurol. 2011; 18: 1233-1239.
3. Tuncel D, Tolun F I, Gokce M, et al. Oxidative stress in migraine with and without aura. Biol Trace Elem Res. 2008; 126: 92-97.
4. Borkum J M. Migraine triggers and oxidative stress: A narrative review and synthesis. Headache. 2016; 56: 12-35.
5. Goadsby P J, Holland P R, Martins-Oliveira M, et al. Pathophysiology of migraine: A disorder of sensory processing. Physiol Rev. 2017; 97: 553-622.
6. Shatillo A, Koroleva K, Giniatullina R, et al. Cortical spreading depression induces oxidative stress in the trigeminal nociceptive system. Neuroscience. 2013; 253: 341-349.
7. Chen S P and Ayata C. Spreading depression in primary and secondary headache disorders. Curr Pain Headache Rep. 2016; 20: 44.
8. Moskowitz M A, Nozaki K and Kraig R P. Neocortical spreading depression provokes the expression of c-fos protein-like immunoreactivity within trigeminal nucleus caudalis via trigeminovascular mechanisms. J Neurosci. 1993; 13: 1167-1177.
9. Mitsikostas D D and Sanchez del Rio M. Receptor systems mediating c-fos expression within trigeminal nucleus caudalis in animal models of migraine. Brain Res Brain Res Rev. 2001; 35: 20-35.
10. Hansen J M, Thomsen L L, Olesen J, et al. Calcitonin gene-related peptide does not cause migraine attacks in patients with familial hemiplegic migraine. Headache. 2011; 51: 544-553.
11. Messlinger K, Lennerz J K, Eberhardt M, et al. CGRP and NO in the trigeminal system: mechanisms and role in headache generation. Headache. 2012; 52: 1411-1427.

12. Mitsikostas D D and Reuter U. Calcitonin gene-related peptide monoclonal antibodies for migraine prevention: comparisons across randomized controlled studies. Curr Opin Neurol. 2017; 30: 272-280.
13. Pusic K M, Pusic A D, Kemme J, et al. Spreading depression requires microglia and is decreased by their M2a polarization from environmental enrichment. Glia. 2014; 62: 1176-1194.
14. Irby M B, Bond D S, Lipton R B, et al. Aerobic exercise for reducing migraine burden: mechanisms, markers, and models of change processes. Headache. 2016; 56: 357-369.
15. Lemmens J, De Pauw J, Van Soom T, et al. The effect of aerobic exercise on the number of migraine days, duration and pain intensity in migraine: a systematic literature review and meta-analysis. J Headache Pain. 2019; 20: 16.
16. Ciucci F, Putignano E, Baroncelli L, et al. Insulin-like growth factor 1 (IGF-1) mediates the effects of enriched environment (EE) on visual cortical development. PLoS One. 2007; 2: e475.
17. Brown S M, Peters R and Lawrence A B. Up-regulation of IGF-1 in the frontal cortex of piglets exposed to an environmentally enriched arena. Physiol Behav. 2017; 173: 285-292.
18. Nishijima T, Piriz J, Duflot S, et al. Neuronal activity drives localized blood-brain-barrier transport of serum insulin-like growth factor-I into the CNS. Neuron. 2010; 67: 834-846.
19. Grinberg Y Y, Dibbern M E, Levasseur V A, et al. Insulin-like growth factor-1 abrogates microglial oxidative stress and TNF-alpha responses to spreading depression. J Neurochem. 2013; 126: 662-672.
20. Grinberg Y Y, van Drongelen W and Kraig R P. Insulin-like growth factor-1 lowers spreading depression susceptibility and reduces oxidative stress. J Neurochem. 2012; 122: 221-229.
21. Grinberg Y Y, Zitzow L A and Kraig R P. Intranasally administered IGF-1 inhibits spreading depression in vivo. Brain Res. 2017; 1677: 47-57.
22. Won L and Kraig R P. Nose-to-brain delivery of IGF-1 abrogates trigeminal system activation including oxidative stress and CGRP from recurrent spreading depression. Soc Neurosci. 2019; in press.
23. Won L and Kraig R P. Development of nasal insulin-like growth factor-1 as a novel treatment for migraine. Am Headache Soc. 2019; in press.
24. Liu X F, Fawcett J R, Thorne R G, et al. Intranasal administration of insulin-like growth factor-I bypasses the blood-brain barrier and protects against focal cerebral ischemic damage. J Neurol Sci. 2001; 187: 91-97.
25. Kraig R P, Dong L M, Thisted R, et al. Spreading depression increases immunohistochemical staining of glial fibrillary acidic protein. J Neurosci. 1991; 11: 2187-2198.
26. Kunkler P E and Kraig R P. Hippocampal spreading depression bilaterally activates the caudal trigeminal nucleus in rodents. Hippocampus. 2003; 13: 835-844.
27. Chen S P, Qin T, Seidel J L, et al. Inhibition of the P2X7-PANX1 complex suppresses spreading depolarization and neuroinflammation. Brain. 2017; 140: 1643-1656.
28. Wang H, Qin J, Gong S, et al. Insulin-like growth factor-1 receptor-mediated inhibition of A-type K(+) current induces sensory neuronal hyperexcitability through the phosphatidylinositol 3-kinase and extracellular signal-regulated kinase 1/2 pathways, independently of Akt. Endocrinology. 2014; 155: 168-179.
29. Ipsen Biopharmaceuticals I. INCRELEX, http://www.increlex.com/pdf/patient-full-prescribing-information.pdf (2016).
30. Thorne R G, Pronk G J, Padmanabhan V, et al. Delivery of insulin-like growth factor-I to the rat brain and spinal cord along olfactory and trigeminal pathways following intranasal administration. Neuroscience. 2004; 127: 481-496.
31. Zuurbier C J, Keijzers P J, Koeman A, et al. Anesthesia's effects on plasma glucose and insulin and cardiac hexokinase at similar hemodynamics and without major surgical stress in fed rats. Anesth Analg. 2008; 106: 135-142.
32. Kohn D F and Clifford C B. Biology and diseases of rats. In: Fox J G, Anderson L C, Lowe F M and Quimby F, (eds.). Laboratory Animal Medicine. second ed. New York: Academic Press, 2002, p. 121-167.
33. Zhang Y, Qin W, Qian Z, et al. Peripheral pain is enhanced by insulin-like growth factor 1 through a G protein-mediated stimulation of T-type calcium channels. Sci Signal. 2014; 7: ra94.
34. Bitar M S, Al-Bustan M, Nehme C L, et al. Antinociceptive action of intrathecally administered IGF-I and the expression of its receptor in rat spinal cord. Brain Res. 1996; 737: 292-294.
35. Russo A F. Calcitonin gene-related peptide (CGRP): a new target for migraine. Annu Rev Pharmacol Toxicol. 2015; 55: 533-552.
36. Djupesland P G, Messina J C and Mahmoud R A. The nasal approach to delivering treatment for brain diseases: an anatomic, physiologic, and delivery technology overview. Ther Deliv. 2014; 5: 709-733.
37. Lochhead J J, Wolak D J, Pizzo M E, et al. Rapid transport within cerebral perivascular spaces underlies widespread tracer distribution in the brain after intranasal administration. J Cereb Blood Flow Metab. 2015; 35: 371-381.
38. Long J, Liu C, Sun L, et al. Neuronal mitochondrial toxicity of malondialdehyde: inhibitory effects on respiratory function and enzyme activities in rat brain mitochondria. Neurochem Res. 2009; 34: 786-794.
39. Filiz A, Tepe N, Eftekhari S, et al. CGRP receptor antagonist MK-8825 attenuates cortical spreading depression induced pain behavior. Cephalalgia. 2019; 39: 354-365.
40. Greco M C, Capuano A, Navarra P, et al. Lacosamide inhibits calcitonin gene-related peptide production and release at trigeminal level in the rat. Eur J Pain. 2016; 20: 959-966.
41. Jiang L, Ma D, Grubb B D, et al. ROS/TRPA1/CGRP signaling mediates cortical spreading depression. J Headache Pain. 2019; 20: 25.
42. Ramachandran R, Bhatt D K, Ploug K B, et al. Nitric oxide synthase, calcitonin gene-related peptide and NK-1 receptor mechanisms are involved in GTN-induced neuronal activation. Cephalalgia. 2014; 34: 136-147.
43. Sixt M L, Messlinger K and Fischer M J. Calcitonin gene-related peptide receptor antagonist olcegepant acts in the spinal trigeminal nucleus. Brain. 2009; 132: 3134-3141.
44. Ayata C, Jin H, Kudo C, et al. Suppression of cortical spreading depression in migraine prophylaxis. Ann Neurol. 2006; 59: 652-661.
45. Melo-Carrillo A, Noseda R, Nir R R, et al. Selective inhibition of trigeminovascular neurons by fremanezumab: A humanized monoclonal anti-CGRP antibody. J Neurosci. 2017; 37: 7149-7163.

46. Benemei S and Dussor G. TRP channels and migraine: Recent developments and new therapeutic opportunities. Pharmaceuticals (Basel). 2019; 12.
47. Skerratt S. Recent progress in the discovery and development of TRPA1 modulators. Prog Med Chem. 2017; 56: 81-115.
48. Kraig R P, Mitchell H M, Christie-Pope B, et al. TNF-alpha and microglial hormetic involvement in neurological health & migraine. Dose Response. 2010; 8: 389-413.
49. Aytac B, Coskun O, Alioglu B, et al. Decreased antioxidant status in migraine patients with brain white matter hyperintensities. Neurol Sci. 2014; 35: 1925-1929.
50. Malkki H. Headache: Chronic migraine linked to reduced antioxidant capacity. Nat Rev Neurol. 2015; 11: 426.
51. Won L, Kraig R P. (2020) Insulin-like growth factor-1 inhibits spreading depression-induced trigeminal calcitonin gene related peptide, oxidative stress & neuronal activation in rat. Brain Res. 1732:146673. doi: 10.1016/j.brainres.2020.146673. Epub 2020 Jan. 21. PMID: 31978377. PMCID: 6733989.

Example 3

Nose-To-Brain Insulin-Like Growth Factor-1 Abrogates Trigeminal System Activation from Spreading Depression Migraine is a health care burden in need of improved therapeutics. This void has begun to be filled by focus on calcitonin gene related peptide (CGRP), an inflammatory molecule released from the trigeminal system (TS) with migraine. New anti-CGRP drugs are antibodies designed to inhibit or absorb circulating CGRP to block nociceptive activation of the TS. As such, they do not influence the cause [i.e., underlying brain hyperexcitability (HE) and TS over activity] of migraine, but instead influence the consequence (i.e., CGRP release) which might account for their partial impact on migraine.

The inventors showed that IGF-1 reduces brain HE associated with migraine modeled using spreading depression (SD) in brain slice cultures. Furthermore, nose-to-brain (N2B) delivery of IGF-1 protects against SD in whole animals. Here the inventors extend that work to determine the impact of N2B IGF-1 pretreatment a day before recurrent SD on TS activation. N2B IGF-1 significantly reduced (p<0.001) SD-induced trigeminal ganglion oxidative stress [(OS), measured via malondialdehyde immunostaining] and immunostaining for CGRP by 82% and 44%, respectively. In fact, IGF-1 reduced CGRP in the trigeminal ganglion of naïve animals (without SD activation) by 75% compared to vehicle. Thus, N2B IGF-1 treatment does not appear to induce headache, a concern from systemic use of IGF-1. Also, N2B IGF-1 showed no evidence of hypoglycemia. Finally N2B administration of IGF-1 significantly (p=0.003) reduced caudal trigeminal nucleus activation (i.e., c-fos immunostaining).

These results show for the first time that N2B IGF-1 is an effective means to abrogate TS activation associated with migraine (modeled using SD). This delivery method may be well-suited for translation to the human condition. Furthermore, while specific mechanisms for the protective impact of N2B IGF-1 treatment for migraine remain to be determined, the inventors' data strongly support blocking OS as a key mechanism. Perhaps N2B IGF-1 will mitigate the depletion of antioxidants seen in migraine patients that leads to worsening of this disorder.

A. Background

Migraineurs show brain hyperexcitability and increased oxidative stress (OS). Since hyperexcitability enhances OS and OS promotes hyperexcitability, ending this feed-back loop may lead to novel therapeutics for migraine. Spreading depression (SD), the most likely cause of migraine aura and perhaps pain, triggers OS not only in the cortical area involved in SD, but also in the trigeminal system, a locus important to pain pathway activation in migraine. OS increases the release of trigeminal calcitonin gene-related peptide (CGRP), an inflammatory neuropeptide associated with nociception, and OS can reduce SD threshold.

The inventors have shown that insulin-like growth factor-1 (IGF-1) significantly protects against spreading depression in vitro by reducing oxidative stress. Additionally, IGF-1 significantly protects against spreading depression after intranasal administration in vivo to adult rats (FIG. 11).

Current migraine therapeutics offer only fractional protection and thus there is an unmet need for agents to treat migraineurs more effectively. The inventors are developing intranasal IGF-1 as a novel migraine therapeutic.

Given that IGF-1 is significantly neuroprotective against SD in vitro and in vivo, this work is extended to determine the impact of intranasal IGF-1 on SD activation of the trigeminal system where IGF-1 receptors are abundantly expressed.

This work provides strong evidence to indicate that nasal delivery of IGF-1 can mitigate not only the spreading depression related cause of migraine modeled in animals, but it Is also an effective means to abrogate trigeminal system activation associated with migraine.

B. Methods

Paradigm (FIG. 12) for study of the impact of intranasal delivery of human recombinant IGF-1 on trigeminal system activation after spreading depression (SD). (A) IGF-1 (150 mg/mL) [or vehicle (sham)] was administered to rats over 20 minutes in a recumbent position while under inhalational isoflurane anesthesia. (B) 24 hours later, SD was induced every 9-10 minutes for 90 minutes via pressurized episodic micro-injections of nL amounts of 0.5 M KCl into rostral neocortex with confirmation of SD established via electrophysiological microelectrode recordings from caudal neocortex. Representative SDs are shown. Immediately after SD, tissues were harvested for immunostaining assessment of trigeminal system activation in the trigeminal ganglion using OS lipid peroxidation marker, malondialdehyde, and CGRP (C) and c-fos in the caudal trigeminal nucleus (D).

C. Results

Figure 13:
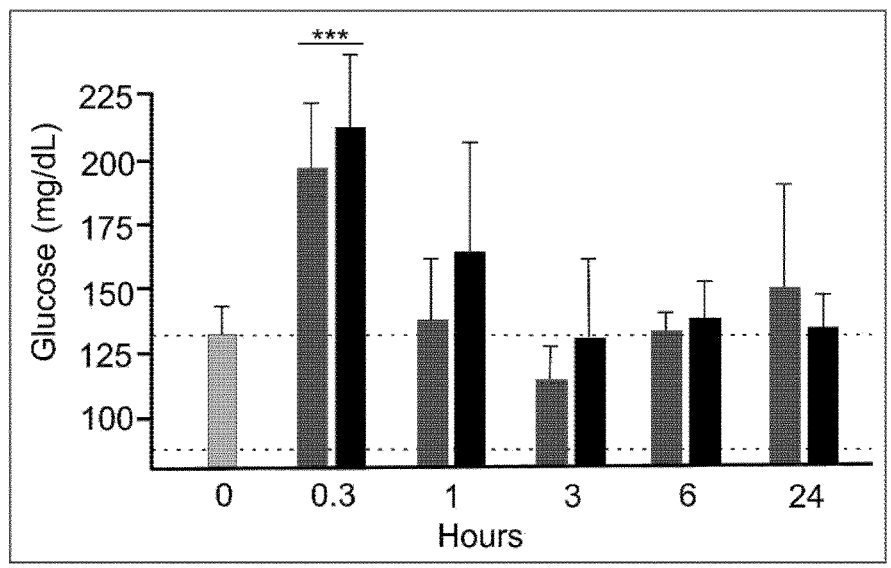
FIG. 13. Systemic administration of IGF-1 did not trigger hypoglycemia.

Systemic administration of IGF-1 for treatment of short stature can trigger hypoglycemia and headache, however the inventors found no evidence for either effect. Nasal delivery of IGF-1 did not cause hypoglycemia (FIG. 13). Dotted lines show normal glucose range in adult non-fasted rats. No significant difference (n=4/group) was seen between sham (vehicle; black) and IGF-1 treated (red) treated groups (t-test). As expected, glucose briefly increased significantly (***p<0.001) from the protracted 20 minutes of anesthesia used to administer nasal treatments.

Nasal administration of IGF-1 caused a significant (75%, $p<0.001$, $n=7$/group) decline in basal expression of trigeminal ganglion CGRP compared to sham. Representative images are shown in FIG. 1 [(IGF-1 (right), sham, (left); scale bar=25 μm]. These results strongly suggest that nasal treatment with IGF-1 will not trigger headache.

Figure 14:
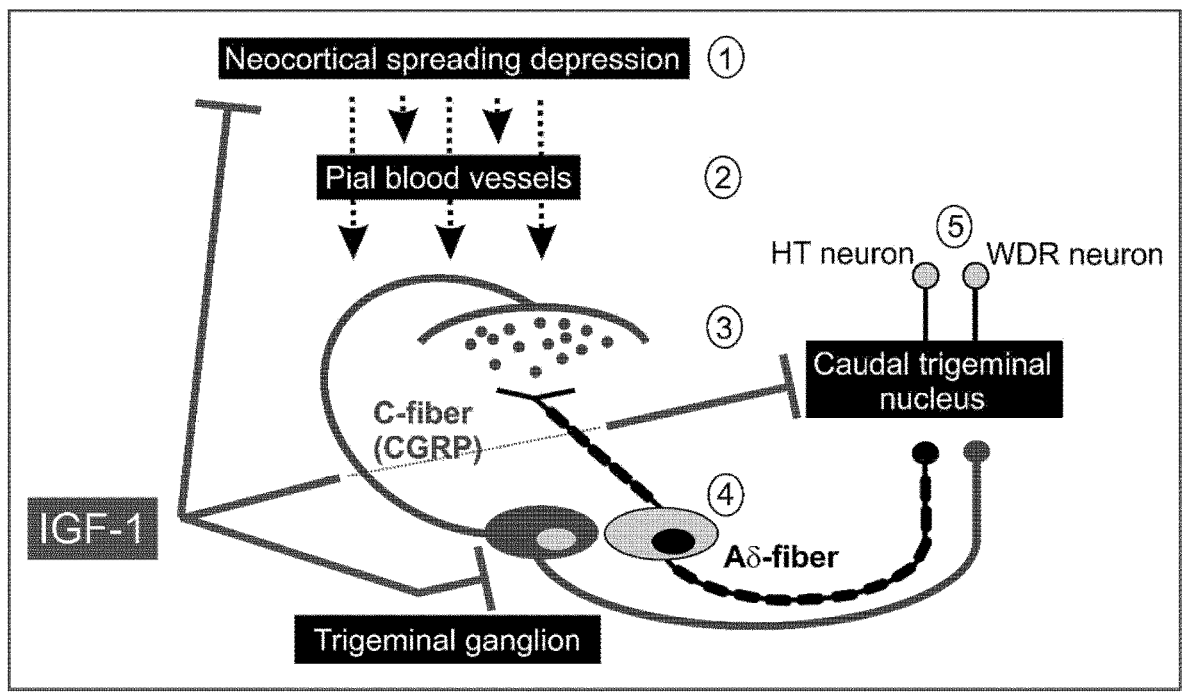
FIG. 14. Schematic adapted from Melo-Carrillo et al. (JNS, 2019) illustrates that nasal IGF-1 may impact migraine at multiple levels.

The inventors next probed for the impact of nasal IGF-1 (versus sham) on activation of the trigeminal ganglion [OS (malondialdehyde) and CGRP)] as well as the caudal trigeminal nucleus (c-fos) after 90 minute of recurrent SD ($n=5$-$7$/group). In all cases a significant reduction (*$p<0.001$ or $p<0.01$) was seen with IGF-1 treatment Representative images are shown below. FIGS. 8-10: IGF-1 (A) and sham (B), scale bar=25 μm. FIG. 14 shows a schematic adapted from Melo-Carrillo et al. (JNS, 2019) illustrates that nasal IGF-1 may impact migraine at multiple levels.

Example 4

Development of Nasal Insulin-Like Growth Factor-1 as a Novel Treatment for Migraine Background: Migraine is an immense health care burden. Existing therapeutics for high frequency and chronic migraine are often used off-label and offer only fractional protection, perhaps because they do not effectively impact migraine pathophysiology.

CNS hyperexcitability (HE) occurs in migraine patients along with increased levels of oxidative stress (OS). Since HE enhances OS and OS promotes HE, uncoupling this CNS cycle, especially as it relates to the trigeminal system (TS), may lead to novel therapeutics for migraine. Spreading depression (SD), the most likely cause of migraine aura and perhaps pain, triggers OS not only in the cortical area involved in SD, but also the TS, a locus important to pain pathway activation in migraine. OS increases calcitonin gene-related peptide (CGRP) release in the TS system. Furthermore, TRPA1 channel blockade is increasingly emphasized as a potential target for migraine because of the ability to reduce OS, though problems have hampered this development.

Recently, anti-CGRP biologics show promise by blocking nociception after CGRP release. However, treated patients still experience frequent migraines and these drugs do not prevent the root cause of migraine. Thus, there is an unmet need for therapeutics to treat frequent migraine sufferers more effectively.

Objective: The inventors are developing nose-to-brain (N2B) insulin-like growth factor-1 (IGF-1) as a novel migraine therapeutic. Physical and intellectual activity (termed EE) reduces susceptibility to SD. In humans, increased physical activity reduces susceptibility to migraine. IGF-1 rises with environmental enrichment (EE) and enters brain with sensory stimulation. The inventors previously showed that IGF-1 is significantly protective against SD using in vitro and in vivo models of migraine. This effect involves abrogation of microglial activation and OS, which triggers the HE burst needed to initiate SD. Additionally, N2B IGF-1 significantly protects against SD in rats.

Methods/Results: Here the inventors show that N2B pre-treatment with IGF-1 also significantly ($p<0.001$) reduced TS activation (as evidenced by trigeminal ganglion OS and CGRP levels; $n \geq 5$/group) plus trigeminal caudal nucleus activation after recurrent SD ($p<0.003$). Importantly, N2B IGF-1 reduces naïve levels of CGRP by 75% in the trigeminal ganglion while at the same time having no hypoglycemic effect. Given that systemic delivery of IGF-1 for short stature shows $\geq 5$% incidence of headache and a more frequent incidence of hypoglycemia, these latter results support the utility of direct N2B delivery of IGF-1.

Conclusion: N2B IGF-1 delivery is an effective means to inhibit not only the HE involved in triggering migraine (modeled here as SD), but also TS activation that includes CGRP before it is released to cause pain. Thus, N2B IGF-1 may act on the causes and not only the consequences (i.e., CGRP release) of migraine. Since highest levels of IGF-1 occur at the trigeminal ganglion after N2B IGF-1 in rodents, this delivery method may be well-suited for translation to the human condition. IGF-1 is a naturally occurring EE-mimetic that might fulfill the promise of reducing brain and TS OS related to the hyperexcitability of migraine and in so doing present a novel therapeutic for this malady.

Example 5

Probing for Synergy Against Migraine Modeled in Rats Using Combined Anti-CGRP-mAb and IGF-1

The inventors hypothesized that the addition of insulin-like growth factor-1 (IGF-1) will significantly improve the efficacy of anti-CGRP-mAbs as migraine therapeutics. CNS hyperexcitability occurs in migraine patients along with increased levels of oxidative stress. Since hyperexcitability enhances oxidative stress and oxidative stress promotes hyperexcitability, unraveling this CNS vicious cycle especially as it relates to the trigeminal system may lead to novel therapeutics for migraine. Cortical spreading depression (CSD), the most likely cause of migraine aura and perhaps pain, triggers oxidative stress not only in the cortical areas involved in CSD, but also in the trigeminal pathway, important to pain pathway activation in migraine. Oxidative stress can cause increased CGRP in the trigeminal ganglion and oxidative stress can reduce CSD threshold.

IGF-1 reduces the hyperexcitability and oxidative stress needed to trigger CSD, and the inventors reasoned that the hyperexcitability and oxidative stress known to occur in the trigeminal system with models of migraine. This work is based on research into understanding how increased physical and intellectual activity [i.e., environmental enrichment (EE)] reduces susceptibility to CSD. In humans, increased physical activity reduces susceptibility to migraine. IGF-1 increases with environmental enrichment and enters brain with increased neural activity from sensory stimulation. Using both in vitro and in vivo models of migraine, the inventors show that IGF-1 is significantly protective against CSD. This effect involves abrogation of microglial-derived oxidative stress, which otherwise triggers the hyperexcitability burst needed to initiate CSD. Also, IGF-1 significantly protects against CSD after nasal administration (which includes direct nose-to-brain delivery) in vivo to adult rats (Grinberg et al., 2017).

Figure 15:
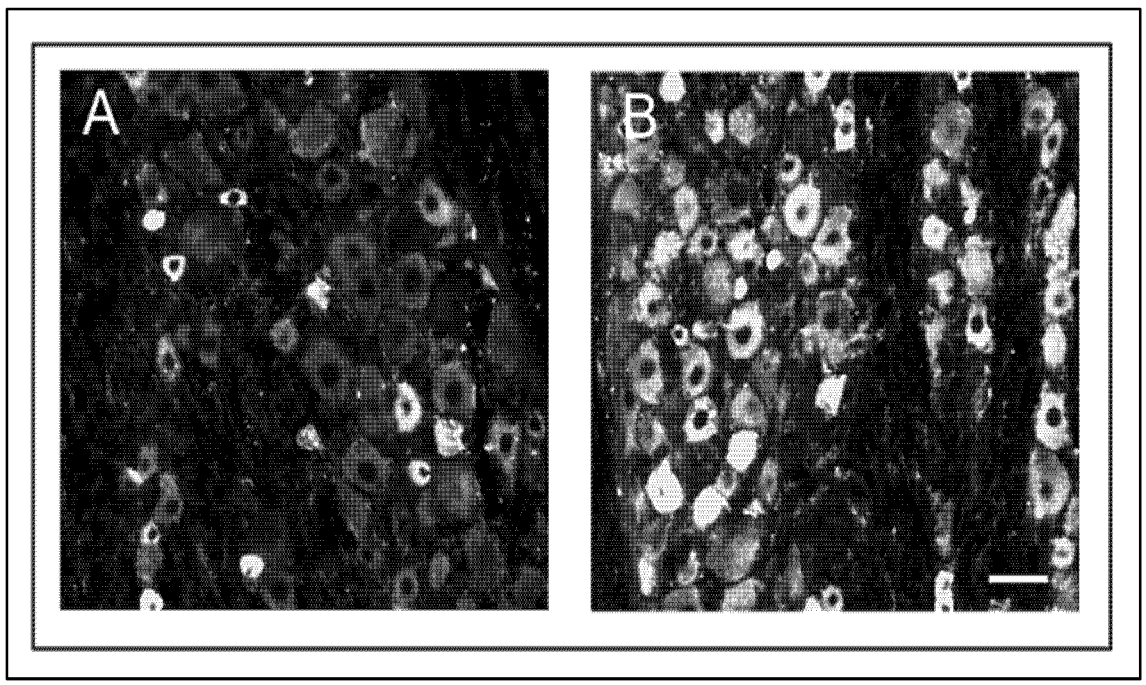
FIG. 15A-B. Intranasal delivery of IGF-1 significantly reduces CGRP levels in the trigeminal ganglion of naïve animals. Rats (n=5/group) were anesthetized with isoflurane and treated with succinate buffer (sham) or IGF-1 (150 µg) in 50 µl. 24 hours later animals were re-anesthetized, brains harvested and processed for CGRP immunostaining of the trigeminal ganglion. Images were obtained from each animal and image fluorescence intensity quantified via a digital imaging strategy. Three images were measured per animal and the averages recorded. Nasal delivery and image processing was completed while blinded to conditions. Experiments, immunostaining and imaging were done in pairs (i.e., sham and IGF-1) to reduce potential variability. Staining ratios (IGF-1/sham) were converted to natural logs so that 0 corresponded to no difference and a value less than 0 meant IGF-1 reduced CGRP and so that a t-test could be used to determine if difference in logs varied significantly from 0 (Kraig et al., J Neurosci, 1991). Representative images show CGRP immunostaining of the V1 area of the trigeminal ganglion after treatment with (A) IGF-1 or (B) vehicle. Natural log ratio levels of immunostaining levels after intranasal treatment (IGF-1/sham) showed that IGF-1 significantly (p<0.001) reduced CGRP levels, a 75% reduction. Scale bar=25 µm. Data from Won and Kraig, 2020.

The inventors have shown that nasal administration of IGF-1 significantly reduced naïve levels of CGRP in the trigeminal ganglion by ~75% (FIG. 15). The inventors have now also shown that nasal administration of IGF-1 also significantly reduced trigeminal system activation from recurrent CSD.

Accordingly, the inventors sought to define the degree to which combined treatment with intravenous administration of mouse anti-rat CGRP (ab81887 [4901]; Zeller et al., 2008) and nasal IGF-1 mitigates trigeminal system activation compared to either agent alone. This work will be done using recurrent CSD (Grinberg et al., 2017, Won and Kraig, 2019a,b, 2020). The primary objectives are to determine trigeminal ganglion levels of activation [i.e., CGRP and oxidative stress (malondialdehyde) levels] and to determine parallel measurements of trigeminocervical complex activation (i.e., c-fos).

The inventors have completed a full-length study examining the ability of nasal delivery of IGF-1 to reduce trigeminal system activation from recurrent CSD (Won and Kraig 2019a,b; Won and Kraig, 2020). This work shows that nasal delivery of IGF-1 (150 µg in 50 µl) significantly reduces trigeminal ganglion CGRP and oxidative stress (i.e., levels of malondialdehyde) levels. In addition, trigeminocervical complex c-fos positive cells were significantly reduced compared to sham (i.e., nasal delivery of 50 µl of succinate buffer) after recurrent CSD (elicited every 10 minutes for 90 minutes).

FIGS. 11 and 14 summarizes the inventors' results which support the suggestion that nasal IGF-1 not only inhibits the initiation of migraine modeled in animals using CSD, but also the consequences of trigeminal system activation.

This work is based on evidence that IGF-1 works upstream of anti-CGRP-mAbs to reduce CNS hyperexcitability and related oxidative stress associated with migraine modeled by CSD, and appears to have a similar protective impact on the trigeminal system. This work demonstrates the utility of combined treatment with an anti-CGRP-mAb and nasal delivery of IGF-1 as a therapeutic against trigeminal system activation associated with migraine.

While migraine is more prevalent in females and female rats are more susceptible to CSD, the inventors will use male Wistar rats (300 gm) in an initial study to avoid the confound of varying menstrual cycle time, which can influence CSD susceptibility. Future studies will examine the impact of anti-CGRP-mAb and nasal IGF-1 treatment in female rats after recurrent CSD.

Migraine will be modeled using recurrent CSD (Grinberg et al., 2019; Won and Kraig 2019a,b; Won and Kraig, 2020). Briefly, the day before recurrent CSD, animals are anesthetized with inhalational isoflurane in oxygen (2-5%) and treated with intranasal IGF-1 (150 µg in 50 µl succinate buffer).

Anesthetized animals are then transferred to a standard stereotaxic head holder under 2-5% isoflurane inhalational anesthesia. Eyes are coated with Artificial Tears and head shaved, cleansed with Betadine, and 0.1 mL of 0.25% Bupivacaine is injected subcutaneously to either side of what will be a left of midline head incision made five minutes later. The underlying skull is scraped free of soft tissue and hemostasis achieved with bone wax. Two 1-2 mm craniotomies are drilled with a Dremel tool at +3 mm anterior to bregma and two mm lateral to the midline (for 0.5M KCl 10-30 nL pressure injections used to initiate CSD. A second craniotomy is placed six mm caudal to bregma and 4.5 mm lateral to the midline (for recording CSD. The surgery area is wiped with Betadine and incision closed with three wound clips. Animals are allowed to awaken and then returned to overnight standard Animal Facility Housing.

The next day (i.e., 20-24 hours later) animals are again be anesthetized as above with inhalational isoflurane and the left femoral vein cannulated for antibody infusion. Select groups of animals (see below) are treated with intravenous infusion either 1 mg/kg anti-CGRP (ab81887) or isotype IgG2a control in 0.5-0.6 ml normal saline. After infusions, the femoral incision is closed with wound clips. Table 1 shows comparative published literature for studies using anti-CGRP-mAb in preclinical migraine studies. Table 2 shows expected costs for use of anti-CGRP-mAb (ab81887) and isotype control.

Note: The inventors have elected to not use subcutaneous injections of Bupivacaine on the second day since the inventors have some evidence that such injections can adversely affect CSD susceptibility.

Animals are stabilized for an hour under anesthesia (1.5% isoflurane in oxygen) after head sutures are removed, eyes coated with Artificial Tears and animals made ready for initiation and recording of CSD under deeper (5%) isoflurane in oxygen, which is then lowered back to 1.5% isoflurane in oxygen during CSD recordings. CSD is initiated as described above one to four hours after antibody infusion. All animals receive nine KCl injections. Then, isoflurane is raised to 5% and animals anesthetized with intraperitoneal ketamine and Xylazine followed quickly by euthanasia via intra-cardiac perfusion with 0.1 mL heparin (1,000 units/ml), then 250 ml of normal saline and finally 250 ml 4% paraformaldehyde in 0.2 M phosphate buffer. Brains plus upper cervical cord and trigeminal ganglia are harvested for measurement of c-fos immunostaining in the trigeminocervical complex and CGRP and oxidative stress (malondialdehyde) levels in the trigeminal ganglion ipsilateral to CSD. Animal groups and endpoints are defined below.

The inventors' previous work shows that 5/group is sufficient to reach statistical significance with a power >0.80 and near or equal to 1.00 for whole animal experiments involving CSD and trigeminal system activation. Therefore, the inventors anticipate using n=5 animals per group here. Animal groups will consist of: 1) treatment with nasal IGF-1+intravenous anti-CGRP-mAb; 2) treatment with nasal IGF-1; 3) treatment with intravenous anti-CGRP-mAb; 4) treatment with nasal IGF-1+intravenous isotype control; 5) treatment with intravenous isotype control; and 6) treatment with nasal succinate buffer.

The inventors will test the impact of anti-CGRP-mAb dosing (n=3/group) on the endpoints after intravenous treatment with: 1 mg/kg anti-CGRP-mAb, 2 mg/kg anti-CGRP-mAb, or Control CSD.

The endpoints for this project are to harvest brain and trigeminal ganglia tissues for immunohistochemical analyses following perfusion with fixative. Trigeminal ganglion measurements are: immunohistochemical assays of CGRP and oxidative stress. Trigeminocervical complex measurements are assays of laminae I and II c-fos immunostaining.

All data analyses are performed blinded to treatments, according to ARRIVE criteria, and statistically treated via ANOVA and post-hoc testing or t-testing as appropriate. In addition per agreement with the Provost's Office, Dr. Anthony Reder, Professor of Neurology at the University of Chicago, is an external monitor to ensure appropriate coding and blinding of all work, which is done by Dr. Lisa Won with Dr. Kraig performing blinded animal experiments and Dr. Kraig performing blinded analyses with Dr. Won performing staining procedures and blinded analyses of c-fos cell counting. All investigators will be authors on related publications.

All data is analyzed using SigmaPlot (v.12.5; Systat Software, Inc., San Jose, CA). All data were subject to normality testing (p-value to reject: 0.05), equal variance testing (p-value to reject: 0.05), and power (1-$\beta$: >0.8). Data will be presented as a natural log ratio of experimental over control data. In this way, a value of "0" would reflect no change from control while a positive logarithm would indicate an increase and a negative logarithm a decrease.

The inventors have used this statistical method for computer-based semi-quantitative immunohistochemical analyses (Kraig et al, 1991).

Figure 16:
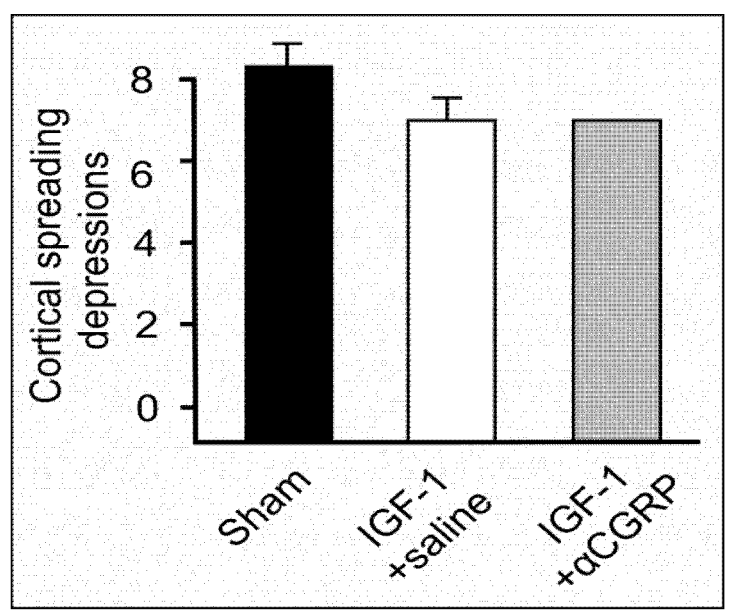
FIG. 16. Cortical spreading depressions. Histograms show number of cortical spreading depressions evoked over 90 minutes for each group. There was no significant difference between groups (p=0.127).

First, the inventors confirmed that there was no significant difference in the number of evoked CSDs between groups (FIG. 16). Sham nasal delivery was, as reported (i.e., 50 µl succinate buffer delivered as 5 µl aliquots to alternating nostrils every two minutes) while under isoflurane inhalational anesthesia (Won and Kraig, 2020). A day later CSD was evoked every nine minutes for a total of 90 minutes via micro-injections of 0.5M KCl (Won and Kraig, 2020).

Similarly, other animals were first treated with intranasal IGF-1 and a day later an intravenous injection of normal saline (one ml). An hour after the latter, CSD was evoked as previously described (Won and Kraig, 2020) and animals harvested under anesthesia by intra-cardiac perfusion-fixation for analyses of the trigeminal ganglion and trigeminocervical complex. A third group of animals was treated with intranasal IGF-1 and a day later given an intravenous injection of a CGRP inhibitor [one mg/kg; Abcam mouse monoclonal anti-CGRP antibody (4901) in one ml; Zeller et al., 2008]. An hour later CSDs were evoked every nine minutes for 90 minutes as done previously (Won and Kraig, 2020). Specific number of CSDs were: Sham (from Won and Kraig, 2020), 8.2±0.49, n=5; Nasal IGF-1+intravenous saline, 7±0.41, n=3; and nasal IGF-1+intravenous anti-CGRP antibody, 7±0, n=3.

Figure 17:
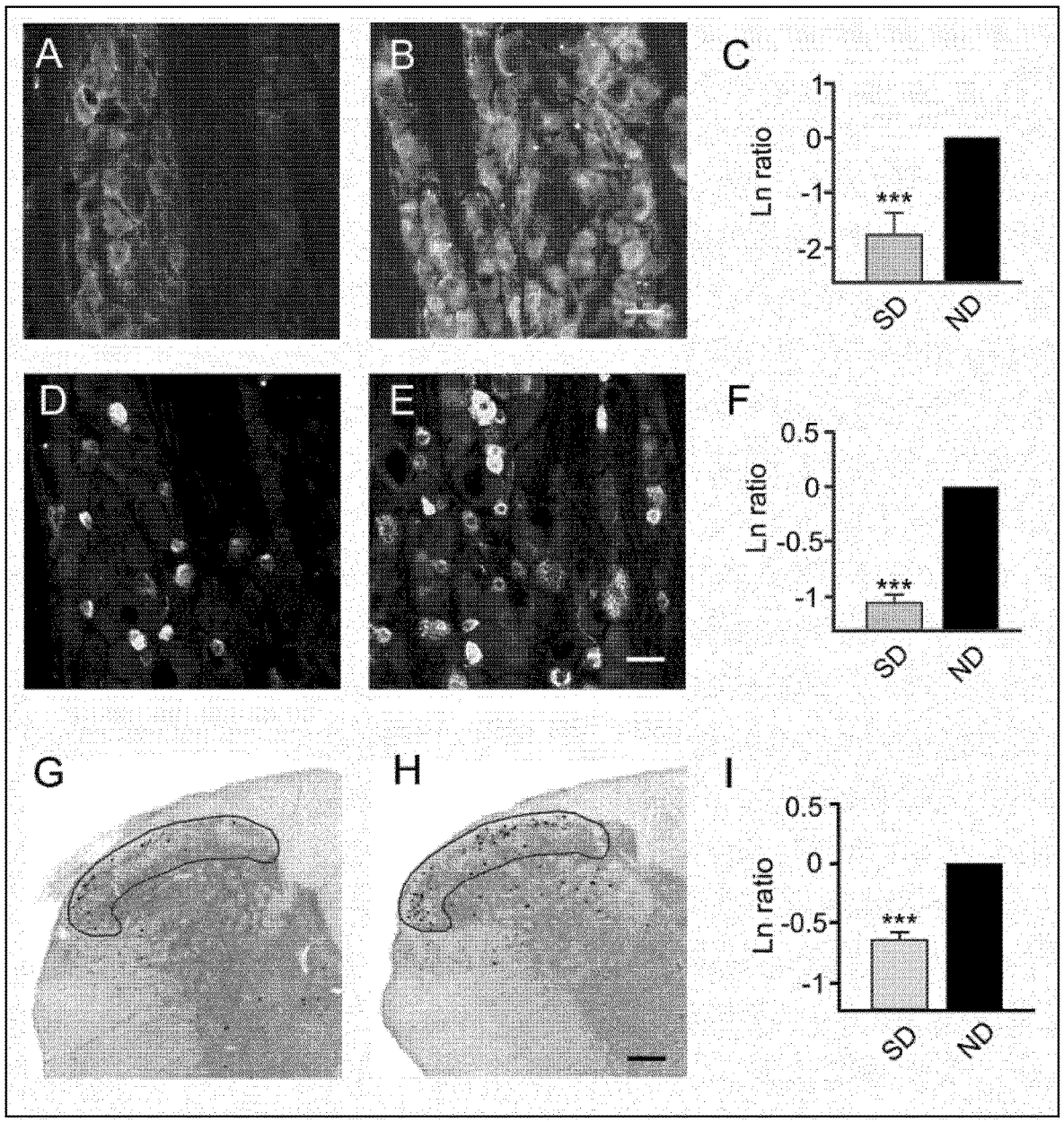
FIG. 17A-I. Trigeminal system activation after recurrent SD and pretreatment with high dose (150 µg) intranasal IGF-1. (Top panel) Intranasal delivery of IGF-1 significantly reduced OS in the trigeminal ganglion after recurrent SD. Representative images show malondialdehyde immunostaining of the V1 area of the trigeminal ganglion after pre-treatment with (A) IGF-1 or (B) vehicle which was followed a day later by 90 minutes of recurrent CSD. (C) Natural log ratio levels of immunostaining after intranasal treatment (IGF-1/sham) showed that IGF-1 significantly (*p<0.001) reduced malondialdehyde levels which reflects an 83% reduction versus comparison to no difference in ratios (i.e., Ln=0). Scale bar=25 µm. (Middle panel) Representative images show CGRP immunostaining of the V1 area of the trigeminal ganglion after pre-treatment with (D) IGF-1 or (E) vehicle which was followed a day later by 90 minutes of recurrent CSD. (F) Natural log ratio levels of immunostaining after intranasal treatment (IGF-1/sham) showed that IGF-1 significantly (*p<0.001) reduced CGRP levels which reflects a 59% reduction versus comparison to no difference (ND) in ratios (i.e., Ln=0). Scale bar=25 µm. (Bottom panel) Representative images show c-fos immunostaining at −4.5 mm caudal to the obex within laminae I and II of the trigeminocervical complex after pre-treatment with (G) IGF-1 or (H) succinate buffer which was followed a day later by 90 minutes of recurrent CSD. Scale bar=200 µm. (I) Natural logarithm ratios (IGF-1/sham) showed that nasal IGF-1 significantly (***p<0.001) reduced c-fos positive cells which reflects a 45% reduction versus comparison to no difference (ND) in ratios (i.e., Ln=0). Data from Won and Kraig, 2020.

2. Second, the inventors illustrate data handling in FIG. 17 and describe it below. All animals for nasal delivery of IGF-1 plus intravenous treatment (i.e., one ml saline or anti-CGRP antibody) followed by 90 minutes of evoked CSDs) were analyzed for trigeminal cervical complex c-fos immunostaining and trigeminal ganglion malondialdehyde immunostaining as previously described (Won and Kraig, 2020).

The inventors used a verified method of quantifying immunostaining log-ratios (experimental/sham) as a further means to reduce potential run-to-run variations in immunostaining for malondialdehyde, CGRP and c-fos positive cells (Won and Kraig, 2020). Images of malondialdehyde and CGRP were analyzed in blinded pairs so that they could be converted once decoded to ratios of experimental/sham image integrated optical intensity, a sensitive metric that not only accounts for the area but also the pixel intensity of related image fluorescence. Immunostaining ratios of one indicated no difference between experimental and sham conditions, while a ratio of less than 1 indicates that experimental treatment reduced immunostaining compared to sham. These ratios were converted to natural logarithms whereby zero corresponded to no difference between experimental and sham conditions, and a t-test (two-tailed) could be used to determine if differences of logarithms varied significantly from zero.

c-fos positive cell quantifications followed a similar pattern to that used for malondialdehyde and CGRP immunostaining. Specifically, c-fos positive cell counts were converted to a ratio (e.g., IGF-1/sham) and the natural logarithm of the results quantified statistically by comparison to "zero" (i.e., no difference ratio of 1.00 or Ln=0. Since maximal trigeminocervical complex changes in the superficial laminae are evident at −4.5 mm caudal to the obex, the inventors report quantitative measurements at this level in the initial study (Won and Kraig, 2020). Here to enhance sensitivity of c-fos measures, the inventors included counts form −4.5 and 6.0 mm caudal to the obex as these two levels are known to show the maximal changes from CSD (Moskowitz et al., 1993).

Image pairs (experimental and sham) were adjusted equally using Adobe Photoshop, which along with CorelDraw was used for final figure construction. Digital electronic files of CSD recordings were processed first in Origin (2019; Microcal, Northhampton, MA) and placed in final form using CorelDraw and Photoshop. Data were analyzed using SigmaPlot software (v. 12.5; Systat Software, Inc. San Jose, CA). All data passed normality testing (p-value to reject: 0.05) and equal variance testing (p-value to reject: 0.05) and power (1-$\beta$: >0.8).

3. The impact of treatment with nasal IGF-1 plus intravenous saline compared to treatment with nasal IGF-1 alone showed no difference (p=0.127; Power: 0.254) in trigeminocervical c-fos immunostaining after 90 minutes of CSD elicited every nine minutes. Specific results were: from original Won and Kraig, 2020 reported data, ln −0.56±0.08, n=5; and new data with intravenous delivery of saline) ln −0.548±0.16, n=3.

Since there was no significant difference between these groups (p=0.97, power=0.054) they were combined for comparison below to treatment with nasal IGF-1 plus intravenous anti-CGRP (ab81887).

Figure 18:
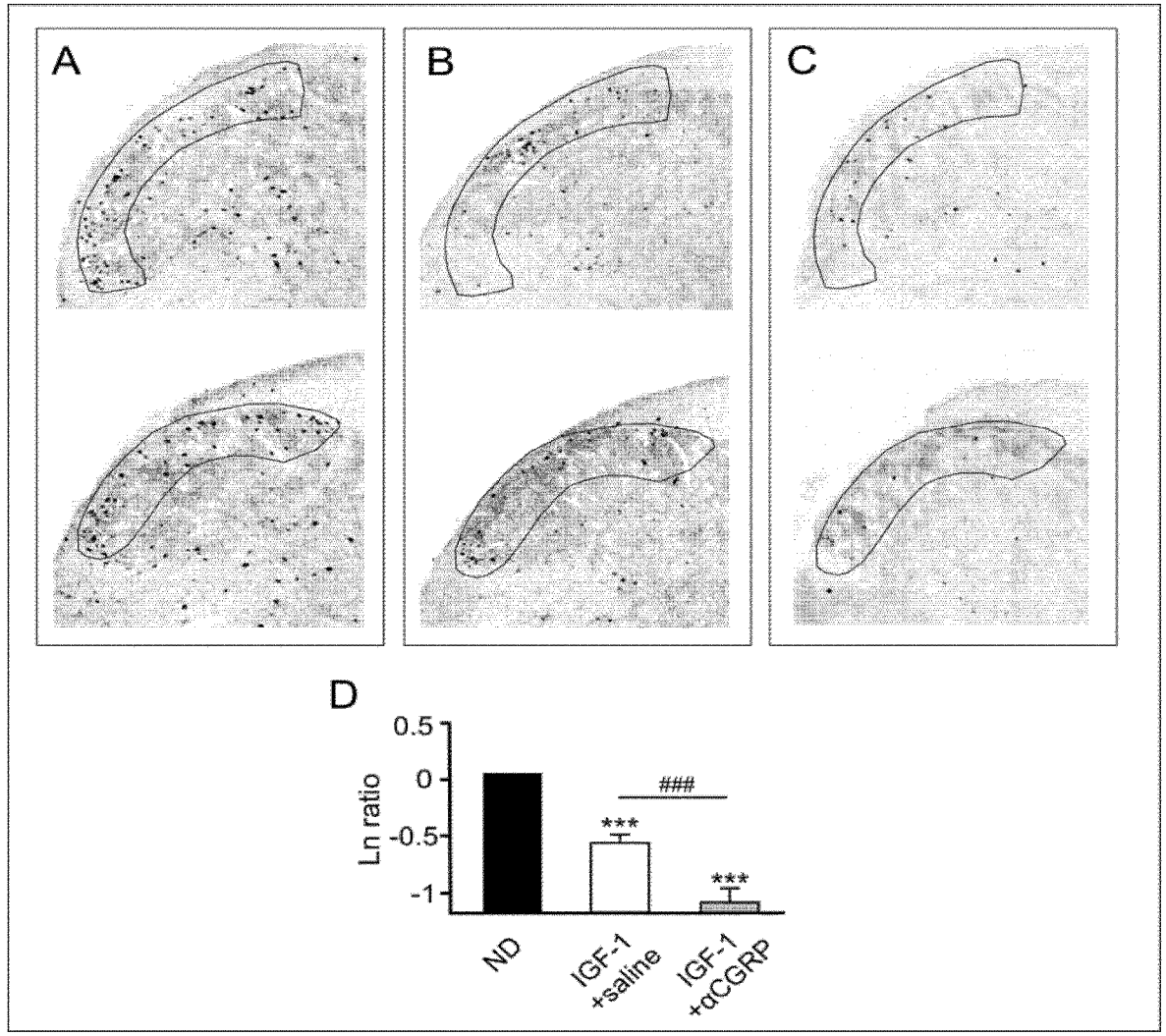
FIG. 18A-D. Representative trigeminocervical c-fos immunostaining after treatment and subsequent recurrent CSD. Representative trigeminal cervical c-fos immunostaining (black dots) in the superficial lamellae (encircled areas) at −4.5 mm for the obex (top) and 6.0 mm from the obex bottom). Images show the result of recurrent activation of CSD for 90 minutes (i.e., with CSD stimulus delivered every nine minutes for 90 minutes) after (A) sham treatment with nasal succinate and subsequent intravenous saline) compared to (B) nasal IGF-1 followed by intravenous saline and (C) nasal IGF-1 followed by intravenous anti-CGRP antibody. Statistical results are shown in (D). Treatment with nasal IGF-1 (with or without subsequent intravenous saline produced a significant (*p<0.001; Power=1.00) protection against c-fos activation from recurrent CSD compared to no difference (ND) in ratios. Nasal IGF-1 followed by intravenous treatment with an anti-CGRP antibody also triggered a significant (*p<0.001) reduction in c-fos activation from recurrent CSD compared to ND in ratios. However, the latter treatment also triggered a significant (####p=0.007) reduction in c-fos activation compared to nasal IGF-1 treatment alone. These results support the suggestion that combined treatment with nasal IGF-1 and an anti-CGRP maybe more effective against migraine than nasal IGF-1 alone.

Results are shown in FIG. 18 and illustrate that, as expected (Won and Kraig, 2020), nasal IGF-1 treatment alone (in this case with treatment of intravenous saline) significantly reduced c-fos immunostaining from recurrent CSD elicited every nine minutes for 90 minutes. However, nasal treatment with IGF-1 followed a day later with intravenous treatment with an anti-CGRP antibody (ab81887) further and significantly reduced c-fos activation from recurrent CSD.

Specific natural logarithm values and significance testing for experimental results shown in FIG. 18 are as follows: control (0.00±0.00, n=10); nasal IGF-1 plus subsequent intravenous saline ln −0.547±0.11, n=10 [i.e., n=7 from prior literature (Won and Kraig, 2020) plus new testing that included intravenous saline (n=3)]); and nasal IGF-1 plus subsequent treatment with anti-CGRP monoclonal antibody (ab81887) that resulted in ln −1.077±0.18 (n=3).

The significance of these changes is listed in FIG. 18 and they reflect a 45% reduction in trigeminocervical c-fos activation from recurrent CSD after nasal IGF-1 (with or without subsequent intravenous saline). This is compared to the added protection of a 66% reduction in c-fos activation from recurrent CSD with pretreatment using nasal IGF-1 and subsequent intravenous anti-CGRP antibody.

With various preclinical models, others have shown that c-fos activation in the trigeminocervical complex after induction of migraine and therapeutic treatments is similar to the protective 45% effects, reported after nasal treatment with nasal IGF-1 alone (Chen et al., 2017; Filiz et al., 2019; Greco et al., 2016; Huang et al., 2018; Jiang et al., 2019; Kilinc et al., 2018; Ramachandran et al., 2014; Sixt et al., 2009). Notably, combined treatment with nasal IGF-1 and an intravenous anti-CGRP antibody produced a 66% reduction in trigeminocervical c-fos activation.

Figure 19:
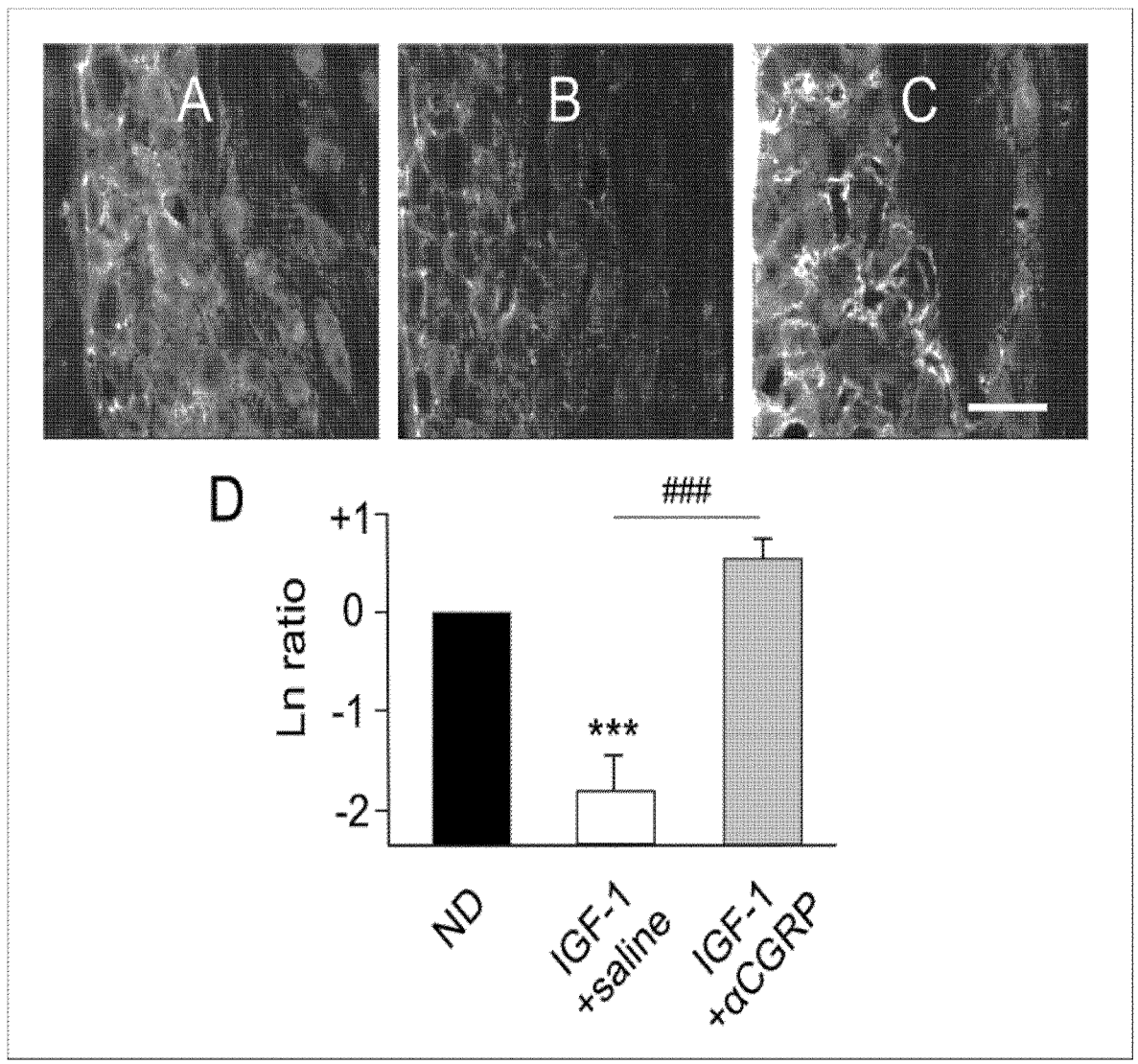
FIG. 19A-D. Trigeminal ganglion V1 area malondialdehyde (MDA) immunostaining. Representative images show (A) V1 area MDA immunostaining after nasal succinate and subsequent intravenous saline treatment before 90 minutes of recurrent CSD elicited every nine minutes. (B) Reduced MDA immunostaining is evident after nasal IGF-1 plus intravenous saline followed by recurrent CSD. (C) However, treatment with nasal IGF-1 followed by intravenous injection of an anti-CGRP mAb (4901) increased trigeminal V1 MDA. In this case the increased immunostaining appears to localize to satellite glia (cells enveloping neurons). Scale bar=100 μm. Statistical treatment (ANOVA) of the three groups showed that nasal IGF-1 triggered a significant (***p<0.001) decrease in the ln ratio (i.e., IGF-1/succinate vehicle) of MDA staining that otherwise would be seen for recurrent CSD. Combined treatment with nasal IGF-1 and intravenous anti-CGRP erased this reduction to a nonsignificant elevation in MDA staining compared to no difference (ND) in ratios. However, this increase in MDA from combined treatment was highly significant (####p<0.001) above the reduction seen with IGF-1 plus intravenous treatment alone (D). These results are consistent with evidence that suggests CGRP can reduce oxidative stress.

4. The inventors next probed for the impact of nasal IGF-1 plus intravenous anti-CGRP treatment on trigeminal ganglion malondialdehyde (MDA) expression (FIG. 19). As previously reported (Won and Kraig, 2020), nasal IGF-1 alone resulted in a ln ratio (i.e., nasal IGF-1 alone) of −1.76±0.29 (n=5) and treatment with nasal IGF-1 plus intravenous saline triggered a reduction in ln ratio of −1.75±0.56 (n=3). T-Test showed that there was no significant difference between these two groups (p=0.982, Power: 0.05). Accordingly, the two groups were combined for subsequent comparison to combined treatment with nasal IGF-1 and intravenous anti-CGRP.

When compared to no difference (ND; 0±0, n=8) in logarithm ratio, the ln ratio of nasal treatment with IGF-1 followed by intravenous saline (one ml) injection followed by recurrent CSD/nasal succinate with or without intravenous saline injection followed by recurrent CSD was −1.76±0.39 (n=8). The ln ratio of treatment with nasal IGF-1 and intravenous anti-CGRP followed by recurrent CSD/nasal succinate with or without intravenous saline injection was 0.67±0.15 (n=3).

This increase in MDA immunostaining of the V1 area of the trigeminal ganglion after treatment with an anti-CGRP agent is consistent with published literature, though never noted before in the trigeminal ganglion. For example, Luo and coworkers (2020) show that CGRP inhibits angiotensin II-induced NADPH oxidase-dependent ROS via the Src/STAT3 signaling pathway. Schaeffer and coworkers (2003) note that CGRP partly protects cultured smooth muscle cells from apoptosis induced by oxidative stress via activation of ERK1/2 MAPK. Sueur and coworkers (2005) report an anti-apoptotic effect of CGRP on oxidative stress-induced injury in H9c2 cardiomyocytes via the RAMP1/CRLR complex. Finally, Wu and coworkers (2015) show that lentivirus mediated over expression of CGRP inhibits oxidative stress in a Schwann cell line.

This unique result of an anti-CGRP mAb on V1 of the trigeminal ganglion supports the suggestion that the anti-CGRP agent used in experiments here (4901) was effectively dosed via the intravenous route and had an impact on organism function.

A. References

The following references, to the extent that they provide exemplary procedural or other details supplementary to those set forth herein, are specifically incorporated herein by reference.

1. Melo-Carrillo A, Noseda R, Nir R R, Schain A J, Stratton J, Strassman A M, Burstein R (2017a) Selective Inhibition of Trigeminovascular Neurons by Fremanezumab: A Humanized Monoclonal Anti-CGRP Antibody. J Neurosci. 37:7149-7163.
2. Melo-Carrillo A, Strassman A M, Nir R R, Schain A J, Noseda R, Stratton J, Burstein R (2017b) Fremanezumab-A Humanized Monoclonal Anti-CGRP Antibody-Inhibits Thinly Myelinated (Aδ) But Not Unmyelinated (C) Meningeal Nociceptors. J Neurosci. 37:10587-10596.
3. Grinberg Y Y, Zitzow L A, Kraig R P (2017) Intranasally administered IGF-1 inhibits spreading depression in vivo. Brain Res. 1677:47-57.
4. Kraig R P, Dong L M, Thisted R, Jaeger C B (1991) Spreading depression increases immunohistochemical staining of glial fibrillary acidic protein. J Neurosci. 11:2187-98.
5. Kohn D F, Clifford C B. Biology and diseases of rats. In: J G Fox, L C Anderson, F M Lowe, F Quimby, editors. Laboratory Animal Medicine. New York: Academic Press, 2002. pp. 121-167.
6. Cohen J M, Dodick D W, Yang R, Newman L C, Li T, Aycardi E, Bigal M E (2017) Fremanezumab as Add-On Treatment for Patients Treated With Other Migraine Preventive Medicines. Headache. 57:1375-1384.
7. Harris H M, Carpenter J M, Black J R, Smitherman T A, Sufka K J (2017) The effects of repeated nitroglycerin administrations in rats; modeling migraine-related endpoints and chronification. J Neurosci Methods. 284:63-70.
8. Won L, Kraig R P (2019a) Nose-to-brain delivery of IGF-1 abrogates trigeminal system activation including oxidative stress and CGRP from recurrent spreading depression. Soc. Neurosci. 45: #3725.
9. Won L. Kraig R P (2019b) Development of nasal insulin-like growth factor-1 as a treatment for migraine. American Headache Society. 59: (Supplement 1) P221LB.
10. Won L, Kraig R P. (2020) Insulin-like growth factor-1 inhibits spreading depression-induced trigeminal calcitonin gene related peptide, oxidative stress & neuronal activation in rat. Brain Res. 1732:146673. doi: 10.1016/j.brainres.2020.146673. Epub 2020 Jan. 21.
11. Zeller J, Poulsen K T, Abdiche Y N, Collier S, Chopra R, Garcia C A, Pons J, Rosenthal A, Shelton D L (2008) CGRP function-blocking antibodies inhibit neurogenic vasodilation without affecting heart rate or arterial blood pressure in the rat. Brit J Pharmacol. 155:1093-1103.
12. Moskowitz M A, Nozaki K and Kraig R P. Neocortical spreading depression provokes the expression of c-fos protein-like immunoreactivity within trigeminal nucleus caudalis via trigeminovascular mechanisms. J Neurosci. 1993; 13: 1167-1177.
13. Chen S P, Qin T, Seidel J L, Zheng Y, Eikermann M, Ferrari M D, van den Maagdenberg A, Moskowitz M A, Ayata C, Eikermann-Haerter K. Inhibition of the P2X7-PANX1 complex suppresses spreading depolarization and neuroinflammation. Brain 2017; 140(6):1643-1656.
14. Filiz A, Tepe N, Eftekhari S, Boran H E, Dilekoz E, Edvinsson L, Bolay H. CGRP receptor antagonist MK-8825 attenuates cortical spreading depression induced pain behavior. Cephalalgia 2019; 39(3):354-365.
15. Greco M C, Capuano A, Navarra P, Tringali G. Lacosamide inhibits calcitonin gene-related peptide production and release at trigeminal level in the rat. Eur J Pain 2016; 20(6):959-966.
16. Huang P, Kuo P H, Lee M T, Chiou L C, Fan P C. Age-dependent anti-migraine effects of valproic acid and topiramate in rats. Front Pharmacol 2018; 9:1095.
17. Jiang L, Ma D, Grubb B D, Wang M. ROS/TRPA1/CGRP signaling mediates cortical spreading depression. J Headache Pain 2019; 20(1):25.
18. Kilinc E, Dagistan Y, Kukner A, Yilmaz B, Agus S, Soyler G, Tore F. Salmon calcitonin ameliorates migraine pain through modulation of CGRP release and dural mast cell degranulation in rats. Clin Exp Pharmacol Physiol 2018; 45(6):536-546.
19. Ramachandran R, Bhatt D K, Ploug K B, Hay-Schmidt A, Jansen-Olesen I, Gupta S, Olesen J. Nitric oxide synthase, calcitonin gene-related peptide and NK-1 receptor mechanisms are involved in GTN-induced neuronal activation. Cephalalgia 2014; 34(2):136-147.
20. Sixt M L, Messlinger K, Fischer M J. Calcitonin gene-related peptide receptor antagonist olcegepant acts in the spinal trigeminal nucleus. Brain 2009; 132(Pt 11):3134-3141.
21. Luo H-M, Wu X Xian X, Wang L-Y, Zhu L-Y, Sun H-Y, Yang L, Liu W-x. Calcitonin gene-related peptide inhibits angiotensin II-induced NADPH oxidase-dependent ROS via the Src/STAT3 signaling pathway. J cell Mol Med 2020; doi:10.1111/jcmm.15288.
22. Schaeffer C, Vandroux D, Thommassin L, Athias P, Rochette L, Connat J-L. Calcitonin gene-related peptide partly protects cultured smooth muscle cells from apoptosis induced by an oxidative stress via activation of ERK1/2 MAPK. Biochmiica et Biphysica Acta 2003; 1643:65-73.

23. Sueur S, Pesant M, Rochette L, Connat J-L. Anti-apoptotic effect of cacitonin gene-related peptide on oxidative stress-induced injury in H9c2 cardiomyocytes via RAMP1/CRLR complex. J Mol Cell Cardiol 2005; 39:955-963.
24. Wu Y, Hao G-M, He J, Lv T-T, Wang H-L, Mao Y-Q, Wang X, Wang W, Han J. Lentivirus mediated over expreessionb of CGRP inhibited oxidative stress in Schwann cell line. Neurosci Lett (2015); 598:52-58.

Example 6

Treatment of Fibromyalgia

The inventors examined whether the therapeutic properties of intranasal delivery of IGF-1 extend to chronic pain, in particular, widespread musculoskeletal pain as is seen in fibromyalgia. Results show that nasal delivery of IGF-1 causes a significant and continued reduction in pain-related behavior (hind-paw withdrawal to tactile stimulation) in a rat model of fibromyalgia.

Intrathecal IGF-1 can reduce pain (Bitar et al., 1996). However, no one has suggested delivering IGF-1 via the nasal route to treat chronic pain including fibromyalgia/chronic fatigue syndrome.

Administration of growth hormone has been suggested for treatment of FM/CFS (Xu et al., 2019; Cuatrecasas et al., 2014) but no attention has been given to the use of IGF-1, perhaps because systemic delivery of IGF-1 after injury can increase hyperalgesia (Xu et al., 2020; Cuatrecasas et al., 2014; Stemkowski et al., 2014).

The electronic von Frey method has been used to assess changes in hind paw tactile sensitivity in several rodent nociceptive models including venom-induced inflammation (Martinov et al., 2013), peripheral neuropathy resulting from oxiplatin treatment (Ferrier et al., 2013) and reserpine-induced fibromyalgia (Fusco et al., 2019).

Experimental Procedures here are described utilizing intranasal IGF-1 for treatment of pain related to the acid saline-induced fibromyalgia model. Rats are anesthetized with 2-5% inhalational isoflurane, remainder oxygen, in a fume hood and the right lower hind limb shaved to ease location of the gastrocnemius muscle. The injection site is cleansed with Betadine and 100 µl of pH 4.0 sterile saline is injected into the right medial gastrocnemius muscle using a 27 G×½ inch sterile hypodermic needle (Day 0). The animals are allowed to recover and then returned to normal housing in individual cages. Five days later (Day 5), the injection procedure is repeated into the same muscle. Control animals receive similar muscle injections with sterile physiological (pH 7.2) saline. Animals injected with acidic, but not physiological saline, exhibit bilateral mechanical hyperalgesia 24 hours after the second injection which lasts for up to 4 weeks (Sluka et al., 2001).

Mechanical hyperalgesia is defined here as a reduction in the threshold (increased sensitivity) to mechanical stimulation of the hind paw (paw withdrawal threshold). An electronic von Frey device (FIG. 20) will be used to stimulate the plantar surface of the left and right hind paws (see behavioral training in Project Details below). Behavioral testing is conducted in the same room where animal are housed according to a standard schedule (Table 2).

TABLE 2

| | Hab1 | Hab2 | BA | D-0 | D-5 | PD1 | PD2 | PD3 | PD4 | PD5 | PD6 | PD7 | PD8 | PD9 |
|---|---|---|---|---|---|---|---|---|---|---|---|---|---|---|
| PWT | | | ✓ | | | ✓ | | | ✓ | | | ✓ | | ✓ |
| SAL (i.m.) | | | | ✓ | ✓ | | | | | | | | | |
| Succ/IGF-1 | | | | | | | ✓ | | | ✓ | | | ✓ | |

A. Methods

Dynamic thermal gradient testing coupled has been used to assess chronic systemic pain (DeSantana et al., 2013; Deuis et al., 2017; Barrot, 2012; Bardin et al., 2009).

However, due to its simplicity and reproducibility, a widely-used, non-inflammatory rodent model which mimics chronic, widespread muscle pain-like behavior was utilized. This fibromyalgia model consists of two unilateral injections of acid saline into the gastrocnemius muscle which produce bilateral, long-lasting mechanical hyperalgesia for up to 4 weeks without motor deficits or tissue damage observed histologically (Sluka et al., 2001), Hind paw withdrawal thresholds obtained using an electronic von Frey device were used as a measure of "inferred pain".

Electronic von Frey (FIG. 20) provides a tool to measure changes in paw withdrawal response to mechanical stimuli as a behavioral read out of pain sensitivity (nociception). Hind paw withdrawal thresholds can be assessed first at baseline and then monitored over time following injury with or without therapeutic intervention. Prior to initiating treatment, it is important that all experimental groups exhibit similar average baseline withdrawal thresholds. The change in nociceptive response is measured as the difference between each individual's experimental and baseline withdrawal threshold measurements (Martinov et al., 2013).

Animals are first adapted to the experimental holding setup (FIG. 21) for 30 minutes×two days (Hab-1 and 2). Then pretreatment measurement of paw withdrawal thresholds (PWT) is performed the day prior to the first acid saline muscle injection (baseline; BA).

Figure 22:
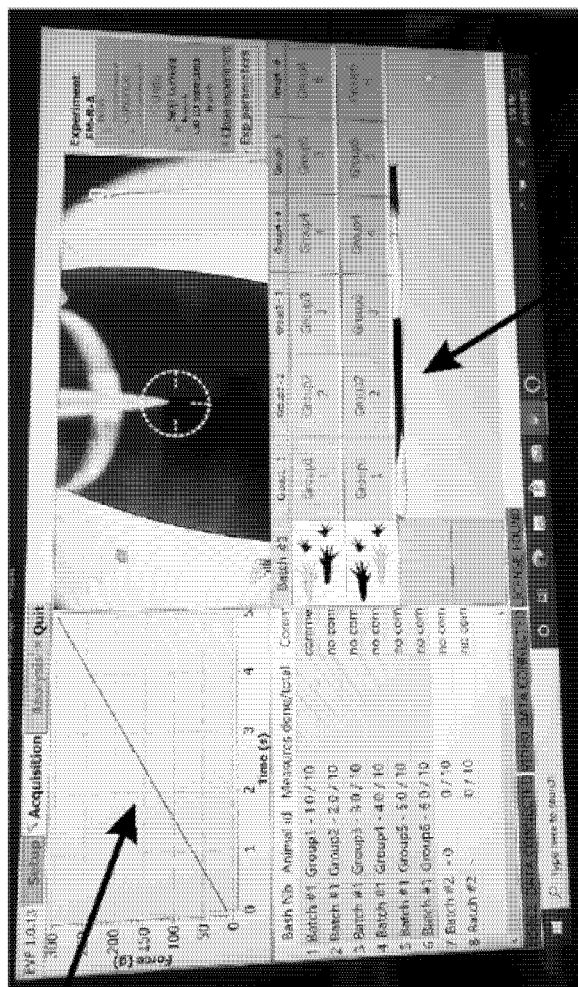
FIG. 22. Screen shot of electronic Von Frey (BIOSEB) system software.

Animals are injected with saline on day 0 (D0) and day five (D5). 24 hours after the second acid saline injection (PD-1) induction of mechanical hyperalgesia is confirmed. Only animals with an increase in hyperalgesia are included for further study (FIG. 22).

Figure 23:
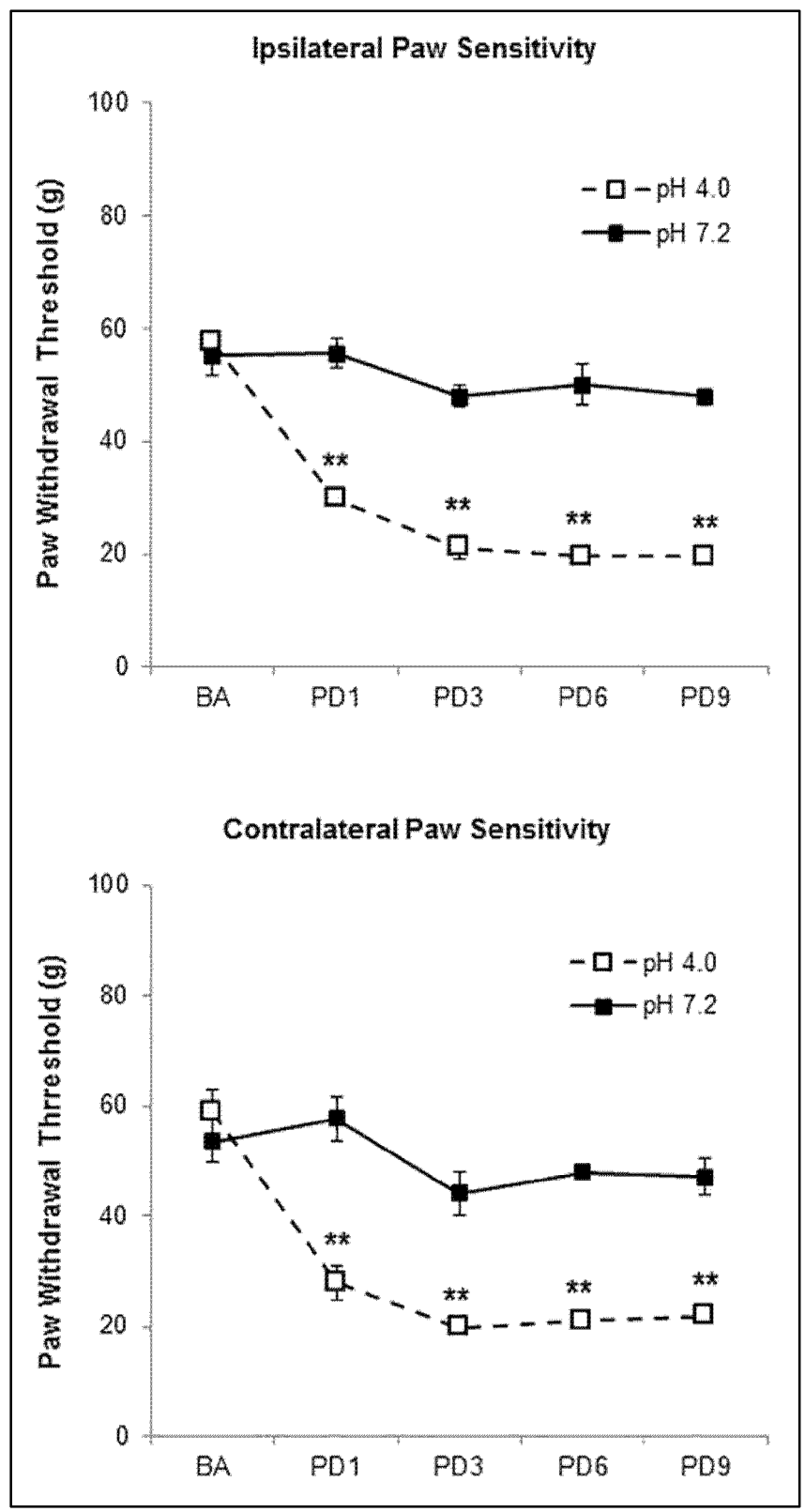
FIG. 23. Demonstration of electronic Von Frey-measured hind paw responses to saline injections (experiment FM-6). Data shows (n=5 measurements/paw) of right (ipsilateral to injection) and left (contralateral to injection) hind paw withdrawal responses at baseline (BA) and 1, 3, 6, and 9 days after saline (pH 4.0—open squares and pH 7.2 solid squares). Acid saline injections produced a persistent and significant reduction in both ipsilateral and contralateral paw withdrawal threshold (**p<0.01 vs pH 7.2 at corresponding time point, t-test per time point n=3 animals/group), 2-tailed T-test per time point pair.

Rats injected twice with physiological saline (pH 7.2, control) should not demonstrate mechanical hyperalgesia and are tested with the electronic von Frey system (FIG. 23). On day PD-2, and every third day afterward (on PD-5 and PD-8) acid saline injected rats exhibiting mechanical hyperalgesia receive intranasal administration of 50 µl volume of either IGF-1 (150 µg/dose) or succinate buffer (vehicle) as previously described (Won and Kraig, 2020).

Experimental Endpoints. The general goal of these experiments is to whether nasal IGF-1 attenuates mechanical hyperalgesia in an acid saline-induced model of fibromyalgia. The endpoint is to monitor paw withdrawal thresholds following repeated IGF-1 dosing after induction of mechanical hyperalgesia. The acid saline muscle injection procedure induces mechanical hyperalgesia in both male and female rats. Since human females tend to have a higher incidence of musculoskeletal pain (fibromyalgia), nasal IGF-1 dose-response experiments will be conducted on female rats first and the optimal dose of IGF-1 selected for testing in male rats. Intranasal administration of succinate buffer will serve as a control for intranasal treatment with each IGF-1 dose.

Experimental groups: A) FEMALES: 1) pH 7.2 saline, i.m.; 2) pH 4.0 saline, i.m.; 3) pH 4.0 saline, i.m.+nasal succinate buffer; 4) pH 4.0 saline, i.m.+nasal IGF-1 (37.5 µg/dose); 5) pH 4.0 saline, i.m.+nasal succinate buffer; 6) pH 4.0 saline, i.m.+nasal IGF-1 (75 µg/dose); 7) pH 4.0 saline, i.m.+nasal succinate buffer; 8) pH 4.0 saline, i.m.+nasal IGF-1 (150 µg/dose); B) MALES: 1) pH 7.2 saline, i.m.; 2) pH 4.0 saline, i.m.; 3) pH 4.0 saline, i.m.+nasal succinate buffer; 4) pH 4.0 saline, i.m.+nasal IGF-1 (optimal dose).

Figure 20:
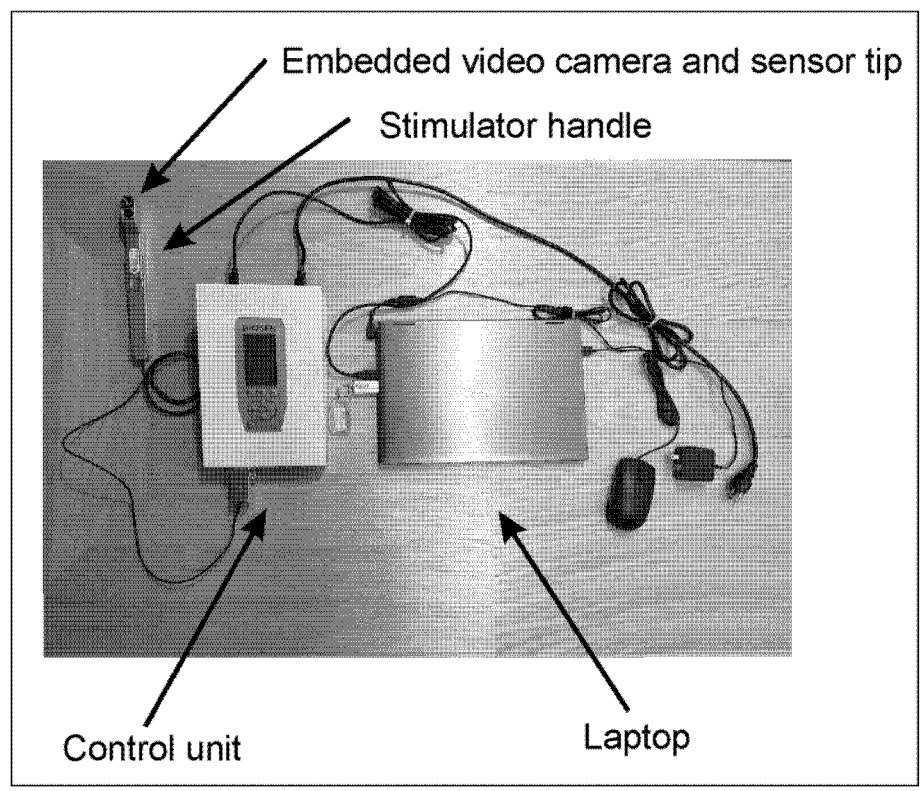
FIG. 20. BIO-EVF5 system from BIOSEB. The video-based BIOSEB (Vitrolles cedex France) electronic Von Frey system is shown. This system allows accurate determination of mechanical pain sensitivity threshold using the hand-held stimulator handle with a video camera and sensor tip that is used to test paw withdrawal threshold. Each measurement is registered via software and laptop computer to create a permanent record. Results are also recorded manually to a lab book.

Behavioral Training Goal: To determine whether intranasal administration of IGF-1 attenuates mechanical hyperalgesia in a non-inflammatory model of long-lasting, widespread muscle pain (fibromyalgia). The method of testing is to assess the mechanical sensitivity threshold (paw withdrawal threshold) will serve as a surrogate measure of pain and will be assessed using an electronic von Frey device (FIG. 20).

Figure 21:
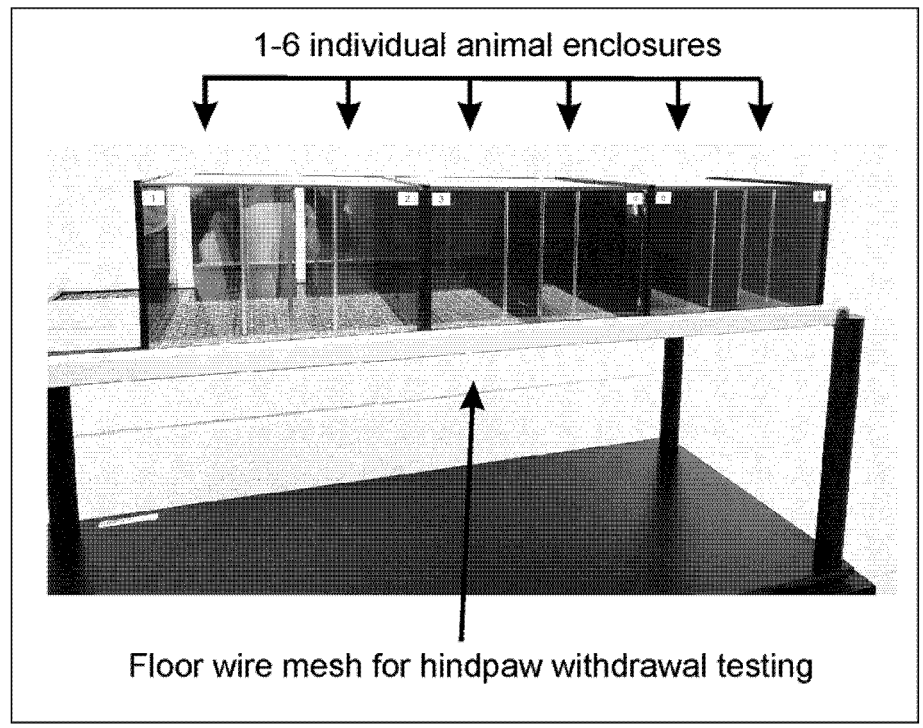
FIG. 21. Individual animal enclosures for Von Frey hind paw withdrawal testing. Image shows six individual rat enclosures where animals are housed for 30 minutes before initiation of hind paw withdrawal testing via the electronic Von Frey unit using a hand-held stimulator that is used to approach the left and right hind paws via the underlying wire mesh. Measurements are made from the left paw and then the right paw per animal and repeated for all animals five times.

Testing consists of placing rats in an acrylic cage module [23 cm×24 cm×14.6 cm (W×L×H)] which rests upon an elevated wire mesh grid floor (FIG. 21). The cage is open on the bottom and divided into 2 compartments (one rat/compartment) with opaque walls to diminish interactions between rats. An electronic von Frey device is used to assess mechanical sensitivity to hind paw stimulation. The device consists of a portable force transducer fitted with an embedded camera and a rigid, plastic filament probe in the stimulator handle. The camera allows the recording and display of video underneath the paws. The filament tip is applied from beneath the wire grid to the plantar surface (center of footpad) of the hind paw in continuous, increasing force until a paw withdrawal response is elicited (i.e., licking or shaking of the paw). The force at which this response occurs is recorded automatically by the electronic device and is designated as the paw withdrawal threshold (FIG. 22).

Habituation: Rats are acclimatized [habituation (Hab1 and Hab2)] to the testing environment for two days prior to conducting baseline measures. On each of the two days, rats are placed in the cage enclosure for 30 minutes to acclimatize and then returned to their home cage. The enclosure and wire mesh is cleaned with 70% ethanol prior to habituating another batch of animals.

Testing: (Baseline): Rats are acclimatized in the test enclosure for 30 min. The tip of the von Frey probe is applied to the center of the footpad and the pressure gradually increased (~15 grams/sec) until a clear withdrawal of the paw is observed. Normal, healthy rats have paw withdrawal thresholds between 50-80 grams. Both hind paws are tested (alternating left and right) with an interval of >5 minutes between registered stimulations on the same hind paw. A minimum of five measurements for each hind paw are obtained for each rat. The enclosure and wire mesh is cleaned with 70% ethanol prior to testing another batch of animals.

A. Figures/Results

Figure 24:
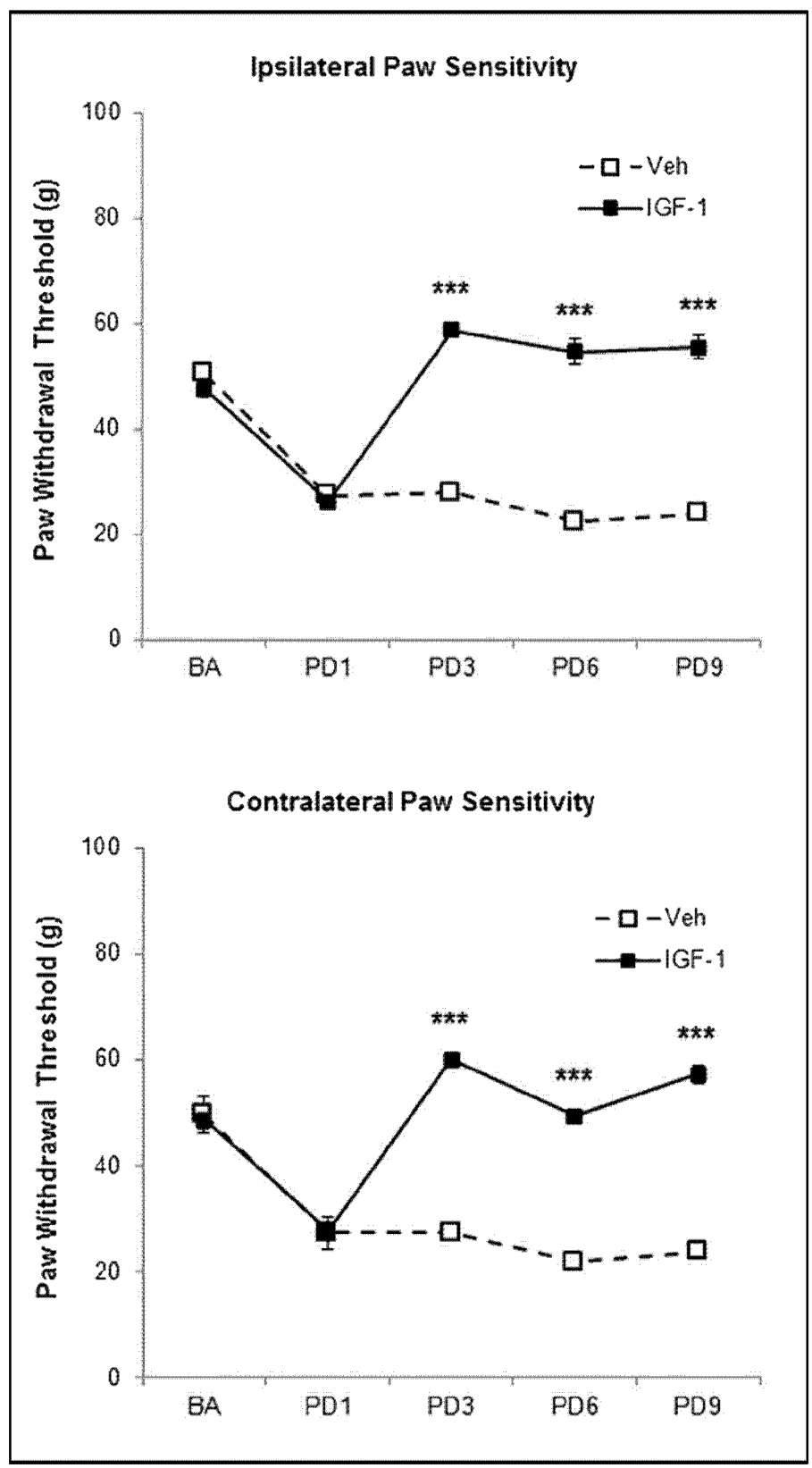
FIG. 24 Impact of nasal treatment with IGF-1 versus succinate (vehicle) from FM-7 experiment. Data shows (n=5 measurements/paw) of right (ipsilateral to injection) and left (contralateral to injection) hind paw withdrawal responses following nasal administration of vehicle (open squares) or IGF-1 (solid squares) in the acid saline hyperalgesia model. ***p<0.001 vs vehicle at corresponding time point, n=3/group, 2-tailed T-test per time point pair.
Figure 25:
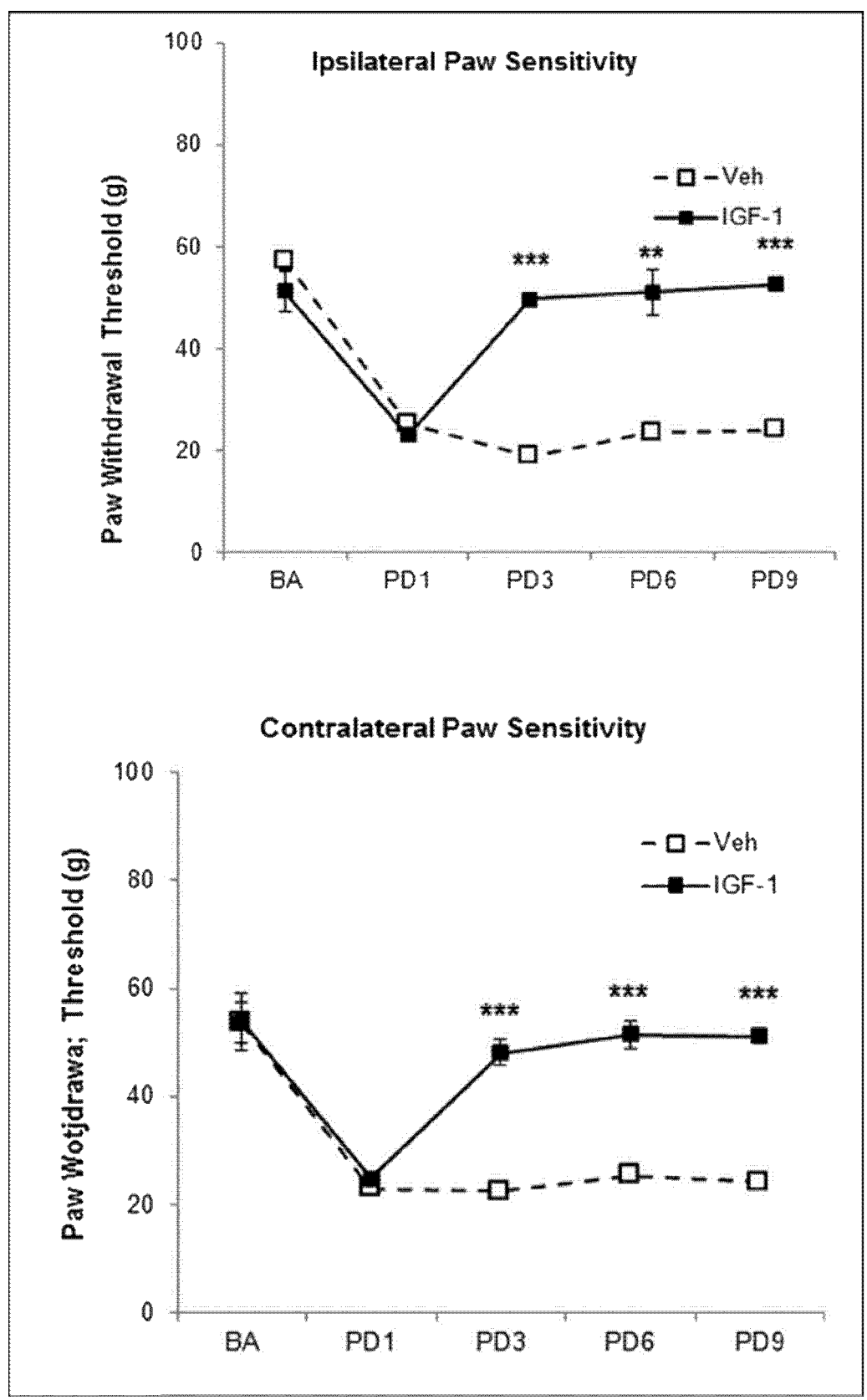
FIG. 25. Impact of nasal treatment with IGF-1 versus succinate (vehicle) from FM-8 experiment. Data shows (n=5 measurements/paw) of right (ipsilateral to injection) and left (contralateral to injection) hind paw withdrawal responses following nasal administration of vehicle (open squares) or IGF-1 (solid squares) in the acid saline hyperalgesia model. p<0.01-*p<0.001 vs vehicle at corresponding time point, n=3/group, 2-tailed T-test per time point pair.

The experimental setup used for the electronic von Frey testing and schedule are shown in FIGS. 20-22 and Table 1. FIGS. 23-25 show results of acid-induced pain threshold withdrawal responses compared to age-matched sham controls.

Adult (~230 g) female Wistar rats (Charles River Laboratories, Wilmington, MA) were used in this study and initially housed one animal per cage under standard animal housing conditions for rats.

Housing included use of static micro isolator cages with corn cob bedding, Enviro-dri nesting material (Shepard Specialty Papers, Watertown, TN) and nestlets (Ancare Corporation, Bellmore, NY) for enrichment. Rats were maintained in a 12-hour light-dark cycle with controlled humidity and temperature in our Central Animal Facility. Rats had free access to food and water throughout experiments and were observed daily for evidence of normal feeding, grooming and ambulatory activity. All animal procedures were approved by the Institutional Animal Care and Use Committee at the University of Chicago, were conducted in accordance with the Guidelines of the National Institutes of Health Guide for Care and Use of Laboratory Animals (2011) and were patterned after ARRIVE guidelines.

Two investigators were used for all experiments. One investigator delivered all paw stimuli and was blinded to experimental treatments. The second investigator recorded paw withdrawal threshold (PWT) force levels, procedures modeled after the experimental strategy reported by Martinov et al., 2013. Furthermore, in all experiments (FM-6, FM-7 and FM-8; n=6 rats/experiment), a baseline (BA) threshold withdrawal response was first established as outlined by Martinov et al., 2013 (Table 1).

Specifically, baseline (BA) measurements of paw withdrawal threshold (PWT) were determined for six animals/experiment prior to experimental treatment. In the case of nasal IGF-1 or vehicle (succinate buffer) treatment, after two acid saline injections, animals within a group were divided into two subgroups (n=3/group) based on equally distributing the differences between baseline (BA) and paw withdrawal threshold (PWT) [i.e., (BA)-(PWT)] at PD1 (Table 1). This maneuver ensured that the average paw withdrawal threshold (PWT) after acid injections was similar between groups (Martinov et al., 2013). All paw withdrawal threshold (PWT) measurements for experiments FM-6, FM-7 and FM-8 (i.e., FIGS. 23-25) are absolute average values of the threshold force needed to elicit paw withdrawal. Experiments included nasal IGF-1 and vehicle treated animals per measurement run.

FIG. 23 shows results for experiment FM-6 where the paw withdrawal thresholds (PWT) were compared between injection of acid saline (pH 4.0) or vehicle (pH 7.2 saline). Paw withdrawal threshold responses show that acid saline injections caused a persistent and significant (**p<0.01) reduction in paw withdrawal threshold measured at PD 1, PD 3, PD 6 and PD 9. This confirms the utility and reproducibility of the hind paw acid saline injection (i.e., model of fibromyalgia) strategy used in experiments described here.

Next, the impact of recurrent treatment with nasal IGF-1 (or succinate vehicle) was tested on paw withdrawal threshold (PWT) in the acid saline hyperalgesia model (FIG. 24-25). In both experiments effective induction of hyperalgesia (i.e., reduced paw withdrawal threshold) was first established at PD-1. Then animals were treated with nasal IGF-1 (or vehicle) three times (i.e., PD-2, PD-5 and PD8) (Table 1). A day after each treatment (i.e., PD-3, PD-6 and PD-9), paw withdrawal threshold (PWT) measurements were completed.

In two separate experiments [(FM-7 and FM-8) FIGS. 24 and 25] using n=3 animals per experiment group, IGF-1 treatment induced significant (p<0.01-*p<0.001) protection against acid-induced hind paw hyperalgesia. This data strongly supports the development of nasal IGF-1 as an effective therapeutic for treatment of fibromyalgia including chronic pain syndromes and chronic fatigue syndrome.

B. References

Bitar M S, Al-Bustan M, Nehme C L, et al. Antinociceptive action of intrathecally administered IGF-I and the expression of its receptor in rat spinal cord. Brain Res. 1996; 737: 292-294.

Xu J, Casserly E, Yin Y, Cheng J. A Systematic Review of Growth Hormone in Pain Medicine: From Rodents to Humans. Pain Med. 2020 Jan. 1; 21(1):21-31. doi: 10.1093/pm/pny280.

Ciucci F, Putignano E, Baroncelli L, et al. Insulin-like growth factor 1 (IGF-1) mediates the effects of enriched environment (EE) on visual cortical development. PLoS One. 2007; 2: e475.

Bjersing J L, Larsson A, Palstam A, Ernberg M, Bileviciute-Ljungar I, Löfgren M, Gerdle B, Kosek E, Mannerkorpi K. Benefits of resistance exercise in lean women with fibromyalgia: involvement of IGF-1 and leptin. BMC Musculoskelet Disord. 2017 Mar. 14; 18(1):106. doi: 10.1186/s12891-017-1477-5.

Mannerkorpi K, Landin-Wilhelmsen K, Larsson A, Cider Å, Arodell O, Bjersing J L. Acute effects of physical exercise on the serum insulin-like growth factor system in women with fibromyalgia. BMC Musculoskelet Disord. 2017 Jan. 25; 18(1):37. doi: 10.1186/s12891-017-1402-y.

Cuatrecasas G1, Alegre C, Casanueva F F. GH/IGF1 axis disturbances in the fibromyalgia syndrome: is there a rationale for GH treatment Pituitary. 2014 June; 17(3): 277-83. doi: 10.1007/s11102-013-0486-0.

Won L, Kraig R P. (2020) Insulin-like growth factor-1 inhibits spreading depression-induced trigeminal calcitonin gene related peptide, oxidative stress & neuronal activation in rat. Brain Res. 1732:146673. doi: 10.1016/j.brainres.2020.146673.

DeSantana J M, da Cruz K M, Sluka K A. Animal models of fibromyalgia Arthritis Res Ther. 2013; 15(6):222.

Deuis J R, Dvorakova L S, Vetter I. Methods Used to Evaluate Pain Behaviors in Rodents. Front Mol Neurosci. 2017 Sep. 6; 10:284. doi: 10.3389/fnmol.2017.00284. eCollection 2017.

Barrot M. Tests and models of nociception and pain in rodents. Neuroscience. 2012 Jun. 1; 211:39-50. doi: 10.1016/j.neuroscience.2011.12.041.

Bardin L1, Malfetes N, Newman-Tancredi A, Depoortère R. Chronic restraint stress induces mechanical and cold allodynia, and enhances inflammatory pain in rat: Relevance to human stress-associated painful pathologies. Behav Brain Res. 2009 Dec. 28; 205(2):360-6. doi: 10.1016/j.bbr.2009.07.005.

Sluka K A, Kalra A, Moore S A Muscle Nerve. Unilateral intramuscular injections of acidic saline produce a bilateral, long-lasting hyperalgesia. Muscle Nerve 2001. 24:37-46.

Stemkowski P L, Zamponi G W. The tao of IGF-1: insulin-like growth factor receptor activation increases pain by enhancing T-type calcium channel activity. Sci Signal. 2014 Oct. 7; 7(346):pe23. doi: 0.1126/scisignal.2005826.

Ferrier, J., Bayet-Robert, M., Pereira, B., Daulhac, L., Eschalier, A., Pezet, D., Moulinoux, J-P. & Balayssac, D. A polyamine-deficient diet prevents oxaliplatin-induced acute cold and mechanical hypersensitivity in rats. 2013. PLoS ONE 8(10), e77828, doi: 10.1371/journal.pone.0077828.

Fusco, R., Siracusa, R., D'Amico, R., Peritore, A. F., Cordaro, M., Gugliandolo, E., Crupi, R., Impellizzeri, D., Cuzzocrea, S., & Di Paola, R. Melatonin plus folic acid treatment ameliorates reserpine-induced fibromyalgia: an evaluation of pain, oxidative stress, and inflammation. 2019. Antioxidants 8, 628, doi:10.3390/antiox8120628.

Martinov, T., Mack, M., Sykes, A. & Chatterjea, D. Measuring changes in tactile sensitivity in the hind paw of mice using an electronic von Frey apparatus. 2013. J. Vis. Exp. 82, e51212, doi:10.3791/51212.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for treating a chronic pain syndrome patient, the method comprising administering to the patient an effective amount of an insulin growth factor receptor (IGFR) activator; wherein the chronic pain syndrome comprises fibromyalgia or chronic fatigue syndrome; wherein the method comprises the treatment of widespread muscle pain; and wherein the method further comprises administration of a calcitonin gene-related peptide (CGRP) inhibitor.

2. The method of claim 1, wherein the IGFR activator is IGF-1.

3. The method of claim 1, wherein the CGRP inhibitor comprises a CGRP antibody or a CGRP receptor antibody.

4. The method of claim 3, wherein the antibody or antigen binding fragment comprises fremanezumab, erenumab, galcanezumab, eptinezumab, or an antigen binding fragment thereof.

5. The method of claim 1, wherein the CGRP inhibitor comprises a small molecule; and wherein the small molecule comprises ubrogepant, rimegepant or atogepant.

6. The method of claim 1, further comprising administering a second IGFR activator, and optionally wherein the second IGFR activator comprises insulin.

7. The method of claim 1, wherein one or both of the IGFR activator and the CGRP inhibitor is administered to the patient intranasally.

8. The method of claim 1, wherein the CGRP inhibitor is administered subcutaneously.

9. The method of claim 1, wherein the IGFR activator is administered intranasally.

10. The method of claim 1, further comprising administering to the patient IL-11 and/or interferon γ.

11. The method of claim 1, wherein the method further comprises administering an additional agent; wherein the additional agent comprises one or more of an inhibitor of PACAP, VIP, PACAP receptor, VIP receptor, TRP, and TRP receptor.

* * * * *

SEQUENCE LISTING

<160> NUMBER OF SEQ ID NOS: 5

<210> SEQ ID NO 1
<211> LENGTH: 119
<212> TYPE: PRT
<213> ORGANISM: Homo sapiens

<400> SEQUENCE: 1

Met Ala Leu Cys Leu Leu Thr Phe Thr Ser Ser Ala Thr Ala Gly Pro
1               5                   10                  15

Glu Thr Leu Cys Gly Ala Glu Leu Val Asp Ala Leu Gln Phe Val Cys
            20                  25                  30

Gly Asp Arg Gly Phe Tyr Phe Asn Lys Pro Thr Gly Tyr Gly Ser Ser
        35                  40                  45

```
Ser Arg Arg Ala Pro Gln Thr Gly Ile Val Asp Glu Cys Cys Phe Arg
 50                  55                  60

Ser Cys Asp Leu Arg Arg Leu Glu Met Tyr Cys Ala Pro Leu Lys Pro
 65                  70                  75                  80

Ala Lys Ser Ala Arg Ser Val Arg Ala Gln Arg His Thr Asp Met Pro
                 85                  90                  95

Lys Thr Gln Lys Glu Val His Leu Lys Asn Ala Ser Arg Gly Ser Ala
            100                 105                 110

Gly Asn Lys Asn Tyr Arg Met
            115

<210> SEQ ID NO 2
<211> LENGTH: 71
<212> TYPE: PRT
<213> ORGANISM: Unknown
<220> FEATURE:
<223> OTHER INFORMATION: Description of Unknown:
      IGF-1 sequence

<400> SEQUENCE: 2

Met Gly Pro Glu Thr Leu Cys Gly Ala Glu Leu Val Asp Ala Leu Gln
 1               5                  10                  15

Phe Val Cys Gly Asp Arg Gly Phe Tyr Phe Asn Lys Pro Thr Gly Tyr
                 20                  25                  30

Gly Ser Ser Arg Arg Ala Pro Gln Thr Gly Met Val Asp Glu Cys Cys
             35                  40                  45

Phe Arg Ser Cys Asp Leu Arg Arg Leu Glu Met Tyr Cys Ala Pro Leu
 50                  55                  60

Lys Pro Ala Lys Ser Ala
 65                  70

<210> SEQ ID NO 3
<211> LENGTH: 110
<212> TYPE: PRT
<213> ORGANISM: Homo sapiens

<400> SEQUENCE: 3

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                 20                  25                  30

Ser His Leu Val Glu Ala Leu Tyr Leu Val Cys Gly Glu Arg Gly Phe
             35                  40                  45

Phe Tyr Thr Pro Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
                100                 105                 110

<210> SEQ ID NO 4
<211> LENGTH: 107
<212> TYPE: PRT
<213> ORGANISM: Homo sapiens

<400> SEQUENCE: 4
```

-continued

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20              25                  30

Ser His Leu Val Glu Ala Leu Tyr Leu Val Cys Gly Glu Arg Gly Phe
        35              40                  45

Phe Tyr Thr Pro Lys Thr Arg Arg Glu Ala Glu Val Gly Gln Val Glu
    50              55                  60

Leu Gly Gly Gly Pro Gly Ala Gly Ser Leu Gln Pro Leu Ala Leu Glu
65              70                  75                  80

Gly Ser Leu Gln Lys Arg Gly Ile Val Glu Gln Cys Cys Thr Ser Ile
            85              90                  95

Cys Ser Leu Tyr Gln Leu Glu Asn Tyr Cys Asn
            100             105

<210> SEQ ID NO 5
<211> LENGTH: 70
<212> TYPE: PRT
<213> ORGANISM: Unknown
<220> FEATURE:
<223> OTHER INFORMATION: Description of Unknown:
      IGF-1 sequence

<400> SEQUENCE: 5

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20              25                  30

Ser Ser Ser Arg Arg Ala Pro Gln Thr Gly Ile Val Asp Glu Cys Cys
            35              40                  45

Phe Arg Ser Cys Asp Leu Arg Arg Leu Glu Met Tyr Cys Ala Pro Leu
    50              55                  60

Lys Pro Ala Lys Ser Ala
65              70
```